United States Patent
O'Shea et al.

(10) Patent No.: US 9,187,733 B2
(45) Date of Patent: Nov. 17, 2015

(54) ANTI-CANCER ADENOVIRUSES

(71) Applicant: Salk Institute for Biological Studies, La Jolla, CA (US)

(72) Inventors: Clodagh O'Shea, San Diego, CA (US); Colin Powers, San Diego, CA (US)

(73) Assignee: Salk Institute for Biological Studies, La Jolla, CA (US)

( * ) Notice: Subject to any disclaimer, the term of this patent is extended or adjusted under 35 U.S.C. 154(b) by 247 days.

(21) Appl. No.: 13/768,933

(22) Filed: Feb. 15, 2013

(65) Prior Publication Data

US 2013/0243729 A1 Sep. 19, 2013

Related U.S. Application Data

(63) Continuation of application No. PCT/US2011/048005, filed on Aug. 16, 2011.

(60) Provisional application No. 61/374,215, filed on Aug. 16, 2010.

(51) Int. Cl.
*A01N 63/00* (2006.01)
*A61K 48/00* (2006.01)
*C12N 7/04* (2006.01)
*C12N 7/00* (2006.01)
*A61K 35/761* (2015.01)

(52) U.S. Cl.
CPC .............. *C12N 7/04* (2013.01); *A61K 35/761* (2013.01); *C12N 7/00* (2013.01); *C12N 2710/10322* (2013.01); *C12N 2710/10332* (2013.01)

(58) Field of Classification Search
None
See application file for complete search history.

(56) References Cited

U.S. PATENT DOCUMENTS

| | | |
|---|---|---|
| 6,475,480 B1 | 11/2002 | Mehtali et al. |
| 2001/0039046 A1 | 11/2001 | Yeh et al. |
| 2003/0220284 A1 | 11/2003 | Yotnda et al. |
| 2004/0091456 A1 | 5/2004 | Nakai et al. |
| 2005/0201978 A1 | 9/2005 | Lipton |
| 2012/0020924 A1 | 1/2012 | Nakai et al. |
| 2013/0243729 A1* | 9/2013 | O'Shea et al. ............... 424/93.2 |

FOREIGN PATENT DOCUMENTS

| | | |
|---|---|---|
| EP | 1284294 A1 | 2/2003 |
| WO | WO 01/90392 | 11/2001 |
| WO | WO 03/092579 | 11/2003 |
| WO | WO 2004/031357 | 4/2004 |
| WO | WO 2010/037027 | 4/2010 |

OTHER PUBLICATIONS

Alba, et al., "Gutless adenovirus: last generation adenovirus for gene therapy", *Gene Therapy*, 2005, 12(1), 10 pages.

Batzer et al., "Enhanced evolutionary PCR using oligonucleotides with inosine at the 3'-terminus", *Nucleic Acid Research*, 1991, 19(18):5081.

Barton, et al., "Second-Generation Replication-Competent Oncolytic Adenovirus Armed with Improved Suicide Genes and ADP Gene Demonstrates Greater Efficacy without Increased Toxicity", *Molecular Therapy*, 2006, 13(2):347-356.

Berge et al., "Pharmaceutical Salts", *Journal of Pharmaceutical Science*, 1977, 66:1-19.

Evans, J.D. & Hearing, P., "Relocalization of the Mre11-Rad50-Nbs1 Complex by the Adenovirus E4 ORF3 Protein is Required for Viral Replication", *Journal of Virology*, 2005, 79(10):6207-6215.

Extended European Search Report dated Dec. 11, 2013 for European Application No. 11818698.0, 10 pages.

Henikoff, S. & Henikoff, J.G., "Amino acid substitution matrices from protein blocks", *Proc. Natl. Acad. Sci. USA*, 1992, 89:10915-10919.

International Preliminary Report on Patentability and Written Opinion dated Feb. 19, 2013 for International Application No. PCT/US2011/048005, 5 pages.

International Search Report dated Mar. 23, 2012 for International Application No. PCT/US2011/048005, 6 pages.

Kirn, D., "Clinical research results with dl1520 (Onyx-015, a replication-selective adenovirus for the treatment of cancer: what have we learned?", *Gene Therapy*, 2001, 8(2):89-98.

Leicher et al., "Coexpression of the KCNA3B Gene Product with Kv1.5 Leads to a Novel A-type Potassium Channel", *The Journal of Biological Chemistry*, 1998, 273(52):35095-35101.

Leppard et al., "Adenovirus type 5 E4 Orf3 protein targets promyelocytic leukaemia (PML) protein nuclear domains for disruption via a sequence in PML isoform II that is predicted as protein as a protein interaction site of bioinformatics anaylsis", *Journal of General Virology* 2009, 90(1):95-104.

Pearson, W. R. & Lipman, D.J., "Improved tools for biological sequence comparison", *Proc. Nat'l. Acad. Sci. USA*, 1988, 85:2444-2448.

Rossolini et al., "Use of deoxyinosine-containing primers vs degenerate primers for polymerase chain reaction based on ambiguous sequence information", *Mol. Cell. Probes*, 1994, 8:91-98.

Smith T.F., & Waterman, M.S., "Comparison of Biosequences", *Advances in Applied Mathematics*, 1981, 2:482-489.

Soria et al., "Heterochromatin silencing of p53 target genes by a small viral protein", *Nature*, 2010, 466(7310):1076-1083.

Ullman et al., "Adenovirus E4 ORF3 Protein Inhibits the Interferon-Mediated Antiviral Response", *Journal of Virology*, 2007, 81(9):4744-4752.

Shepard and Ornelles, "E4orf13 is Necessary for Enhanced S-Phase Replication of Cell Cycle-Restricted Subgroup C Adenoviruses," *J Virol* 77(15):8593-8595, 2003.

* cited by examiner

*Primary Examiner* — Michael Burkhart
(74) *Attorney, Agent, or Firm* — Klarquist Sparkman, LLP

(57) ABSTRACT

Anti-cancer adenoviruses, methods of use and methods of making the same are provided herein.

9 Claims, 41 Drawing Sheets

Fig. 1C
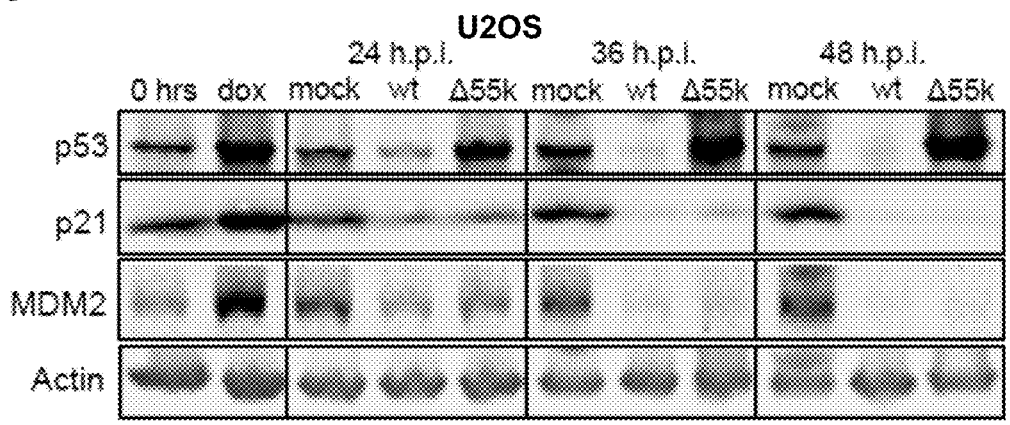
Fig. 1D
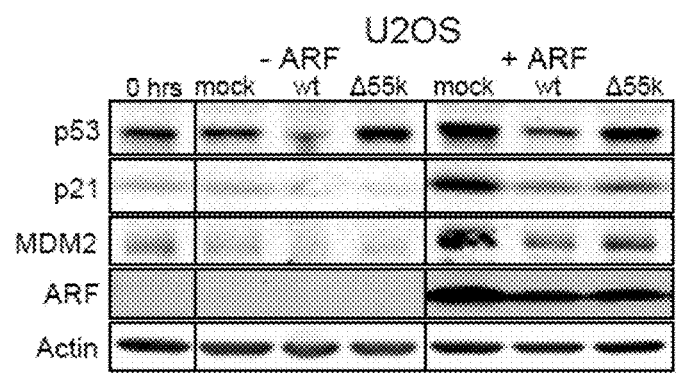
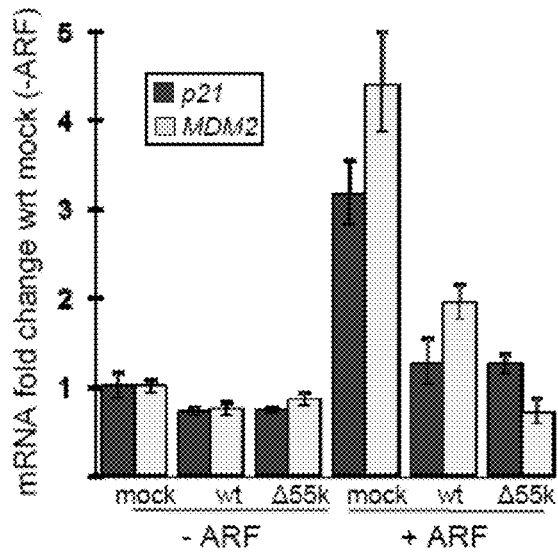

Differentially up-regulated genes (265) in Δ55k/ΔORF3 vsΔ55k

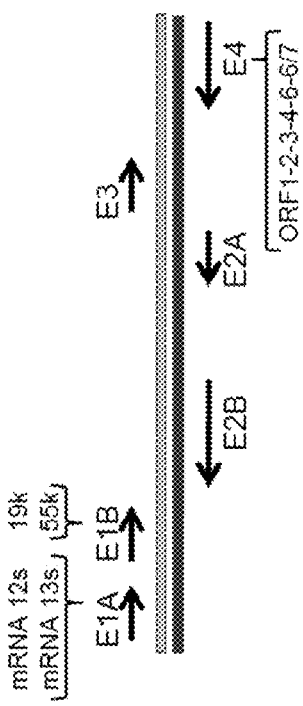

Fig. 10

| Early Gene Cluster | Viral Proteins | Cellular Binding Proteins & Functions |
|---|---|---|
| E1A | 12s<br>13s | p300, CBP, p400, RB, p107, p130, YY1, CTBP, DYRK<br>Above + TBP, SUR2/MED23 |
| E1B | 55k<br>19k | p53, MRE11, mSIN3A/HDAC1, E1B-AP<br>BH3 proteins-Bax, Bak |
| E2 | E2A<br>E2B | DNA Binding Protein<br>Terminal Protein, DNA polymerase |
| E4 | E4-ORF1<br>E4-ORF2<br>E4-ORF3<br>E4-ORF4<br>E4-ORF6<br>E4-ORF6/7 | PI-3 kinase activation, MUPP1, DLG<br>Functions and targets unknown<br>Mislocalizes PML, MRE11 and TIF1α<br>PP2A binding protein, mTOR activation, SR protein phosphorylation<br>Binds to E1B-55k and recruits CUL5, RBX1 and Elongin C to target p53 and MRE11 for ubiquitination<br>E2F and Dp-1 dimerization |

Fig. 28
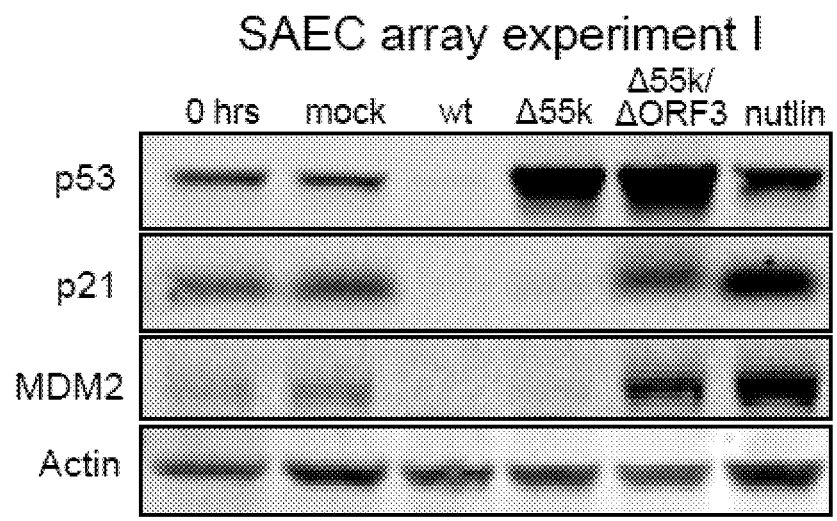
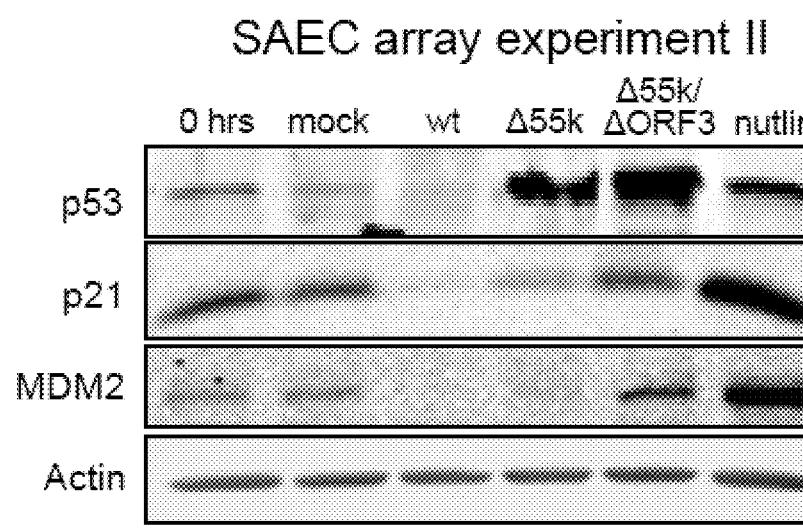

SEQUENCE LISTING

```
<160> NUMBER OF SEQ ID NOS: 3

<210> SEQ ID NO 1
<211> LENGTH: 150
<212> TYPE: PRT
<213> ORGANISM: Human adenovirus 5

<400> SEQUENCE: 1

Met Thr Thr Ser Gly Val Pro Phe Gly Met Thr Leu Arg Pro Thr Arg
1               5                   10                  15

Ser Arg Leu Ser Arg Arg Thr Pro Tyr Ser Arg Asp Arg Leu Pro Pro
            20                  25                  30

Phe Glu Thr Glu Thr Arg Ala Thr Ile Leu Glu Asp His Pro Leu Leu
        35                  40                  45

Pro Glu Cys Asn Thr Leu Thr Met His Asn Ala Trp Thr Ser Pro Ser
    50                  55                  60

Pro Pro Val Lys Gln Pro Gln Val Gly Gln Gln Pro Val Ala Gln Gln
65                  70                  75                  80

Leu Asp Ser Asp Met Asn Leu Ser Glu Leu Pro Gly Glu Phe Ile Asn
                85                  90                  95

Ile Thr Asp Glu Arg Leu Ala Arg Gln Glu Thr Val Trp Asn Ile Thr
            100                 105                 110

Pro Lys Asn Met Ser Val Thr His Asp Met Met Leu Phe Lys Ala Ser
        115                 120                 125

Arg Gly Glu Arg Thr Val Tyr Ser Val Cys Trp Glu Gly Gly Gly Arg
    130                 135                 140

Leu Asn Thr Arg Val Leu
145                 150

<210> SEQ ID NO 2
<211> LENGTH: 176
<212> TYPE: PRT
<213> ORGANISM: Human adenovirus 5
```

<400> SEQUENCE: 2

```
Met Glu Ala Trp Glu Cys Leu Glu Asp Phe Ser Ala Val Arg Asn Leu
1               5                   10                  15

Leu Glu Gln Ser Ser Asn Ser Thr Ser Trp Phe Trp Arg Phe Leu Trp
            20                  25                  30

Gly Ser Ser Gln Ala Lys Leu Val Cys Arg Ile Lys Glu Asp Tyr Lys
        35                  40                  45

Trp Glu Phe Glu Glu Leu Leu Lys Ser Cys Gly Glu Leu Phe Asp Ser
    50                  55                  60

Leu Asn Leu Gly His Gln Ala Leu Phe Gln Glu Lys Val Ile Lys Thr
65                  70                  75                  80

Leu Asp Phe Ser Thr Pro Gly Arg Ala Ala Ala Val Ala Phe Leu
                85                  90                  95

Ser Phe Ile Lys Asp Lys Trp Ser Glu Glu Thr His Leu Ser Gly Gly
            100                 105                 110

Tyr Leu Leu Asp Phe Leu Ala Met His Leu Trp Arg Ala Val Val Arg
        115                 120                 125

His Lys Asn Arg Leu Leu Leu Ser Ser Val Arg Pro Ala Ile Ile
130                 135                 140

Pro Thr Glu Glu Gln Gln Gln Gln Glu Glu Ala Arg Arg Arg Arg
145                 150                 155                 160

Gln Glu Gln Ser Pro Trp Asn Pro Arg Ala Gly Leu Asp Pro Arg Glu
            165                 170                 175
```

<210> SEQ ID NO 3
<211> LENGTH: 35938
<212> TYPE: DNA
<213> ORGANISM: Human adenovirus 5

<400> SEQUENCE: 3

```
catcatcaat aatatacctt attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgttttg      180
gtgtgcgccg gtgtacacag gaagtgacaa ttttcgcgcg gttttaggcg gatgttgtag     240
taaatttggg cgtaaccgag taagatttgg ccattttcgc gggaaaactg aataagagga     300
agtgaaatct gaataatttt gtgttactca tagcgcgtaa tatttgtcta gggccgcggg     360
gactttgacc gtttacgtgg agactcgccc aggtgttttt ctcaggtgtt ttccgcgttc     420
cgggtcaaag ttggcgtttt attattatag tcagctgacg tgtagtgtat ttatacccgg     480
tgagttcctc aagaggccac tcttgagtgc cagcgagtag agttttctcc tccgagccgc     540
tccgacaccg ggactgaaaa tgagacatat tatctgccac ggaggtgtta ttaccgaaga     600
aatggccgcc agtcttttgg accagctgat cgaagaggta ctggctgata atcttccacc     660
tcctagccat tttgaaccac ctaccttca cgaactgtat gatttagacg tgacggcccc     720
cgaagatccc aacgaggagg cggtttcgca gatttttccc gactctgtaa tgttggcggt     780
gcaggaaggg attgacttac tcactttttcc gccggcgccc ggttctccgg agccgcctca     840
ccttttcccgg cagcccgagc agccggagca gagagccttg gtccggtttt ctatgccaaa     900
ccttgtaccg gaggtgatcg atcttacctg ccacgaggct ggcttccacc ccagtgacga     960
cgaggatgaa gagggtgagg agtttgtgtt agattatgtg gagcaccccg gcacgttg     1020
caggtcttgt cattatcacc ggaggaatac gggggaccca gatattatgt gttcgctttg    1080
```

```
ctatatgagg acctgtggca tgtttgtcta cagtaagtga aaattatggg cagtgggtga    1140
tagagtggtg ggtttggtgt ggtaatttt tttttaattt ttacagtttt gtggtttaaa     1200
gaattttgta ttgtgatttt tttaaaaggt cctgtgtctg aacctgagcc tgagcccgag    1260
ccagaaccgg agcctgcaag acctacccgc cgtcctaaaa tggcgcctgc tatcctgaga    1320
cgcccgacat cacctgtgtc tagagaatgc aatagtagta cggatagctg tgactccggt    1380
ccttctaaca cacctcctga gatacacccg gtggtcccgc tgtgccccat taaaccagtt    1440
gccgtgagag ttggtgggcg tcgccaggct gtggaatgta tcgaggactt gcttaacgag    1500
cctgggcaac ctttggactt gagctgtaaa cgccccaggc cataaggtgt aaacctgtga    1560
ttgcgtgtgt ggttaacgcc tttgtttgct gaatgagttg atgtaagttt aataaagggt    1620
gagataatgt ttaacttgca tggcgtgtta aatggggcgg ggcttaaagg gtatataatg    1680
cgccgtgggc taatcttggt tacatctgac ctcatggagg cttgggagtg tttggaagat    1740
ttttctgctg tgcgtaactt gctggaacag agctctaaca gtacctcttg gttttggagg    1800
tttctgtggg gctcatccca ggcaaagtta gtctgcagaa ttaaggagga ttacaagtgg    1860
gaatttgaag agcttttgaa atcctgtggt gagctgtttg attctttgaa tctgggtcac    1920
caggcgcttt tccaagagaa ggtcatcaag actttggatt tttccacacc ggggcgcgct    1980
gcggctgctg ttgcttttt gagttttata aaggataaat ggagcgaaga aacccatctg     2040
agcgggggt acctgctgga ttttctggcc atgcatctgt ggagagcggt tgtgagacac      2100
aagaatcgcc tgctactgtt gtcttccgtc cgcccggcga taataccgac ggaggagcag    2160
cagcagcagc aggaggaagc caggcggcgg cggcaggagc agagcccatg gaacccgaga    2220
gccggcctgg accctcggga atgaatgttg tacaggtggc tgaactgtat ccagaactga    2280
gacgcatttt gacaattaca gaggatgggc aggggctaaa gggggtaaag agggagcggg    2340
gggcttgtga ggctacagag gaggctagga atctagcttt tagcttaatg accagacacc    2400
gtcctgagtg tattacttt caacagatca aggataattg cgctaatgag cttgatctgc     2460
tggcgcagaa gtattccata gagcagctga ccacttactg gctgcagcca ggggatgatt    2520
ttgaggaggc tattagggta tatgcaaagg tggcacttag gccagattgc aagtacaaga    2580
tcagcaaaact tgtaaatatc aggaattgtt gctacatttc tgggaacggg gccgaggtgg   2640
agatagatac ggaggatagg gtggccttta gatgtagcat gataaatatg tggccggggg    2700
tgcttggcat ggacggggtg gttattatga atgtaaggtt tactggcccc aattttagcg    2760
gtacggtttt cctggccaat accaacctta tcctacacgg tgtaagcttc tatgggttta    2820
acaatacctg tgtggaagcc tggaccgatg taagggttcg gggctgtgcc ttttactgct    2880
gctggaaggg ggtggtgtgt cgccccaaaa gcagggcttc aattaagaaa tgcctctttg    2940
aaaggtgtac cttgggtatc ctgtctgagg gtaactccag ggtgcgccac aatgtggcct    3000
ccgactgtgg ttgcttcatg ctagtgaaaa gcgtggctgt gattaagcat aacatggtat    3060
gtggcaactg cgaggacagg gcctctcaga tgctgacctg ctcggacggc aactgtcacc    3120
tgctgaagac cattcacgta gccagccact ctcgcaaggc ctggccagtg tttgagcata    3180
acatactgac ccgctgttcc ttgcatttgg gtaacaggag gggggtgttc ctaccttacc    3240
aatgcaattt gagtcacact aagatattgc ttgagcccga gagcatgtcc aaggtgaacc    3300
tgaacggggt gtttgacatg accatgaaga tctggaaggt gctgaggtac gatgagaccc    3360
gcaccaggtg cagaccctgc gagtgtgtcg gtaaacatat taggaaccag cctgtgatgc    3420
tggatgtgac cgaggagctg aggcccgatc acttggtgct ggcctgcacc cgcgctgagt    3480
```

```
ttggctctag cgatgaagat acagattgag gtactgaaat gtgtgggcgt ggcttaaggg    3540
tgggaaagaa tatataaggt gggggtctta tgtagttttg tatctgtttt gcagcagccg    3600
ccgccgccat gagcaccaac tcgtttgatg gaagcattgt gagctcatat ttgacaacgc    3660
gcatgccccc atgggccggg gtgcgtcaga atgtgatggg ctccagcatt gatggtcgcc    3720
ccgtcctgcc cgcaaactct actaccttga cctacgagac cgtgtctgga acgccgttgg    3780
agactgcagc ctccgccgcc gcttcagccg ctgcagccac cgcccgcggg attgtgactg    3840
actttgcttt cctgagcccg cttgcaagca gtgcagcttc ccgttcatcc gcccgcgatg    3900
acaagttgac ggctcttttg gcacaattgg attctttgac ccgggaactt aatgtcgttt    3960
ctcagcagct gttggatctg cgccagcagg tttctgccct gaaggcttcc tcccctccca    4020
atgcggttta aaacataaat aaaaaaccag actctgtttg gatttggatc aagcaagtgt    4080
cttgctgtct ttatttaggg gttttgcgcg cgcggtaggc ccgggaccag cggtctcggt    4140
cgttgagggt cctgtgtatt ttttccagga cgtggtaaag gtgactctgg atgttcagat    4200
acatgggcat aagcccgtct ctggggtgga ggtagcacca ctgcagagct tcatgctgcg    4260
gggtggtgtt gtagatgatc cagtcgtagc aggagcgctg ggcgtggtgc ctaaaaatgt    4320 cttttcagtag caagctgatt gccaggggca ggcccttggt gtaagtgttt acaaagcggt    4380
taagctggga tgggtgcata cgtggggata tgagatgcat cttggactgt attttttaggt   4440 tggctatgtt cccagccata tccctccggg gattcatgtt gtgcagaacc accagcacag    4500
tgtatccggt gcacttggga aatttgtcat gtagcttaga aggaaatgcg tggaagaact    4560
tggagacgcc cttgtgacct ccaagatttt ccatgcattc gtccataatg atggcaatgg    4620
gcccacgggc ggcggcctgg gcgaagatat ttctgggatc actaacgtca tagttgtgtt    4680
ccaggatgag atcgtcatag gccatttta caaagcgcgg gcggagggtg ccagactgcg    4740
gtataatggt tccatccggc ccaggggcgt agttaccctc acagatttgc atttcccacg    4800 cttttgagttc agatgggggg atcatgtcta cctgcggggc gatgaagaaa acggtttccg    4860
gggtagggga gatcagctgg gaagaaagca ggttcctgag cagctgcgac ttaccgcagc    4920
cggtgggccc gtaaatcaca cctattaccg ggtgcaactg gtagttaaga gagctgcagc    4980
tgccgtcatc cctgagcagg ggggccactt cgttaagcat gtccctgact cgcatgtttt    5040
ccctgaccaa atccgccaga aggcgctcgc cgcccagcga tagcagttct tgcaaggaag    5100
caaagttttt caacggtttg agaccgtccg ccgtaggcat gcttttgagc gtttgaccaa    5160
gcagttccag gcggtccac agctcggtca cctgctctac ggcatctcga tccagcatat    5220
ctcctcgttt cgcgggttgg ggcggctttc gctgtacggc agtagtcggt gctcgtccag    5280
acgggccagg gtcatgtctt tccacggggcg cagggtcctc gtcagcgtag tctgggtcac    5340
ggtgaagggg tgcgctccgg gctgcgcgct ggccagggtg cgcttgaggc tggtcctgct    5400
ggtgctgaag cgctgccggt cttcgccctg cgcgtcggcc aggtagcatt tgaccatggt    5460
gtcatagtcc agcccctccg cggcgtggcc cttggcgcgc agcttgccct ggaggaggc     5520 gccgcacgag gggcagtgca gacttttgag ggcgtagagc ttgggcgcga gaaataccga    5580
ttccggggag taggcatccg cgccgcaggc cccgcagacg gtctcgcatt ccacgagcca    5640
ggtgagctct ggccgttcgg ggtcaaaaac caggtttccc ccatgctttt tgatgcgttt    5700
cttacctctg gtttccatga gccggtgtcc acgctcggtg acgaaaaggc tgtccgtgtc    5760
cccgtataca gacttgagag gcctgtcctc gagcggtgtt ccgcggtcct cctcgtatag    5820
aaactcggac cactctgaga caaaggctcg cgtccaggcc agcacgaagg aggctaagtg    5880
```

```
ggaggggtag cggtcgttgt ccactagggg gtccactcgc tccagggtgt gaagacacat    5940
gtcgccctct tcggcatcaa ggaaggtgat tggtttgtag gtgtaggcca cgtgaccggg    6000
tgttcctgaa ggggggctat aaaggggg t ggggg cgcgt tcgtcctcac tctcttccgc    6060
atcgctgtct gcgagggcca gctgttgggg tgagtactcc ctctgaaaag cgggcatgac    6120
ttctgcgcta agattgtcag tttccaaaaa cgaggaggat ttgatattca cctggcccgc    6180
ggtgatgcct ttgagggtgg ccgcatccat ctggtcagaa aagacaatct tttgttgtc     6240
aagcttggtg gcaaacgacc cgtagagggc gttggacagc aacttggcga tggagcgcag    6300
ggtttggttt ttgtcgcgat cggcgcgctc cttggccgcg atgtttagct gcacgtattc    6360
gcgcgcaacg caccgccatt cgggaaagac ggtggtgcgc tcgtcgggca ccaggtgcac    6420
gcgccaaccg cggttgtgca gggtgacaag gtcaacgctg gtggctacct ctccgcgtag    6480
gcgctcgttg gtccagcaga ggcggccgcc cttgcgcgag cagaatggcg gtagggggtc    6540
tagctgcgtc tcgtccgggg ggtctgcgtc cacggtaaag accccgggca gcaggcgcgc    6600
gtcgaagtag tctatcttgc atccttgcaa gtctagcgcc tgctgccatg cgcgggcggc    6660
aagcgcgcgc tcgtatgggt tgagtggggg accccatggc atgggg tggg tgagcgcgga    6720
ggcgtacatg ccgcaaatgt cgtaaacgta gaggggctct ctgagtattc caagatatgt    6780
agggtagcat cttccaccgc ggatgctggc gcgcacgtaa tcgtatagtt cgtgcgaggg    6840
agcgaggagg tcgggaccga ggttgctacg ggcgggctgc tctgctcgga agactatctg    6900
cctgaagatg gcatgtgagt tggatgatat ggttggacgc tggaagacgt gaagctggc     6960
gtctgtgaga cctaccgcgt cacgcacgaa ggaggcgtag gagtcgcgca gcttgttgac    7020
cagctcggcg gtgacctgca cgtctagggc gcagtagtcc agggtttcct tgatgatgtc    7080
atacttatcc tgtccctttt ttttccacag ctcgcggttg aggacaaact cttcgcggtc    7140
tttccagtac tcttggatcg gaaacccgtc ggcctccgaa cggtaagagc ctagcatgta    7200
gaactggttg acgcctggt aggcgcagca tccctttcct acgggtagcg cgtatgcctg     7260
cgcggccttc cggagcgagg tgtgggtgag cgcaaaggtg tccctgacca tgactttgag    7320
gtactggtat ttgaagtcag tgtcgtcgca tccgccctgc tcccagagca aaaagtccgt    7380
gcgcttttg gaacgcggat ttggcagggc gaaggtgaca tcgttgaaga gtatctttcc     7440
cgcgcgaggc ataaagttgc gtgtgatgcg gaagggtccc ggcacctcgg aacgttgtt     7500
aattacctgg gcggcgagca cgatctcgtc aaagccgttg atgttgtggc ccacaatgta    7560
aagttccaag aagcgcggga tgcccttgat ggaaggcaat ttttaagtt cctcgtaggt     7620
gagctcttca ggggagctga gcccgtgctc tgaaagggcc cagtctgcaa gatgagggtt    7680
ggaagcgacg aatgagctcc acaggtcacg ggccattagc atttgcaggt ggtcgcgaaa    7740
ggtcctaaac tggcgaccta tggccatttt ttctggggtg atgcagtaga aggtaagcgg    7800
gtcttgttcc cagcggtccc atccaaggtt cgcggctagg tctcgcgcgg cagtcactag    7860
aggctcatct ccgccgaact tcatgaccag catgaagggc acgagctgct tcccaaaggc    7920
ccccatccaa gtataggtct ctacatcgta ggtgacaaag agacgctcgg tgcgaggatg    7980
cgagccgatc gggaagaact ggatctcccg ccaccaattg gaggagtggc tattgatgtg    8040
gtgaaagtag aagtccctgc gacgggccga acactcgtgc tggcttttgt aaaaacgtgc    8100
gcagtactgg cagcggtgca cgggctgtac atcctgcacg aggttgacct gacgaccgcg    8160
cacaaggaag cagagtggga atttgagccc ctcgcctggc gggtttggct ggtggtcttc    8220
tacttcggct gcttgtcctt gaccgtctgg ctgctcgagg ggagttacgg tggatcggac    8280
```

```
caccacgccg cgcgagccca aagtccagat gtccgcgcgc ggcggtcgga gcttgatgac   8340
aacatcgcgc agatgggagc tgtccatggt ctggagctcc cgcggcgtca ggtcaggcgg   8400
gagctcctgc aggtttacct cgcatagacg ggtcagggcg cgggctagat ccaggtgata   8460
cctaatttcc aggggctggt tggtggcggg gtcgatggct tgcaagaggc cgcatccccg   8520
cggcgcgact acggtaccgc gcggcgggcg gtgggccgcg ggggtgtcct tggatgatgc   8580
atctaaaagc ggtgacgcgg gcgagccccc ggaggtaggg ggggctccgg acccgccggg   8640 agaggggggca ggggcacgtc ggcgccgcgc gcgggcagga gctggtgctg cgcgcgtagg   8700
ttgctggcga acgcgacgac gcggcggttg atctcctgaa tctggcgcct ctgcgtgaag   8760
acgacgggcc cggtgagctt gagcctgaaa gagagttcga cagaatcaat ttcggtgtcg   8820 ttgacgcgg cctggcgcaa aatctcctgc acgtctcctg agttgtcttg ataggcgatc   8880
tcggccatga actgctcgat ctcttcctcc tggagatctc cgcgtccggc tcgctccacg   8940
gtggcggcga gtcgttgga aatgcggcc atgagctgcg agaaggcgtt gaggcctccc   9000
tcgttccaga cgcggctgta gaccacgccc ccttcggcat cgcgggcgcg catgaccacc   9060
tgcgcgagat tgagctccac gtgccgggcg aagacggcgt agtttcgcag gcgctgaaag   9120
aggtagttga gggtggtggc ggtgtgttct gccacgaaga agtacataac ccagcgtcgc   9180
aacgtggatt cgttgatatc ccccaaggcc tcaaggcgct ccatggcctc gtagaagtcc   9240
acggcgaagt tgaaaactg ggagttgcgc gccgacacgg ttaactcctc ctccagaaga   9300
cggatgagct cggcgacagt gtcgcgcacc tcgcgctcaa aggctacagg ggcctcttct   9360
tcttcttcaa tctcctcttc cataaggcc tccccttctt cttcttctgg cggcggtggg   9420 ggaggggga cacggcggcg acgacggcgc accgggaggc ggtcgacaaa gcgctcgatc   9480
atctccccgc ggcgacggcg catggtctcg gtgacgcgc ggccgttctc gcgggggcgc   9540
agttggaaga cgccgcccgt catgtcccgg ttatgggttg gcgggggct gccatgcggc   9600 agggatacgg cgctaacgat gcatctcaac aattgttgtg taggtactcc gccgccgagg   9660
gacctgagcg agtccgcatc gaccggatcg gaaaacctct cgagaaaggc gtctaaccag   9720
tcacagtcgc aaggtaggct gagcaccgtg gcgggcggca gcgggcggcg gtcggggttg   9780
tttctggcgg aggtgctgct gatgatgtaa ttaaagtagg cggtcttgag acggcggatg   9840
gtcgacagaa gcaccatgtc cttgggtccg gcctgctgaa tgcgcaggcg gtcggccatg   9900
ccccaggctt cgttttgaca tcggcgcagg tctttgtagt agtcttgcat gagcctttct   9960
accggcactt cttcttctcc ttcctcttgt cctgcatctc ttgcatctat cgctgcggcg  10020
gcggcggagt ttggccgtag gtggcgccct cttcctccca tgcgtgtgac cccgaagccc  10080
ctcatcggct gaagcagggc taggtcgcg acaacgcgct cggctaatat ggcctgctgc  10140
acctgcgtga gggtagactg gaagtcatcc atgtccacaa agcggtggta tgcgcccgtg  10200
ttgatggtgt aagtgcagtt ggccataacg gaccagttaa cggtctggtg acccggctgc  10260
gagagctcgg tgtacctgag acgcgagtaa gccctcgagt caaatacgta gtcgttgcaa  10320
gtccgcacca ggtactggta tcccaccaaa aagtgcggcg gcggctggcg gtagaggggc  10380
cagcgtaggg tggccggggc tccggggcg agatcttcca acataaggcg atgatatccg  10440
tagatgtacc tggacatcca ggtgatgccg gcggcggtgg tggaggcgcg cggaaagtcg  10500
cggacgcggt tccagatgtt gcgcagcggc aaaaagtgct ccatggtcgg gacgctctgg  10560
ccggtcaggc gcgcgcaatc gttgacgctc tagaccgtgc aaaaggagag cctgtaagcg  10620
ggcactcttc cgtggtctgg tggataaatt cgcaagggta tcatggcgga cgaccggggt  10680
```

```
tcgagccccg tatccggccg tccgccgtga tccatgcggt taccgcccgc gtgtcgaacc    10740
caggtgtgcg acgtcagaca acgggggagt gctccttttg gcttccttcc aggcgcggcg    10800
gctgctgcgc tagcttttt ggccactggc cgcgcgcagc gtaagcggtt aggctggaaa    10860
gcgaaagcat taagtggctc gctccctgta gccggagggt tattttccaa gggttgagtc    10920
gcgggacccc cggttcgagt ctcggaccgg ccggactgcg gcgaacgggg gtttgcctcc    10980
ccgtcatgca agaccccgct tgcaaattcc tccggaaaca gggacgagcc cctttttgc    11040 tttccccaga tgcatccggt gctgcggcag atgcgccccc ctcctcagca gcggcaagag    11100
caagagcagc ggcagacatg cagggcaccc tccctcctc ctaccgcgtc aggagggcg     11160 acatccgcgg ttgacgcggc agcagatggt gattacgaac ccccgcggcg ccgggcccgg    11220
cactacctgg acttggagga gggcgagggc ctggcgcggc taggagcgcc ctctcctgag    11280
cggtacccaa gggtgcagct gaagcgtgat acgcgtgagg cgtacgtgcc gcggcagaac    11340
ctgtttcgcg accgcgaggg agaggagccc gaggagatgc gggatcgaaa gttccacgca    11400
gggcgcgagc tgcggcatgg cctgaatcgc gagcggttgc tgcgcgagga ggactttgag    11460
cccgacgcgc gaaccgggat tagtcccgcg cgcgcacacg tggcggccgc cgacctggta    11520
accgcatacg agcagacggt gaaccaggag attaactttc aaaaaagctt taacaaccac    11580
gtgcgtacgc ttgtggcgcg cgaggaggtg gctataggac tgatgcatct gtgggacttt    11640
gtaagcgcgc tggagcaaaa cccaaatagc aagccgctca tggcgcagct gttccttata    11700
gtgcagcaca gcagggacaa cgaggcattc agggatgcgc tgctaaacat agtagagccc    11760
gagggccgct ggctgctcga tttgataaac atcctgcaga gcatagtggt gcaggagcgc    11820
agcttgagcc tggctgacaa ggtggccgcc atcaactatt ccatgcttag cctgggcaag    11880
ttttacgccc gcaagatata ccataccccct tacgttccca tagacaagga ggtaaagatc    11940 gagggggttct acatgcgcat ggcgctgaag gtgcttacct tgagcgacga cctgggcgtt    12000
tatcgcaacg agcgcatcca caaggccgtg agcgtgagcc ggcggcgcga gctcagcgac    12060
cgcgagctga tgcacagcct gcaaagggcc ctggctggca cgggcagcgg cgatagagag    12120
gccgagtcct actttgacgc gggcgctgac ctgcgctggg ccccaagccg acgcgccctg    12180
gaggcagctg gggccggacc tgggctggcg gtggcacccg cgcgcgctgg caacgtcggc    12240
ggcgtggagg aatatgacga ggacgatgag tacgagccag aggacggcga gtactaagcg    12300
gtgatgtttc tgatcagatg atgcaagacg caacggaccc ggcggtgcgg gcggcgctgc    12360
agagccagcc gtccggcctt aactccacgg acgactggcg ccaggtcatg gaccgcatca    12420
tgtcgctgac tgcgcgcaat cctgacgcgt tccggcagca gccgcaggcc aaccggctct    12480
ccgcaattct ggaagcggtg gtcccggcgc gcgcaaaccc cacgcacgag aaggtgctgg    12540
cgatcgtaaa cgcgctggcc gaaaacaggg ccatccggcc cgacgaggcc ggcctggtct    12600
acgacgcgct gcttcagcgc gtggctcgtt acaacagcgg caacgtgcag accaacctgg    12660
accggctggt gggggatgtg cgcgaggccg tggcgcagcg tgagcgcgcg cagcagcagg    12720
gcaacctggg ctccatggtt gcactaaacg ccttcctgag tacacagccc gccaacgtgc    12780
cgcggggaca ggaggactac accaactttg tgagcgcact gcggctaatg gtgactgaga    12840
caccgcaaag tgaggtgtac cagtctgggc cagactattt tttccagacc agtagacaag    12900
gcctgcagac cgtaaacctg agccaggctt tcaaaaactt gcaggggctg tgggggtgc    12960 gggctcccac aggcgaccgc gcgaccgtgt ctagcttgct gacgcccaac tcgcgcctgt    13020
tgctgctgct aatagcgccc ttcacggaca gtggcagcgt gtcccgggac acatacctag    13080
```

-continued

```
gtcacttgct gacactgtac cgcgaggcca taggtcaggc gcatgtggac gagcatactt    13140
tccaggagat tacaagtgtc agccgcgcgc tggggcagga ggacacgggc agcctggagg    13200
caaccctaaa ctacctgctg accaaccggc ggcagaagat ccccctcgttg cacagtttaa    13260
acagcgagga ggagcgcatt ttgcgctacg tgcagcagag cgtgagcctt aacctgatgc    13320
gcgacgggt aacgcccagc gtggcgctgg acatgaccgc gcgcaacatg gaaccgggca    13380
tgtatgcctc aaaccggccg tttatcaacc gcctaatgga ctacttgcat cgcgcggccg    13440
ccgtgaaccc cgagtatttc accaatgcca tcttgaaccc gcactggcta ccgcccctg    13500
gtttctacac cggggattc gaggtgcccg agggtaacga tggattcctc tgggacgaca    13560
tagacgacag cgtgttttcc ccgcaaccgc agaccctgct agagttgcaa cagcgcgagc    13620
aggcagaggc ggcgctgcga aaggaaagct tccgcaggcc aagcagcttg tccgatctag    13680
gcgctgcggc cccgcggtca gatgctagta gcccatttcc aagcttgata gggtctctta    13740
ccagcactcg caccacccgc ccgcgcctgc tgggcgagga ggagtaccta aacaactcgc    13800
tgctgcagcc gcagcgcgaa aaaaacctgc ctccggcatt tcccaacaac gggatagaga    13860
gcctagtgga caagatgagt agatggaaga cgtacgcgca ggagcacagg gacgtgccag    13920
gccccgcgccc cccacccgt cgtcaaaggc acgaccgtca gcggggtctg gtgtgggagg    13980
acgatgactc ggcagacgac agcagcgtcc tggatttggg agggagtggc aacccgtttg    14040
cgcaccttcg ccccaggctg gggagaatgt tttaaaaaaa aaaagcatg atgcaaaata    14100
aaaaactcac caaggccatg gcaccgagcg ttggtttct tgtattcccc ttagtatgcg    14160
gcgcgcggcg atgtatgagg aaggtcctcc tccctcctac gagagtgtgg tgagcgcggc    14220
gccagtggcg gcggcgctgg gttctcccctt cgatgctccc ctggaccgc cgtttgtgcc    14280
tccgcggtac ctgcgcccta ccgggggag aaacagcatc cgttactctg agttggcacc    14340
cctattcgac accacccgtg tgtacctggt ggacaacaag tcaacggatg tggcatccct    14400
gaactaccag aacgaccaca gcaactttct gaccacggtc attcaaaaca atgactacag    14460
cccgggggag gcaagcacac agaccatcaa tcttgacgac cggtcgcact ggggcggcga    14520
cctgaaaacc atcctgcata ccaacatgcc aaatgtgaac gagttcatgt ttaccaataa    14580
gtttaaggcg cgggtgatgg tgtcgcgctt gcctactaag gacaatcagg tggagctgaa    14640
atacgagtgg gtggagttca cgctgcccga gggcaactac tccgagacca tgaccataga    14700
ccttatgaac aacgcgatcg tggagcacta cttgaaagtg gcagacagaa cggggttct    14760
ggaaagcgac atcggggtaa agtttgacac ccgcaacttc agactggggt ttgaccccgt    14820
cactggtctt gtcatgcctg ggtatatac aaacgaagcc ttccatccag acatcatttt    14880
gctgccagga tgcggggtgg acttcaccca cagccgcctg agcaacttgt tgggcatccg    14940
caagcggcaa cccttccagg agggctttag gatcacctac gatgatctgg agggtggtaa    15000
cattcccgca ctgttggatg tggacgccta ccaggcgagc ttgaaagatg acaccgaaca    15060
gggcggggt ggcgcaggcg gcagcaacag cagtggcagc ggcgcggaag agaactccaa    15120
cgcggcagcc gcggcaatgc agccggtgga ggacatgaac gatcatgcca ttcgcggcga    15180
cacctttgcc acacgggctg aggagaagcg cgctgaggcc gaagcagcgg ccgaagctgc    15240
cgcccccgct gcgcaacccg aggtcgagaa gcctcagaag aaaccggtga tcaaacccct    15300
gacagaggac agcaagaaac gcagttacaa cctaataagc aatgacagca ccttcacccaa   15360
gtaccgcagc tggtaccttg catacaacta cggcgaccct cagaccggaa tccgctcatg    15420
gaccctgctt tgcactcctg acgtaacctg cggctcggag caggtctact ggtcgttgcc    15480
```

```
agacatgatg caagacccog tgaccttccg ctccacgcgc cagatcagca actttccggt   15540
ggtgggcgcc gagctgttgc ccgtgcactc caagagcttc tacaacgacc aggccgtcta   15600
ctcccaactc atccgccagt ttacctctct gacccacgtg ttcaatcgct ttcccgagaa   15660
ccagattttg gcgcgcccgc cagccccac catcaccacc gtcagtgaaa acgttcctgc    15720
tctcacagat cacgggacgc taccgctgcg caacagcatc ggaggagtcc agcgagtgac   15780
cattactgac gccagacgcc gcacctgccc ctacgtttac aaggccctgg gcatagtctc   15840
gccgcgcgtc ctatcgagcc gcacttttttg agcaagcatg tccatcctta tatcgcccag  15900
caataacaca ggctgggggcc tgcgcttccc aagcaagatg tttggcgggg ccaagaagcg  15960
ctccgaccaa cacccagtgc gcgtgcgcgg gcactaccgc gcgccctggg gcgcgcacaa   16020
acgcggccgc actgggcgca ccaccgtcga tgacgccatc gacgcggtgg tggaggaggc   16080
gcgcaactac acgcccacgc cgccaccagt gtccacagtg gacgcggcca ttcagaccgt   16140
ggtgcgcgga gcccggcgct atgctaaaat gaagagacgg cggaggcgcg tagcacgtcg   16200
ccaccgccgc cgacccggca ctgccgccca acgcgcggcg gcgccctgc ttaaccgcgc    16260 acgtcgcacc ggccgacggg cggccatgcg ggccgctcga aggctggccg cgggtattgt   16320
cactgtgccc cccaggtcca ggcgacgagc ggccgccgca gcagccgcgg ccattagtgc   16380
tatgactcag ggtcgcaggg gcaacgtgta ttgggtgcgc gactcggtta gcggcctgcg   16440 cgtgccgtg cgcacccgcc cccgcgcaa ctagattgca agaaaaact acttagactc      16500 gtactgttgt atgtatccag cggcggcggc gcgcaacgaa gctatgtcca agcgcaaaat   16560
caaagaagag atgctccagg tcatcgcgcc ggagatctat ggcccccga agaaggaaga    16620 gcaggattac aagccccgaa agctaaagcg ggtcaaaaag aaaagaaag atgatgatga    16680 tgaacttgac gacgaggtgg aactgctgca cgctaccgcg cccaggcgac gggtacagtg   16740
gaaaggtcga cgcgtaaaac gtgttttgcg acccggcacc accgtagtct ttacgcccgg   16800
tgagcgctcc acccgcacct acaagcgcgt gtatgatgag gtgtacggcg acgaggacct   16860
gcttgagcag gccaacgagc gcctcgggga gtttgcctac ggaaagcggc ataaggacat   16920
gctggcgttg ccgctggacg agggcaaccc aacacctagc ctaaagcccg taacactgca   16980
gcaggtgctg cccgcgcttg caccgtccga agaaaagcgc ggcctaaagc gcgagtctgg   17040
tgacttggca cccaccgtgc agctgatggt acccaagcgc cagcgactgg aagatgtctt   17100
ggaaaaaatg accgtggaac ctgggctgga gcccgaggtc cgcgtgcggc caatcaagca   17160
ggtggcgccg ggactgggcg tgcagaccgt ggacgttcag ataccgacta ccagtagcac   17220
cagtattgcc accgccacag agggcatgga gacacaaacg tccccggttg cctcagcggt   17280
ggcggatgcc gcggtgcagg cggtcgctgc ggccgcgtcc aagacctcta cggaggtgca   17340
aacggacccg tggatgtttc gcgtttcagc ccccgggcgc ccgcgcggtt cgaggaagta   17400
cggcgccgcc agcgcgctac tgcccgaata tgccctacat ccttccattg cgcctacccc   17460
cggctatcgt ggctacacct accgcccag aagacgagca actacccgac gccgaaccac    17520
cactggaacc cgccgccgcc gtcgccgtcg ccagcccgtg ctggccccga tttccgtgcg   17580
cagggtggct cgcgaaggag gcaggaccct ggtgctgcca acagcgcgct accacccag    17640 catcgtttaa aagccggtct ttgtggttct tgcagatatg gccctcacct gccgcctccg   17700
tttcccggtg ccgggattcc gaggaagaat gcaccgtagg aggggcatgg ccggccacgg   17760
cctgacgggc ggcatgcgtc gtgcgcacca ccggcggcgg cgcgcgtcgc accgtcgcat   17820
gcgcggcggt atcctgcccc tccttattcc actgatcgcc gcggcgattg gcgccgtgcc   17880
```

```
cggaattgca tccgtggcct tgcaggcgca gagacactga ttaaaaacaa gttgcatgtg   17940
gaaaaatcaa aataaaaagt ctggactctc acgctcgctt ggtcctgtaa ctattttgta   18000
gaatggaaga catcaacttt gcgtctctgg ccccgcgaca cggctcgcgc ccgttcatgg   18060
gaaactggca agatatcggc accagcaata tgagcggtgg cgccttcagc tggggctcgc   18120
tgtggagcgg cattaaaaat ttcggttcca ccgttaagaa ctatggcagc aaggcctgga   18180
acagcagcac aggccagatg ctgagggata agttgaaaga gcaaaatttc aacaaaagg    18240 tggtagatgg cctggcctct ggcattagcg gggtggtgga cctggccaac caggcagtgc   18300
aaaataagat taacagtaag cttgatcccc gccctcccgt agaggagcct ccaccggccg   18360
tggagacagt gtctccagag gggcgtggcg aaaagcgtcc gcgccccgac agggaagaaa   18420
ctctggtgac gcaaatagac gagcctccct cgtacgagga ggcactaaag caaggcctgc   18480
ccaccacccg tcccatcgcg cccatggcta ccggagtgct gggccagcac acacccgtaa   18540
cgctggacct gcctcccccc gccgacaccc agcagaaacc tgtgctgcca ggcccgaccg   18600
ccgttgttgt aacccgtcct agccgcgcgt ccctgcgccg cgccgccagc ggtccgcgat   18660
cgttgcggcc cgtagccagt ggcaactggc aaagcacact gaacagcatc gtgggtctgg   18720
gggtgcaatc cctgaagcgc cgacgatgct tctgaatagc taacgtgtcg tatgtgtgtc   18780
atgtatgcgt ccatgtcgcc gccagaggag ctgctgagcc gccgcgcgcc cgctttccaa   18840
gatggctacc ccttcgatga tgccgcagtg gtcttacatg cacatctcgg ccaggacgc    18900 ctcggagtac ctgagccccg ggctggtgca gtttgcccgc gccaccgaga cgtacttcag   18960
cctgaataac aagtttagaa accccacggt ggcgcctacg cacgacgtga ccacagaccg   19020
gtcccagcgt ttgacgctgc ggttcatccc tgtggaccgt gaggatactg cgtactcgta   19080
caaggcgcgg ttcaccctag ctgtgggtga taaccgtgtg ctggacatgg cttccacgta   19140 cttgacatc cgcggcgtgc tggacagggg ccctactttt aagccctact ctggcactgc    19200
ctacaacgcc ctggctccca agggtgcccc aaatccttgc gaatgggatg aagctgctac   19260
tgctcttgaa ataaacctag aagaagagga cgatgacaac gaagacgaag tagacgagca   19320
agctgagcag caaaaaactc acgtatttgg gcaggcgcct tattctggta taaatattac   19380
aaaggagggt attcaaatag gtgtcgaagg tcaaacacct aaatatgccg ataaaacatt   19440
tcaacctgaa cctcaaatag agaatctca gtggtacgaa actgaaatta atcatgcagc    19500
tgggagagtc cttaaaaaga ctacccccaat gaaaccatgt tacggttcat atgcaaaacc   19560
cacaaatgaa aatggagggc aaggcattct tgtaaagcaa caaaatggaa agctagaaag   19620
tcaagtggaa atgcaatttt tctcaactac tgaggcgacc gcaggcaatg gtgataactt   19680
gactcctaaa gtggtattgt acagtgaaga tgtagatata gaaacccag acactctat     19740 ttcttacatg cccactatta aggaaggtaa ctcacgagaa ctaatgggcc aacaatctat   19800
gcccaacagg cctaattaca ttgcttttag ggacaatttt attggtctaa tgtattacaa   19860
cagcacgggt aatatgggtg ttctggcggg ccaagcatcg cagttgaatg ctgttgtaga   19920
tttgcaagac agaaacacag agctttcata ccagcttttg cttgattcca ttggtgatag   19980
aaccaggtac ttttctatgt ggaatcaggc tgttgacagc tatgatccag atgttagaat   20040
tattgaaaat catggaactg aagatgaact tccaaattac tgctttccac tgggaggtgt   20100
gattaataca gagactctta ccaaggtaaa acctaaaaca ggtcaggaaa atggatggga   20160
aaaagatgct acagaatttt cagataaaaa tgaataaga gttggaaata attttgccat    20220
ggaaatcaat ctaaatgcca acctgtggag aaatttcctg tactccaaca tagcgctgta   20280
```

```
tttgcccgac aagctaaagt acagtccttc caacgtaaaa atttctgata acccaaacac   20340
ctacgactac atgaacaagc gagtggtggc tcccgggtta gtggactgct acattaacct   20400
tggagcacgc tggtcccttg actatatgga caacgtcaac ccatttaacc accaccgcaa   20460
tgctggcctg cgctaccgct caatgttgct gggcaatggt cgctatgtgc ccttccacat   20520
ccaggtgcct cagaagttct tgccattaa aaacctcctt ctcctgccgg gctcatacac    20580
ctacgagtgg aacttcagga aggatgttaa catggttctg cagagctccc taggaaatga   20640
cctaagggtt gacggagcca gcattaagtt tgatagcatt tgcctttacg ccaccttctt   20700
ccccatggcc cacaacaccg cctccacgct gaggccatg cttagaaacg acaccaacga    20760
ccagtccttt aacgactatc tctccgccgc caacatgctc taccctatac ccgccaacgc   20820
taccaacgtg cccatatcca tccctcccg caactgggcg ctttccgcg ctgggccctt     20880
cacgcgcctt aagactaagg aaaccccatc actgggctcg ggctacgacc cttattacac   20940
ctactctggc tctataccct acctagatgg aaccttttac ctcaaccaca cctttaagaa   21000
ggtggccatt acctttgact cttctgtcag ctggcctggc aatgaccgcc tgcttacccc   21060
caacgagttt gaaattaagc gctcagttga cggggagggt tacaacgttg cccagtgtaa   21120
catgaccaaa gactggttcc tggtacaaat gctagctaac tacaacattg ctaccaggg    21180
cttctatatc ccagagagct acaaggaccg catgtactcc ttctttagaa acttccagcc   21240
catgagccgt caggtggtgg atgatactaa atacaaggac taccaacagg tgggcatcct   21300
acaccaacac aacaactctg gatttgttgg ctaccttgcc cccaccatgc gcgaaggaca   21360
ggcctaccct gctaacttcc cctatccgct tataggcaag accgcagttg acagcattac   21420
ccagaaaag tttctttgcg atcgcaccct ttggcgcatc ccattctcca gtaactttat     21480
gtccatgggc gcactcacag acctgggcca aaaccttctc tacgccaact ccgcccacgc   21540
gctagacatg acttttgagg tggatcccat ggacgagccc acccttcttt atgttttgtt   21600
tgaagtcttt gacgtggtcc gtgtgcaccg gccgcaccgc ggcgtcatcg aaaccgtgta   21660
cctgcgcacg cccttctcgg ccggcaacgc cacaacataa agaagcaagc aacatcaaca   21720
acagctgccg ccatgggctc cagtgagcag gaactgaaag ccattgtcaa agatcttggt   21780
tgtgggccat atttttgggc cacctatgac aagcgctttc caggctttgt ttctccacac   21840
aagctcgcct cgccatagt caatacggcc ggtcgcgaga ctggggggcgt acactggatg    21900
gcctttgcct ggaacccgca ctcaaaaaca tgctacctct ttgagccctt tggcttttct   21960
gaccagcgac tcaagcaggt ttaccagttt gagtacgagt cactcctgcg ccgtagcgcc   22020
attgcttctt cccccgaccg ctgtataacg ctggaaaagt ccacccaaag cgtacagggg   22080
cccaactcgg ccgcctgtgg actattctgc tgcatgtttc tccacgcctt tgccaactgg   22140
ccccaaactc ccatggatca aaccccacc atgaaccta ttaccggggt acccaactcc      22200
atgctcaaca gtccccaggt acagcccacc ctgcgtcgca accaggaaca gctctacagc   22260
ttcctggagc gccactcgcc ctacttccgc agccacagtg cgcagattag gagcgccact   22320
tcttttttgtc acttgaaaaa catgtaaaaa taatgtacta gagacacttt caataaaggc   22380
aaatgctttt atttgtacac tctcgggtga ttatttaccc ccacccttgc cgtctgcgcc   22440
gtttaaaaat caagggggtt ctgccgcgca tcgctatgcg ccactggcag ggacacgttg   22500
cgatactggt gtttagtgct ccacttaaac tcaggcacaa ccatccgcgg cagctcggtg   22560
aagttttcac tccacaggct gcgcaccatc accaacgcgt ttagcaggtc gggcgccgat   22620
atcttgaagt cgcagttggg gcctccgccc tgcgcgcgcg agttgcgata cacagggttg   22680
```

```
cagcactgga acactatcag cgccgggtgg tgcacgctgg ccagcacgct cttgtcggag  22740
atcagatccg cgtccaggtc ctccgcgttg ctcagggcga acggagtcaa ctttggtagc  22800
tgccttccca aaaagggcgc gtgcccaggc tttgagttgc actcgcaccg tagtggcatc  22860
aaaaggtgac cgtgcccggt ctgggcgtta ggatacagcg cctgcataaa agccttgatc  22920
tgcttaaaag ccacctgagc ctttgcgcct tcagagaaga acatgccgca agacttgccg  22980
gaaaactgat tggccggaca ggccgcgtcg tgcacgcagc accttgcgtc ggtgttggag  23040
atctgcacca catttcggcc ccaccggttc ttcacgatct tggccttgct agactgctcc  23100
ttcagcgcgc gctgcccgtt ttcgctcgtc acatccattt caatcacgtg ctccttattt  23160
atcataatgc ttccgtgtag acacttaagc tcgccttcga tctcagcgca gcggtgcagc  23220
cacaacgcgc agcccgtggg ctcgtgatgc ttgtaggtca cctctgcaaa cgactgcagg  23280
tacgcctgca ggaatcgccc catcatcgtc acaaaggtct tgttgctggt gaaggtcagc  23340
tgcaacccgc ggtgctcctc gttcagccag gtcttgcata cggccgccag agcttccact  23400
tggtcaggca gtagtttgaa gttcgccttt agatcgttat ccacgtggta cttgtccatc  23460
agcgcgcgcg cagcctccat gcccttctcc cacgcagaca cgatcggcac actcagcggg  23520
ttcatcaccg taatttcact ttccgcttcg ctgggctctt cctcttcctc ttgcgtccgc  23580
ataccacgcg ccactgggtc gtcttcattc agccgccgca ctgtgcgctt acctcctttg  23640
ccatgcttga ttagcaccgg tgggttgctg aaacccacca tttgtagcgc cacatcttct  23700
ctttcttcct cgctgtccac gattacctct ggtgatggcg ggcgctcggg cttgggagaa  23760
gggcgcttct ttttcttctt gggcgcaatg gccaaatccg ccgccgaggt cgatggccgc  23820
gggctgggtg tgcgcggcac cagcgcgtct tgtgatgagt cttcctcgtc ctcggactcg  23880
atacgccgcc tcatccgctt ttttggggc gcccggggag gcggcggcga cgggacggg  23940
gacgacacgt cctccatggt tgggggacgt cgcgccgcac cgcgtccgcg ctcggggtg  24000
gtttcgcgct gctcctcttc ccgactggcc atttccttct cctataggca gaaaagatc  24060
atggagtcag tcgagaagaa ggacagccta accgccccct ctgagttcgc caccaccgcc  24120
tccaccgatg ccgccaacgc gcctaccacc ttccccgtcg aggcacccccc gcttgaggag  24180
gaggaagtga ttatcgagca ggacccaggt tttgtaagcg aagacgacga ggaccgctca  24240
gtaccaacag aggataaaaa gcaagaccag gacaacgcag aggcaaacga ggaacaagtc  24300
gggcgggggg acgaaaggca tggcgactac ctagatgtgg gagacgacgt gctgttgaag  24360
catctgcagc gccagtgcgc cattatctgc gacgcgttgc aagagcgcag cgatgtgccc  24420
ctcgccatag cggatgtcag ccttgcctac gaacgccacc tattctcacc gcgcgtaccc  24480
cccaaacgcc aagaaaacgg cacatgcgag cccaacccgc gcctcaactt ctaccccgta  24540
tttgccgtgc cagaggtgct tgccacctat cacatctttt tccaaaactg caagatacccc  24600
ctatcctgcc gtgccaaccg cagccgagcg acaagcagc tggccttgcg gcagggcgct  24660
gtcataccctg atatcgcctc gctcaacgaa gtgccaaaaa tctttgaggg tcttggacgc  24720
gacgagaagc gcgcggcaaa cgctctgcaa caggaaaaca gcgaaaatga aagtcactct  24780
ggagtgttgg tggaactcga gggtgacaac gcgcgcctag ccgtactaaa acgcagcatc  24840
gaggtcaccc actttgccta cccggcactt aacctacccc caaggtcat gagcacagtc  24900
atgagtgagc tgatcgtgcg ccgtgcgcag ccctggaga gggatgcaaa tttgcaagaa  24960
caaacagagg agggcctacc cgcagttggc gacgagcagc tagcgcgctg gcttcaaacg  25020
cgcgagcctg ccgacttgga ggagcgacgc aaactaatga tggccgcagt gctcgttacc  25080
```

```
gtggagcttg agtgcatgca gcggttcttt gctgacccgg agatgcagcg caagctagag    25140
gaaacattgc actacacctt tcgacagggc tacgtacgcc aggcctgcaa gatctccaac    25200
gtggagctct gcaacctggt ctcctacctt ggaattttgc acgaaaaccg ccttgggcaa    25260
aacgtgcttc attccacgct caagggcgag gcgcgccgcg actacgtccg cgactgcgtt    25320
tacttatttc tatgctacac ctggcagacg gccatgggcg tttggcagca gtgcttggag    25380
gagtgcaacc tcaaggagct gcagaaactg ctaaagcaaa acttgaagga cctatggacg    25440
gccttcaacg agcgctccgt ggccgcgcac ctggcggaca tcattttccc cgaacgcctg    25500
cttaaaaccc tgcaacaggg tctgccagac ttcaccagtc aaagcatgtt gcagaacttt    25560 aggaaccttta tcctagagcg ctcaggaatc ttgcccgcca cctgctgtgc acttcctagc    25620
gactttgtgc ccattaagta ccgcgaatgc cctccgccgc tttggggcca ctgctacctt    25680
ctgcagctag ccaactacct tgcctaccac tctgacataa tggaagacgt gagcggtgac    25740
ggtctactgg agtgtcactg tcgctgcaac ctatgcaccc cgcaccgctc cctggtttgc    25800
aattcgcagc tgcttaacga aagtcaaatt atcggtacct ttgagctgca gggtccctcg    25860
cctgacgaaa agtccgcggc tccggggttg aaactcactc cggggctgtg gacgtcggct    25920
taccttcgca aatttgtacc tgaggactac cacgcccacg agattaggtt ctacgaagac    25980
caatcccgcc cgccaaatgc ggagcttacc gcctgcgtca ttacccaggg ccacattctt    26040
ggccaattgc aagccatcaa caaagcccgc caagagtttc tgctacgaaa gggacggggg    26100
gtttacttgg accccagtc cggcgaggag ctcaacccaa tcccccgcc gccgcagccc    26160 tatcagcagc agccgcgggc ccttgcttcc caggatggca cccaaaaaga agctgcagct    26220
gccgccgcca cccacggacg aggaggaata ctgggacagt caggcagagg aggttttgga    26280
cgaggaggag gaggacatga tggaagactg ggagagccta gacgaggaag cttccgaggt    26340
cgaagaggtg tcagacgaaa caccgtcacc ctcggtcgca ttcccctcgc cggcgcccca    26400
gaaatcggca accggttcca gcatggctac aacctccgct cctcaggcgc cgccggcact    26460
gcccgttcgc cgacccaacc gtagatggga caccactgga accagggccg gtaagtccaa    26520
gcagccgccg ccgttagccc aagagcaaca acagcgccaa ggctaccgct catggcgcgg    26580
gcacaagaac gccatagttg cttgcttgca agactgtggg ggcaacatct ccttcgcccg    26640
ccgctttctt ctctaccatc acggcgtggc cttcccccgt aacatcctgc attactaccg    26700
tcatctctac agcccatact gcaccggcgg cagcggcagc ggcagcaaca gcagcggcca    26760
cacagaagca aaggcgaccg gatagcaaga ctctgacaaa gcccaagaaa tccacagcgg    26820
cggcagcagc aggaggagga gcgctgcgtc tggcgcccaa cgaacccgta tcgacccgcg    26880
agcttagaaa caggattttt cccactctgt atgctatatt tcaacagagc aggggccaag    26940
aacaagagct gaaaataaaa aacaggtctc tgcgatccct caccccgcagc tgcctgtatc    27000 acaaaagcga agatcagctt cggcgcacgc tggaagacgc ggaggctctc ttcagtaaat    27060
actgcgcgct gactcttaag gactagtttc gcgcccttttc tcaaatttaa gcgcgaaaac    27120
tacgtcatct ccagcggcca cacccggcgc cagcacctgt cgtcagcgcc attatgagca    27180
aggaaattcc cacgccctac atgtggagtt accagccaca aatgggactt gcggctggag    27240
ctgcccaaga ctactcaacc cgaataaact acatgagcgc gggaccccac atgatatccc    27300
gggtcaacgg aatccgcgcc caccgaaacc gaattctctt ggaacaggcg gctattacca    27360
ccacacctcg taataacctt aatccccgta gttggcccgc tgcctggtg taccaggaaa    27420 gtcccgctcc caccactgtg gtacttccca gagacgccca ggccgaagtt cagatgacta    27480
```

```
actcagggc gcagcttgcg ggcggctttc gtcacagggt gcggtcgccc gggcagggta    27540
taactcacct gacaatcaga gggcgaggta ttcagctcaa cgacgagtcg gtgagctcct    27600
cgcttggtct ccgtccggac gggacatttc agatcggcgg cgccggccgt ccttcattca    27660
cgcctcgtca ggcaatccta actctgcaga cctcgtcctc tgagccgcgc tctggaggca    27720
ttggaactct gcaatttatt gaggagtttg tgccatcggt ctactttaac cccttctcgg    27780
gacctcccgg ccactatccg gatcaattta ttcctaactt tgacgcggta aaggactcgg    27840
cggacggcta cgactgaatg ttaagtggag aggcagagca actgcgcctg aaacacctgg    27900
tccactgtcg ccgccacaag tgctttgccc gcgactccgg tgagttttgc tactttgaat    27960
tgcccgagga tcatatcgag ggcccggcgc acggcgtccg gcttaccgcc cagggagagc    28020
ttgcccgtag cctgattcgg gagtttaccc agcgccccct gctagttgag cgggacaggg    28080
gaccctgtgt tctcactgtg atttgcaact gtcctaacct tggattacat caagatcttt    28140
gttgccatct ctgtgctgag tataataaat acagaaatta aaatatactg gggctcctat    28200
cgccatcctg taaacgccac cgtcttcacc cgcccaagca aaccaaggcg aaccttacct    28260
ggtacttta acatctctcc ctctgtgatt tacaacagtt tcaacccaga cggagtgagt    28320
ctacgagaga acctctccga gctcagctac tccatcagaa aaaacaccac cctccttacc    28380
tgccgggaac gtacgagtgc gtcaccggcc gctgcaccac acctaccgcc tgaccgtaaa    28440
ccagacttt tccggacaga cctcaataac tctgtttacc agaacaggag gtgagcttag    28500
aaaacccta gggtattagg ccaaaggcgc agctactgtg gggtttatga acaattcaag    28560
caactctacg ggctattcta attcaggttt ctctagaatc ggggttgggg ttattctctg    28620
tcttgtgatt ctctttattc ttatactaac gcttctctgc ctaaggctcg ccgcctgctg    28680
tgtgcacatt tgcatttatt gtcagctttt taaacgctgg ggtcgccacc caagatgatt    28740
aggtacataa tcctaggttt actcacccct gcgtcagccc acggtaccac ccaaaaggtg    28800
gatttaagg agccagcctg taatgttaca ttcgcagctg aagctaatga gtgcaccact    28860
cttataaaat gcaccacaga acatgaaaag ctgcttattc gccacaaaaa caaaattggc    28920
aagtatgctg tttatgctat ttggcagcca ggtgacacta cagagtataa tgttacagtt    28980
ttccagggta aaagtcataa aacttttatg tatacttttc cattttatga aatgtgcgac    29040
attaccatgt acatgagcaa acagtataag ttgtggcccc cacaaaattg tgtgaaaaac    29100
actggcactt tctgctgcac tgctatgcta attacagtgc tcgctttggt ctgtaccta    29160
ctctatatta aatacaaaag cagacgcagc tttattgagg aaaagaaaat gccttaattt    29220
actaagttac aaagctaatg tcaccactaa ctgctttact cgctgcttgc aaaacaaatt    29280
caaaaagtta gcattataat tagaatagga tttaaacccc ccggtcattt cctgctcaat    29340
accattcccc tgaacaattg actctatgtg ggatatgctc cagcgctaca accttgaagt    29400
caggcttcct ggatgtcagc atctgacttt ggccagcacc tgtccgcgg atttgttcca    29460
gtccaactac agcgacccac cctaacagag atgaccaaca caaccaacgc ggccgccgct    29520
accggactta catctaccac aaatacaccc caagtttctg cctttgtcaa taactgggat    29580
aacttgggca tgtggtggtt ctccatacg cttatgtttg tatgccttat tattatgtgg    29640
ctcatctgct gcctaaagcg caaacgcgcc cgaccaccca tctatagtcc catcattgtg    29700
ctacacccaa acaatgatgg aatccataga ttggacggac tgaaacacat gttctttttct    29760
cttacagtat gattaaatga gacatgattc ctcgagtttt tatattactg acccttgttg    29820
cgcttttttg tgcgtgctcc acattggctg cggtttctca catcgaagta gactgcattc    29880
```

```
cagccttcac agtctatttg ctttacggat ttgtcaccct cacgctcatc tgcagcctca    29940
tcactgtggt catcgccttt atccagtgca ttgactgggt ctgtgtgcgc tttgcatatc    30000
tcagacacca tccccagtac agggacagga ctatagctga gcttcttaga attctttaat    30060
tatgaaattt actgtgactt ttctgctgat tatttgcacc ctatctgcgt tttgttcccc    30120
gacctccaag cctcaaagac atatatcatg cagattcact cgtatatgga atattccaag    30180
ttgctacaat gaaaaaagcg atctttccga agcctggtta tatgcaatca tctctgttat    30240
ggtgttctgc agtaccatct tagccctagc tatatatccc taccttgaca ttggctggaa    30300
acgaatagat gccatgaacc acccaacttt ccccgcgccc gctatgcttc cactgcaaca    30360
agttgttgcc ggcggctttg tcccagccaa tcagcctcgc cccacttctc cacccccac    30420 tgaaatcagc tactttaatc taacaggagg agatgactga caccctagat ctagaaatgg    30480
acggaattat tacagagcag cgcctgctag aaagacgcag ggcagcggcc gagcaacagc    30540
gcatgaatca agagctccaa gacatggtta acttgcacca gtgcaaaagg ggtatctttt    30600
gtctggtaaa gcaggccaaa gtcacctacg acagtaatac caccggacac cgccttagct    30660
acaagttgcc aaccaagcgt cagaaattgg tggtcatggt gggagaaaag cccattacca    30720
taactcagca ctcggtagaa accgaaggct gcattcactc accttgtcaa ggacctgagg    30780
atctctgcac ccttattaag accctgtgcg gtctcaaaga tcttattccc tttaactaat    30840 aaaaaaaat aataaagcat cacttactta aaatcagtta gcaaatttct gtccagttta    30900
ttcagcagca cctccttgcc ctcctcccag ctctggtatt gcagcttcct cctggctgca    30960
aactttctcc acaatctaaa tggaatgtca gtttcctcct gttcctgtcc atccgcaccc    31020
actatcttca tgttgttgca gatgaagcgc gcaagaccgt ctgaagatac cttcaacccc    31080
gtgtatccat atgacacgga aaccggtcct ccaactgtgc cttttcttac tcctccctt    31140 gtatccccca tgggtttca agagagtccc cctggggtac tctctttgcg cctatccgaa    31200
cctctagtta cctccaatgg catgcttgcg ctcaaaatgg caacggcct ctctctggac    31260 gaggccggca accttacctc ccaaaatgta accactgtga gcccacctct caaaaaaacc    31320
aagtcaaaca taaacctgga aatatctgca ccccctcacag ttacctcaga gccctaact    31380 gtggctgccg ccgcacctct aatggtcgcg ggcaacacac tcaccatgca atcacaggcc    31440
ccgctaaccg tgcacgactc caaacttagc attgccaccc aaggacccct cacagtgtca    31500
gaaggaaagc tagccctgca acatcaggc cccctcacca ccaccgatag cagtacccctt    31560 actatcactg cctcaccccc tctaactact gccactggta gcttgggcat tgacttgaaa    31620
gagcccattt atacacaaaa tggaaaacta ggactaaagt acggggctcc tttgcatgta    31680
acagacgacc taaacacttt gaccgtagca actggtccag gtgtgactat taataatact    31740
tccttgcaaa ctaaagttac tggagccttg ggttttgatt cacaaggcaa tatgcaactt    31800
aatgtagcag gaggactaag gattgattct caaaacagac gccttatact tgatgttagt    31860
tatccgtttg atgctcaaaa ccaactaaat ctaagactag acagggccc tctttttata    31920 aactcagccc acaacttgga tattaactac aacaaggcc tttacttgtt tacagcttca    31980
aacaattcca aaagcttga ggttaaccta agcactgcca aggggttgat gtttgacgct    32040
acagccatag ccattaatgc aggagatggg cttgaatttg gttcacctaa tgcaccaaac    32100
acaaatcccc tcaaaacaaa aattggccat ggcctagaat ttgattcaaa caaggctatg    32160
gttcctaaac taggaactgg ccttagtttt gacagcacag gtgccattac agtaggaaac    32220
aaaaataatg ataagctaac tttgtggacc acaccagctc catctcctaa ctgtagacta    32280
```

```
aatgcagaga aagatgctaa actcactttg gtcttaacaa aatgtggcag tcaaatactt   32340
gctacagttt cagttttggc tgttaaaggc agtttggctc caatatctgg aacagttcaa   32400
agtgctcatc ttattataag atttgacgaa aatggagtgc tactaaacaa ttccttcctg   32460
gacccagaat attggaactt tagaaatgga gatcttactg aaggcacagc ctatacaaac   32520
gctgttggat ttatgcctaa cctatcagct tatccaaaat ctcacggtaa aactgccaaa   32580
agtaacattg tcagtcaagt ttacttaaac ggagacaaaa ctaaacctgt aacactaacc   32640
attacactaa acggtacaca ggaaacagga gacacaactc caagtgcata ctctatgtca   32700
ttttcatggg actggtctgg ccacaactac attaatgaaa tatttgccac atcctcttac   32760 acttttcat acattgccca agaataaaga atcgtttgtg ttatgtttca acgtgtttat   32820
ttttcaattg cagaaaattt caagtcattt ttcattcagt agtatagccc caccaccaca   32880
tagcttatac agatcaccgt accttaatca aactcacaga accctagtat tcaacctgcc   32940
acctccctcc caacacacag agtacacagt cctttctccc cggctggcct taaaaagcat   33000
catatcatgg gtaacagaca tattcttagg tgttatattc cacacggttt cctgtcgagc   33060
caaacgctca tcagtgatat taataaactc cccgggcagc tcacttaagt tcatgtcgct   33120
gtccagctgc tgagccacag gctgctgtcc aacttgcggt tgcttaacgg gcggcgaagg   33180
agaagtccac gcctacatgg gggtagagtc ataatcgtgc atcaggatag ggcggtggtg   33240
ctgcagcagc gcgcgaataa actgctgccg ccgccgctcc gtcctgcagg aatacaacat   33300
ggcagtggtc tcctcagcga tgattcgcac cgcccgcagc ataaggcgcc ttgtcctccg   33360
ggcacagcag cgcaccctga tctcacttaa atcagcacag taactgcagc acagcaccac   33420
aatattgttc aaaatcccac agtgcaaggc gctgtatcca aagctcatgg cggggaccac   33480
agaacccacg tggccatcat accacaagcg caggtagatt aagtggcgac ccctcataaa   33540
cacgctggac ataaacatta cctcttttgg catgttgtaa ttcaccacct cccggtacca   33600
tataaacctc tgattaaaca tggcgccatc caccaccatc ctaaaccagc tggccaaaac   33660
ctgcccgccg gctatacact gcagggaacc gggactggaa caatgacagt ggagagccca   33720
ggactcgtaa ccatggatca tcatgctcgt catgatatca atgttggcac aacacaggca   33780
cacgtgcata cacttcctca ggattacaag ctcctcccgc gttagaacca tatcccaggg   33840
aacaacccat tcctgaatca gcgtaaatcc cacactgcag ggaagacctc gcacgtaact   33900
cacgttgtgc attgtcaaag tgttacattc gggcagcagc ggatgatcct ccagtatggt   33960
agcgcgggtt tctgtctcaa aaggaggtag acgatcccta ctgtacggag tgcgccgaga   34020
caaccgagat cgtgttggtc gtagtgtcat gccaaatgga acgccggacg tagtcatatt   34080
tcctgaagca aaaccaggtg cgggcgtgac aaacagatct gcgtctccgg tctcgccgct   34140
tagatcgctc tgtgtagtag ttgtagtata tccactctct caaagcatcc aggcgccccc   34200
tggcttcggg ttctatgtaa actccttcat gcgccgctgc cctgataaca tccaccaccg   34260
cagaataagc cacacccagc caacctacac attcgttctg cgagtcacac acgggaggag   34320
cgggaagagc tggaagaacc atgtttttt ttttattcca aaagattatc caaaacctca   34380
aaatgaagat ctattaagtg aacgcgctcc cctccggtgg cgtggtcaaa ctctacagcc   34440
aaagaacaga taatggcatt tgtaagatgt tgcacaatgg cttccaaaag gcaaacggcc   34500
ctcacgtcca agtggacgta aaggctaaac ccttcagggt gaatctcctc tataaacatt   34560
ccagcacctt caaccatgcc caaataattc tcatctcgcc accttctcaa tatatctcta   34620
agcaaatccc gaatattaag tccggccatt gtaaaaatct gctccagagc gccctccacc   34680
```

```
ttcagcctca agcagcgaat catgattgca aaaattcagg ttcctcacag acctgtataa    34740
gattcaaaag cggaacatta acaaaaatac cgcgatcccg taggtccctt cgcagggcca    34800
gctgaacata atcgtgcagg tctgcacgga ccagcgcggc cacttccccg ccaggaacca    34860
tgacaaaaga acccacactg attatgacac gcatactcgg agctatgcta accagcgtag    34920
ccccgatgta agcttgttgc atgggcggcg atataaaatg caaggtgctg ctcaaaaaat    34980
caggcaaagc ctcgcgcaaa aaagaaagca catcgtagtc atgctcatgc agataaaggc    35040
aggtaagctc cggaaccacc acagaaaaag acaccattt tctctcaaac atgtctgcgg    35100
gtttctgcat aaacacaaaa taaataaca aaaaaacatt taaacattag aagcctgtct    35160
tacaacagga aaaacaaccc ttataagcat aagacggact acggccatgc cggcgtgacc    35220
gtaaaaaaac tggtcaccgt gattaaaaag caccaccgac agctcctcgg tcatgtccgg    35280
agtcataatg taagactcgg taaacacatc aggttgattc acatcggtca gtgctaaaaa    35340
gcgaccgaaa tagcccgggg gaatacatac ccgcaggcgt agagacaaca ttacagcccc    35400
cataggaggt ataacaaaat taataggaga gaaaaacaca taaacacctg aaaaaccctc    35460
ctgcctaggc aaaatagcac cctcccgctc cagaacaaca tacagcgctt ccacagcggc    35520
agccataaca gtcagcctta ccagtaaaaa agaaaaccta ttaaaaaaac accactcgac    35580
acggcaccag ctcaatcagt cacagtgtaa aaaagggcca agtgcagagc gagtatatat    35640
aggactaaaa aatgacgtaa cggttaaagt ccacaaaaaa cacccagaaa accgcacgcg    35700
aacctacgcc cagaaacgaa agccaaaaaa cccacaactt cctcaaatcg tcacttccgt    35760
tttcccacgt tacgtaactt cccatttaa gaaaactaca attcccaaca catacaagtt    35820
actccgccct aaaacctacg tcacccgccc cgttcccacg ccccgcgcca cgtcacaaac    35880
tccaccccct cattatcata ttggcttcaa tccaaaataa ggtatattat tgatgatg      35938
```

ANTI-CANCER ADENOVIRUSES

CROSS-REFERENCE TO RELATED APPLICATIONS

This application is a continuation application of PCT Application No. PCT/US2011/048005, filed Aug. 16, 2011, which claims the benefit of U.S. Provisional Application No. 61/374,215 filed Aug. 16, 2010, which are hereby incorporated in their entirety and for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 92150-865556_ST25.TXT, created on May 20, 2013, 50, 111 bytes, machine format IBM-PC, MS-Windows operating system, is hereby incorporated by reference.

STATEMENT AS TO RIGHTS TO INVENTIONS MADE UNDER FEDERALLY SPONSORED RESEARCH OR DEVELOPMENT

This invention was made with government support under CA137094 awarded by the National Institutes of Health. The Government has certain rights in the invention.

BACKGROUND OF THE INVENTION

There are 52 human Adenoviruses which infect different human tissues and hundreds of adenoviruses that infect other species ranging from fish to primates. These viruses are highly efficient nanomachines that deliver their genomic payload to the nucleus within an hour of infection. As DNA viruses, they do not integrate into host DNA, they can be produced to high titres using established GMP protocols, and they have demonstrated safety in research and human gene therapy applications for the expression of ectopic genes. However, to date, their potential applications have been hindered by the almost exclusive use of one variety, Ad5 or an Ad2/5 chimera and the inability to engineer and combine multiple genetic modifications rapidly and systematically. Thus, there is a great need to extend the repertoire adenoviral vectors beyond that of Ad2/5 and to develop a technological platform that facilitates the rapid, de novo assembly of novel adenoviral genomes from component parts, allowing the systematic incorporation of multiple modifications and heterologous elements. Such a system would take advantage of the natural viral architecture, which is highly efficient in both delivering and expressing 36 genes (not including splice variants). The system could provide powerful diagnostic agents and therapeutic agents that incorporate multiplex and quantitative measurements of the pathway activities deregulated in different tumor samples.

The potential of adenoviral vectors in several applications is hindered by the ability to manipulate the 36 kb viral genome rapidly and systematically. Furthermore, the adenoviral vectors used in basic research, animal models, gene therapy and oncolytic therapy are limited to Adenovirus (Ad) serotypes 2 and 5. Ad2 and Ad5 were among the first to be discovered and, as such, there is a legacy of vectors/tools with which to manipulate their genomes, particularly in the E1 region. Ad2/5 Fiber proteins infect epithelial cells by binding to the receptor, CAR. Unfortunately, CAR is not expressed on all cell types and is downregulated on many metastases. Furthermore, approximately 80% of the human population has pre-existing neutralizing antibodies against Ad2/5, which together with off-target liver uptake and inflammation, limits systemic applications. Thus, the use of Ad2/5 vectors for gene delivery and cancer therapy is not necessarily an optimal choice, quite the contrary, but largely an accident of history.

Our ultimate goal is to engineer potent viral cancer therapies that not only undergo tumor selective lytic replication but which can be administered systemically in repeated rounds of treatment, avoid liver toxicity, efficiently target and cross the torturous tumor vasculature, infect cells via disparate receptors, generate a tumor bystander effect by localized expression of pro-drug activating enzymes/toxins within the tumor and which reawaken a beneficial host anti-tumor immune response. These are major challenges which are further compounded by the inability of human adenovirus to replicate in mice. This precludes the evaluation of human oncolytic viruses in immune competent genetically engineered mouse models of cancer (GEMMs) which have many advantages over xenograft models.

There are 52 human adenoviruses, indicating highly specialized adaptation for infecting and replicating in different host tissue environments. Many of these viruses infect different tissues and have Fiber proteins that bind cellular receptors other than CAR as well as a distinct cohort of 'E3' immune-modulation genes. Their unique properties have not been extensively studied or exploited due to the lack of tools necessary to modify their genomes. Similarly, there are also adenoviruses that infect other species, including mouse adenovirus (MAV-1).

Provided herein are solutions to these and other problems in the art.

BRIEF SUMMARY OF THE INVENTION

In one aspect, a modified adenovirus is provided. The modified adenovirus may be a p53 replication impaired adenovirus. The p53 replication impaired adenovirus is replication impaired when present within a p53 expressing cell and is not replication impaired when present within a p53 impaired cell.

In another aspect, a method of treating cancer is provided. The method includes administering an effective amount (e.g. a therapeutically effective dose or amount) of a modified adenovirus (as described above) or one or more nucleic acids encoding the modified adenovirus to a subject in need thereof.

BRIEF DESCRIPTION OF THE DRAWINGS

FIGS. 1A-1D. p53 levels, but not transcriptional activity, are induced by the loss of E1B-55k and p53 degradation in adenovirus infected primary or tumor cells, irrespective of ARF expression. FIG. 1A. Human primary small airway epithelial cells (SAECs) were infected with either mock, wild-type (wt) or ΔE1B-55k (Δ55k) viruses and harvested at 24, 36 and 48 hours post infection (h.p.i.). Protein lysates were normalized and analyzed for the expression of p53, p21, MDM2 and ARF. Actin expression was analyzed as a loading control. FIG. 1B. U2OS cells were infected with mock, wt or Δ55k viruses and fixed at 28 h.p.i. p53 was detected by immunofluorescence and DNA counterstained with Hoechst dye. FIG. 1C. U2OS cells were infected with mock, wt or Δ55k viruses and harvested at 24, 36 and 48 h.p.i. Doxorubicin (dox) treatment for 12 hours was used as a positive control for p53 activation. Protein lysates were normalized and analyzed for the expression of p53, p21 and MDM2. Actin expression was analyzed as a loading control. FIG. 1D. U2OS stable cell-lines with an isopropyl-β-D-thiogalactopyranoside (IPTG)

inducible ARF (NARF cells) were infected with either mock, wt or Δ55k viruses. Cells were left untreated or IPTG added at 8 h.p.i. to induce the expression of ARF. Real-Time PCR was used to quantify p21 and MDM2 mRNA levels at 36 h.p.i. (lower panel), which are plotted as fold change with respect to (wrt) mock infected cells (-ARF); vertical bars represent the standard deviation across triplicates. Protein lysates were also harvested (48 h.p.i.), normalized and analyzed for the expression of p53, p21, MDM2 and ARF (upper panel). Actin was used as a loading control.

Figure 2A:
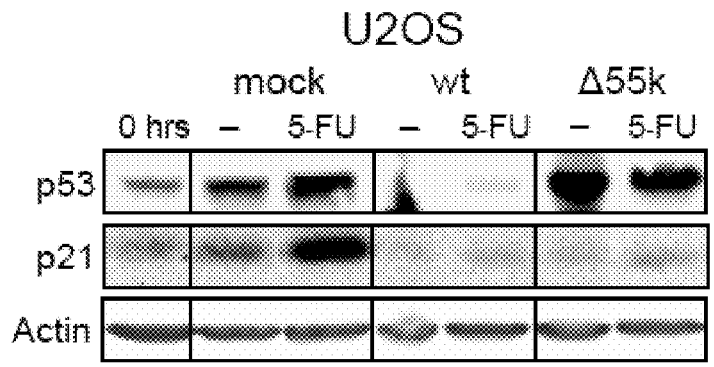
Figure 2B:
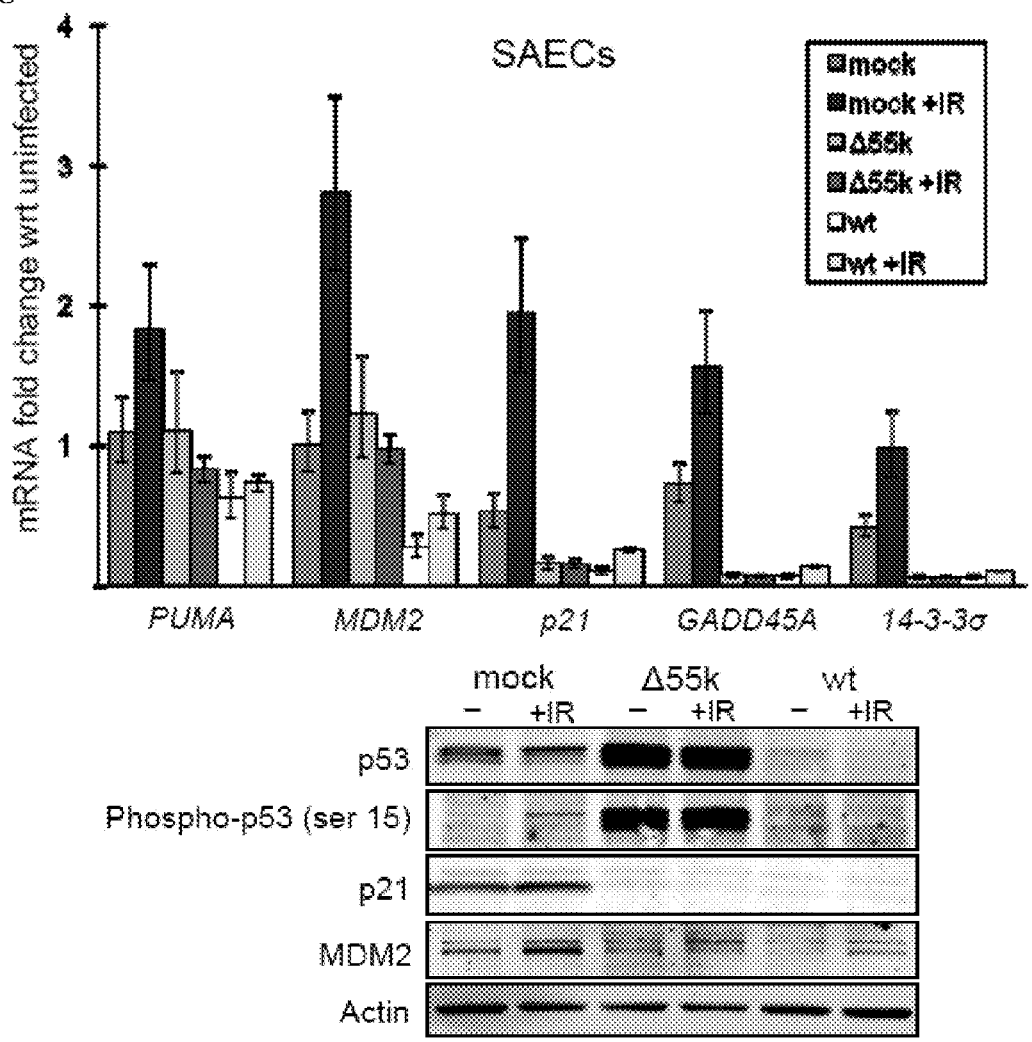
Figure 2C:
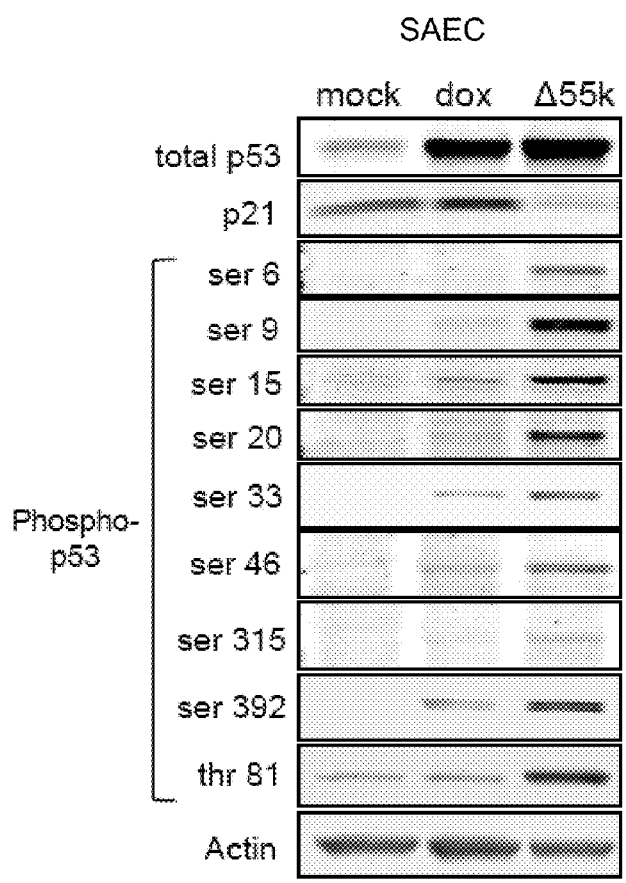
Figure 2D:
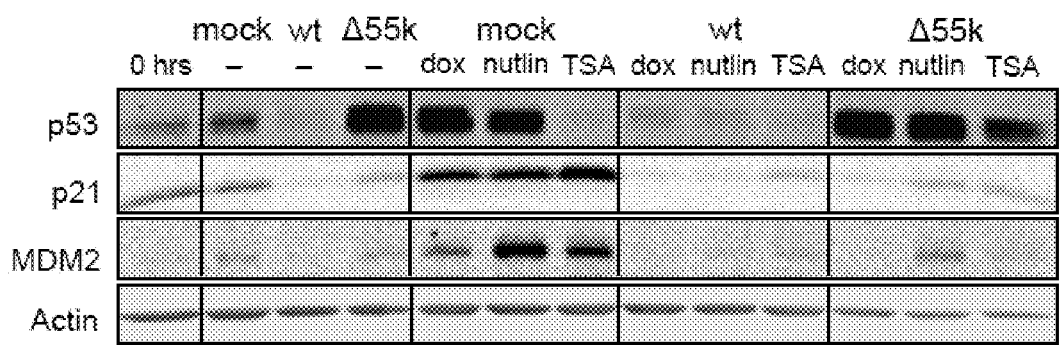

FIGS. 2A-2D. The deletion of E1B-55k induces high levels of phosphorylated p53 in adenovirus infected cells, but p53 transcriptional targets are dominantly suppressed and cannot be activated by irradiation, genotoxic drugs, ARF, MDM2 antagonists or histone deacetylase inhibitors. FIG. 2A. U2OS cells were infected with either mock, wt or Δ55k viruses. Samples were treated with vehicle control (-) or 5-fluorouracil (5-FU) at 24 h.p.i. Protein lysates were harvested at 36 h.p.i., normalized and analyzed for the expression of p53 and p21. Actin was analyzed as a loading control. FIG. 2B. SAECs were infected with either mock, Δ55k or wt viruses. Cells were left untreated or γ-irradiated (IR) with 10 Gy at 31 h.p.i. Protein lysates (lower panel) were harvested at 36 h.p.i., normalized and analyzed for the expression of p53, p21 and MDM2. p53 phosphorylation at serine (ser) 15 was detected using a phospho-specific antibody. Actin was used as a loading control. Total RNA was also harvested at 36 h.p.i. and p53 transcriptional targets quantified by Real-Time PCR (upper panel). The levels of PUMA, MDM2, p21, GADD45A and 14-3-3σ are plotted as fold change with respect to (wrt) uninfected cells at 0 hours; vertical bars represent the standard deviation across triplicates. FIG. 2C. SAECs were infected with mock or Δ55k viruses and harvested at 36 h.p.i. Doxorubicin treatment for 12 hours was used as a positive control for p53 activation. Protein lysates were normalized and analyzed by Western blotting for total p53 and p21 levels. p53 phosphorylation at ser 6 and 9 (casein kinase 1), ser 15 (ATM, ATR, DNA-PK), ser 20 (CHK1, CHK2, JNK, MAPKAP2), ser 33 (p38, PIN1), ser 46 (HIPK2 and DYRK2), threonine (thr) 81 (JNK, PIN1), ser 315 (Aurora kinase, PIN1, CDK2 and GSK-3) and ser 392 (PKR, CDK9 and p38 FACT-CK2) 3 were determined using p53 phospho-specific antibodies. FIG. 2D. SAECs were infected with mock, wt or Δ55k viruses. Samples were treated with vehicle control (- lanes), doxorubicin (dox), the MDM2 antagonist, nutlin, or trichostatin A (TSA) at 24 h.p.i. Protein lysates were harvested at 36 h.p.i., normalized and analyzed by Western blotting for p53, MDM2 and p21. Actin was used as a loading control.

Figure 3A:
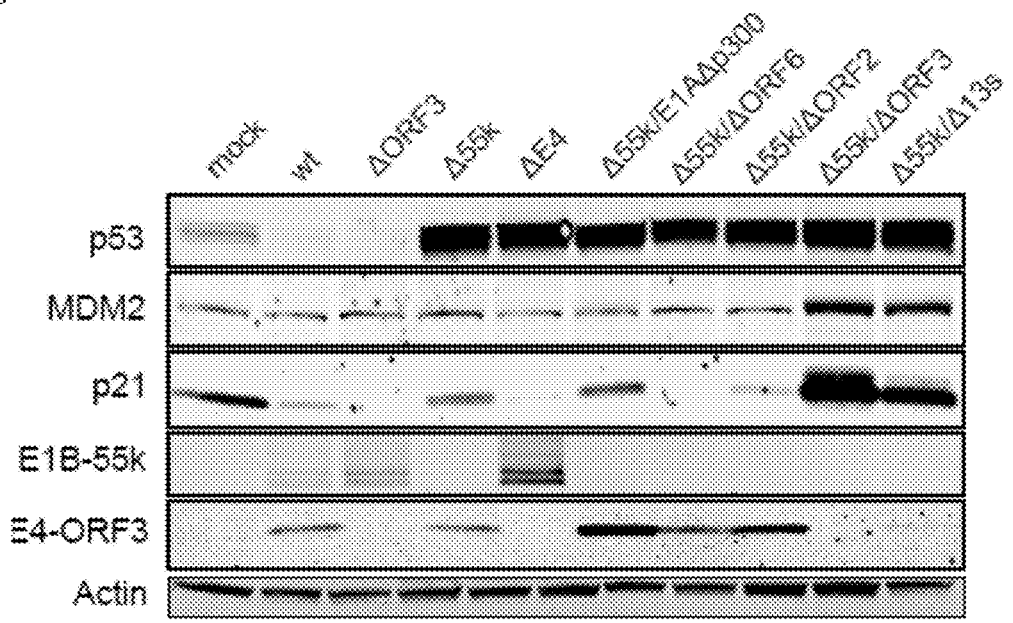
Figure 3B:
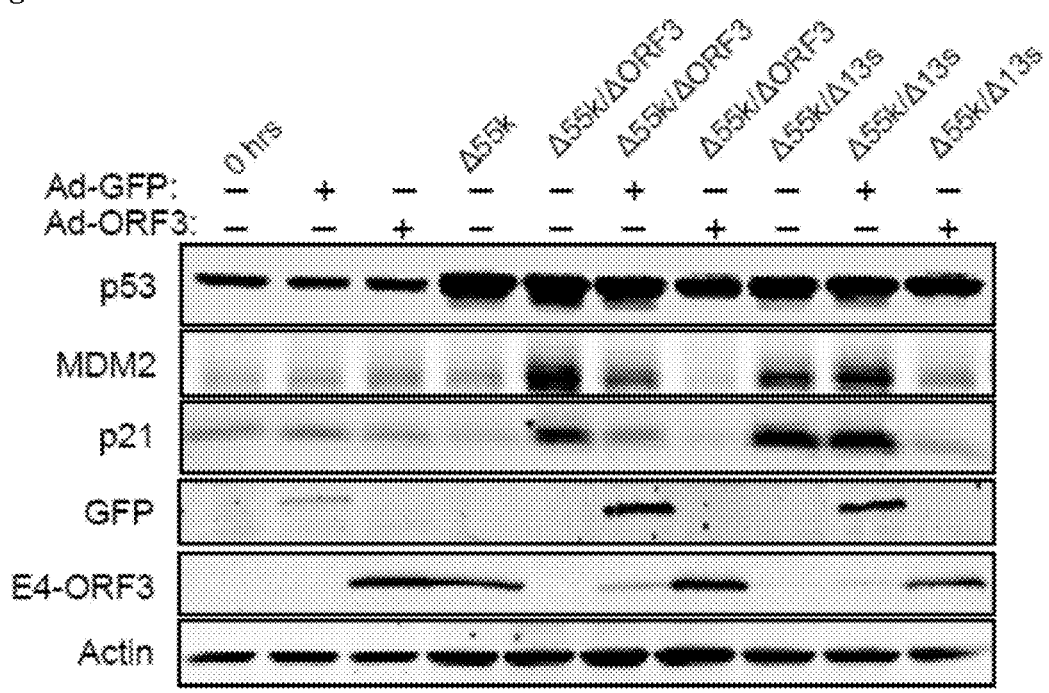
Figure 3C:
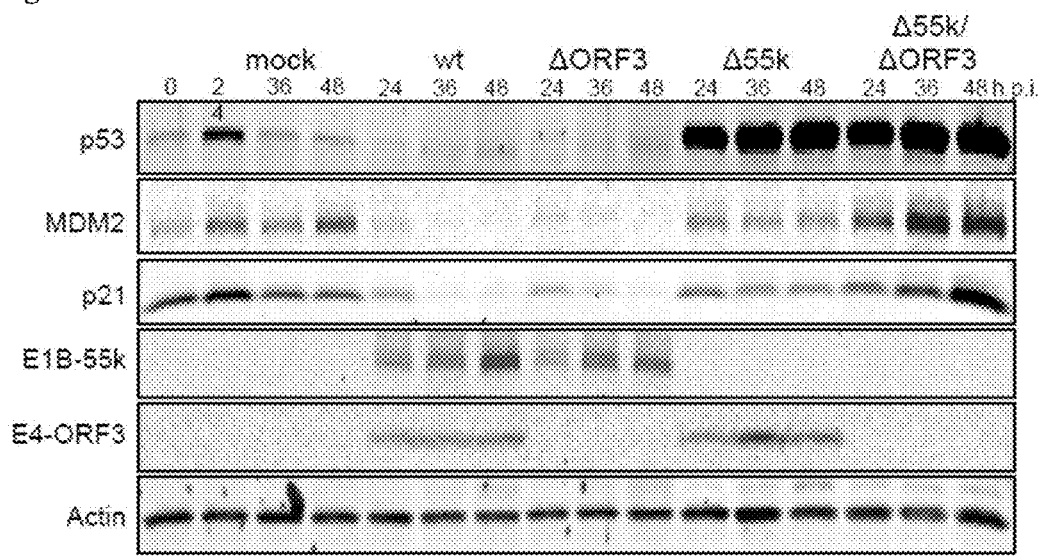
Figure 3D:
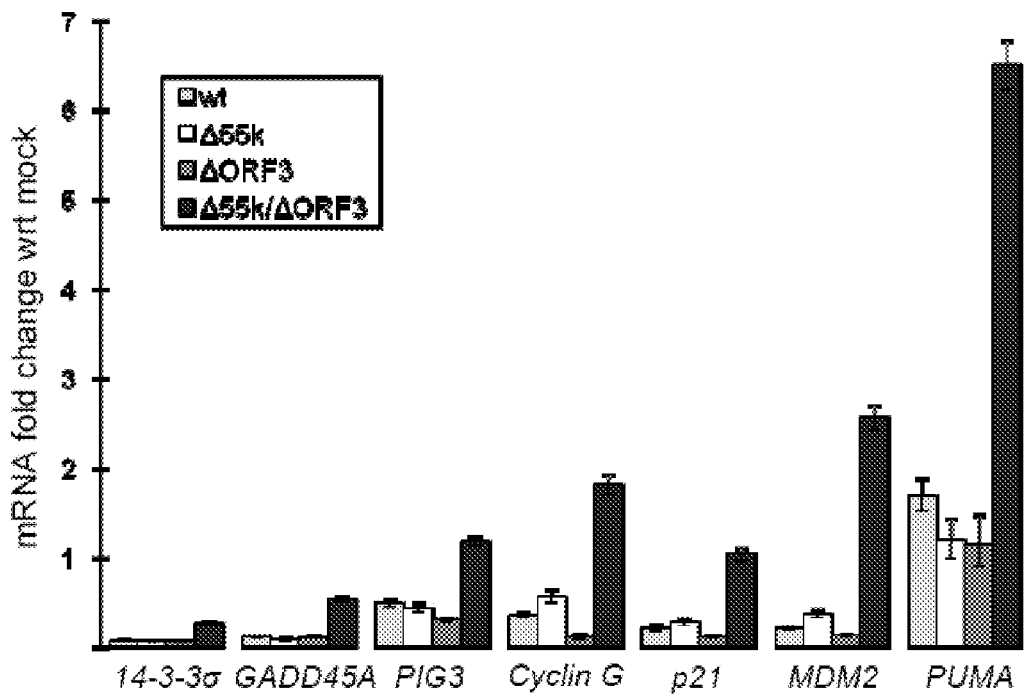
Figure 3E:
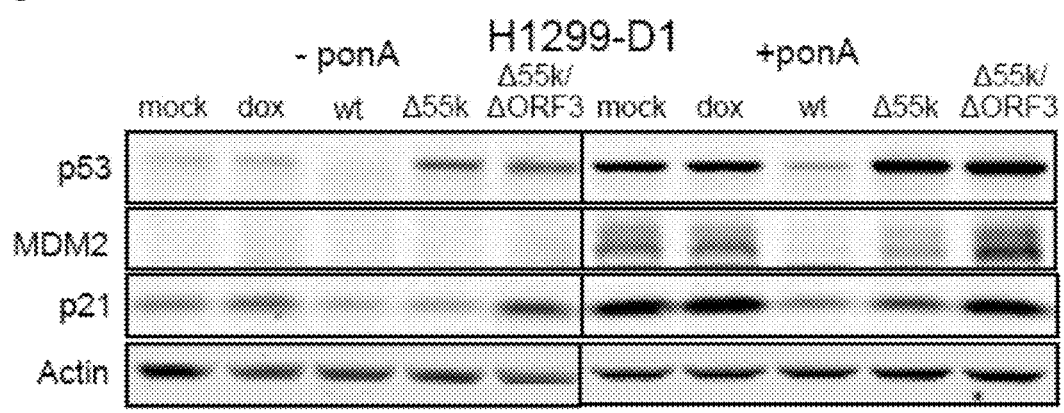

FIGS. 3A-3E. E1A-13s induces E4-ORF3, which inactivates p53 independently of E1B-55k and p53 degradation in adenovirus infected cells. FIG. 3A. SAECs were infected with the following viruses: mock, wild-type (wt), viruses with mutations in either E4-ORF3 (ΔORF3), E1B-55k (Δ55k) or an E4 gene deletion (ΔE4), viruses with compound mutations in either E1B-55k and E1A (Δ55k/E1AΔp300), E1B-55k and E4-ORF6 (Δ55k/ΔORF6), E1B-55k and E4-ORF2 (Δ55k/ΔORF2), E1B-55k and E4-ORF3 (Δ55k/ΔORF3) or E1B-55k and E1A-13s (Δ55k/Δ13s) (see FIG. 10). Protein lysates were harvested at 36 h.p.i., normalized and analyzed for the expression of p53, MDM2, p21, E1B-55k and E4-ORF3 by Western blotting. Actin expression was used as a loading control. FIG. 3B. SAECs were infected with either mock, Δ55k, Δ55k/ΔORF3 or Δ55k/Δ13s viruses. Cells were simultaneously co-infected with a control virus (Ad-GFP, + lanes) or a virus ectopically expressing E4-ORF3 (Ad-ORF3, + lanes). Protein extracts were harvested at 36 h.p.i., normalized and analyzed for the expression of p53, MDM2, p21, GFP and E4-ORF3. Actin expression was analyzed as a loading control. FIG. 3C. SAECs were infected with mock, wt, ΔORF3, Δ55k or Δ55k/ΔORF3 viruses. Protein lysates were harvested at 0, 24, 36 and 48 h.p.i., normalized and analyzed for the expression of p53, MDM2, p21, E1B-55k and E4-ORF3 by Western blotting. Actin expression was analyzed as a loading control. FIG. 3D. SAECs were infected with mock, wt, Δ55k, ΔORF3 or Δ55k/ΔORF3 viruses. RNA was harvested at 36 h.p.i. Real-Time PCR was used to quantify the mRNA levels of p53 transcriptional targets, which are graphed as fold change with respect to (wrt) mock infected cells; vertical bars represent the standard deviation. FIG. 3E. H1299-D1 cells lacking endogenous p53 but carrying a ponasterone A inducible p53 cDNA were infected with mock, wt, Δ55k or Δ55k/ΔORF3 viruses and analyzed under non-induced (-ponA) or induced (+ponA) conditions. The cells were also subjected to doxorubicin (dox) treatment. Protein extracts were harvested at 48 h.p.i. and analyzed for the expression of p53, MDM2, and p21. Actin expression was analyzed as a loading control.

Figure 4A:
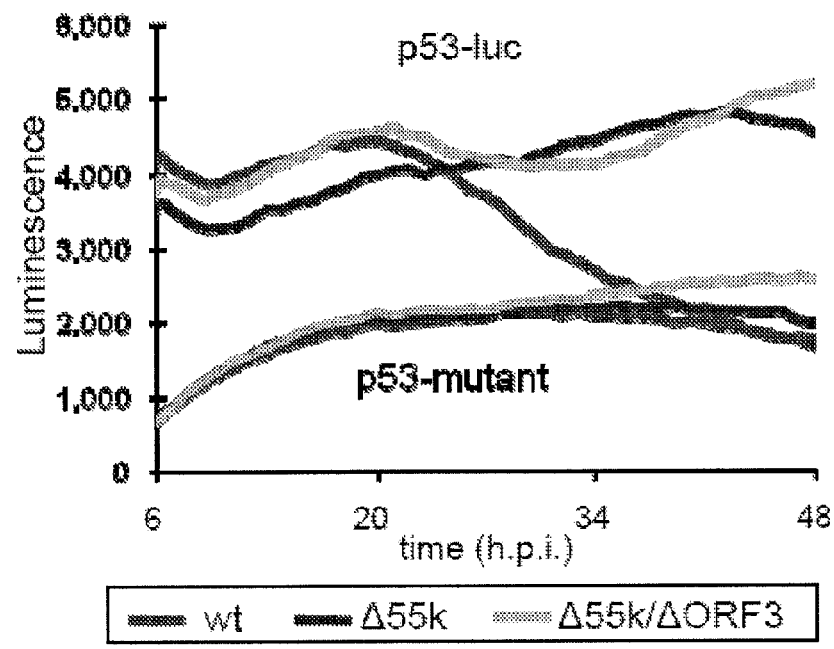
Figure 4B:
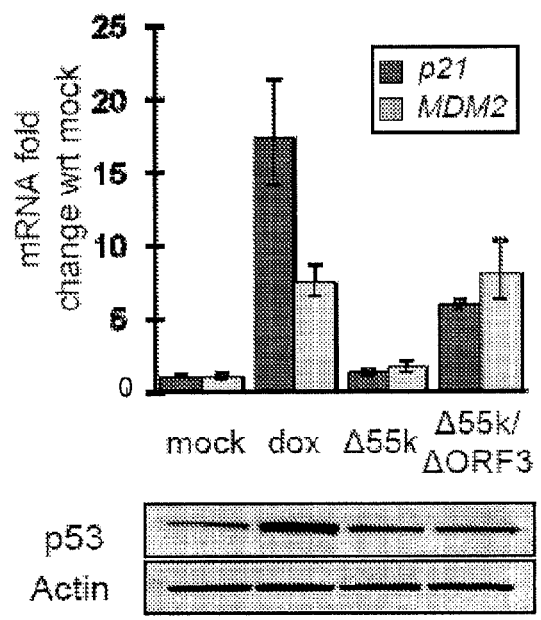
Figure 4C:
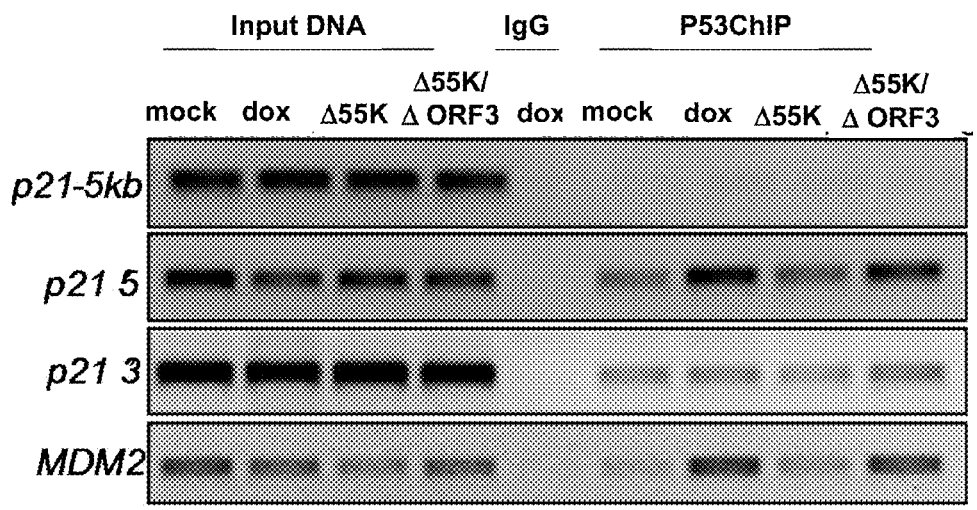
Figure 4D:
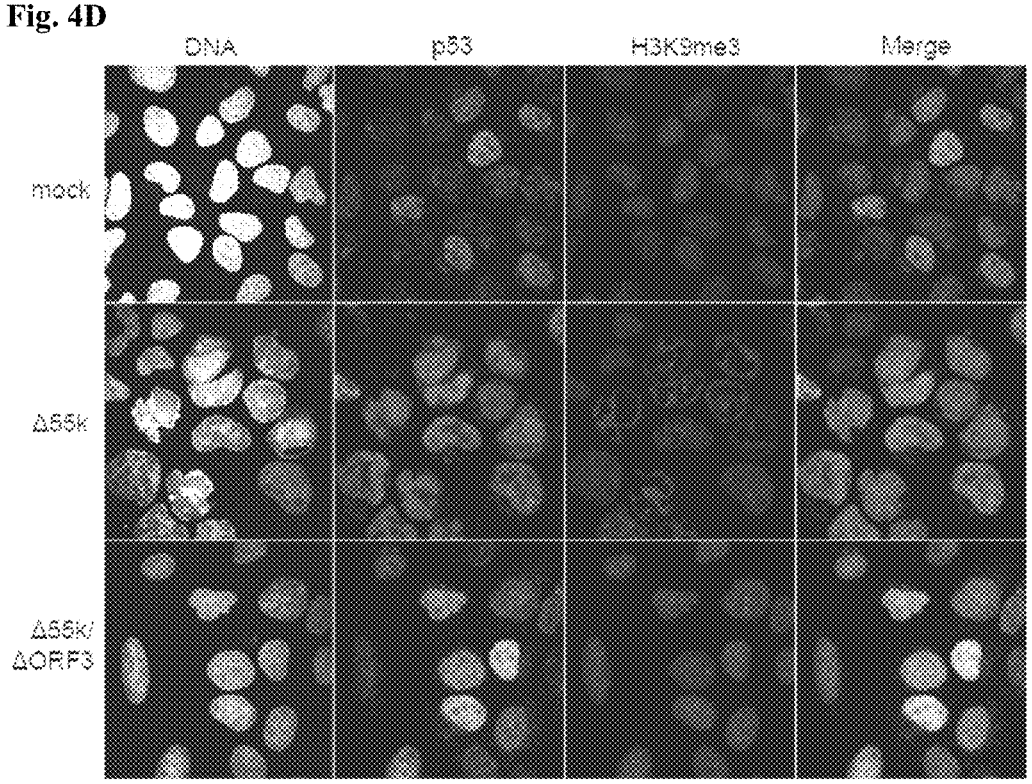
Figure 4E:
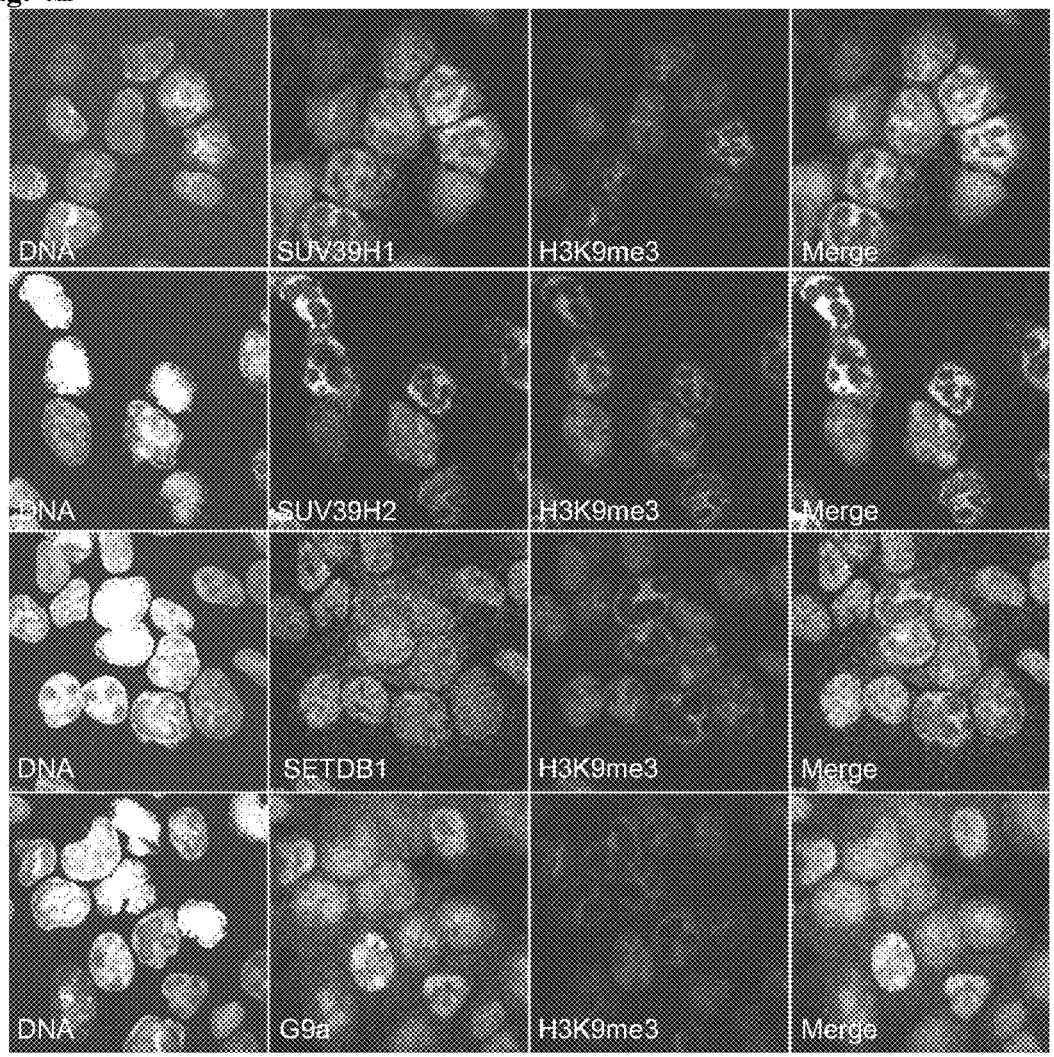
Figure 16:
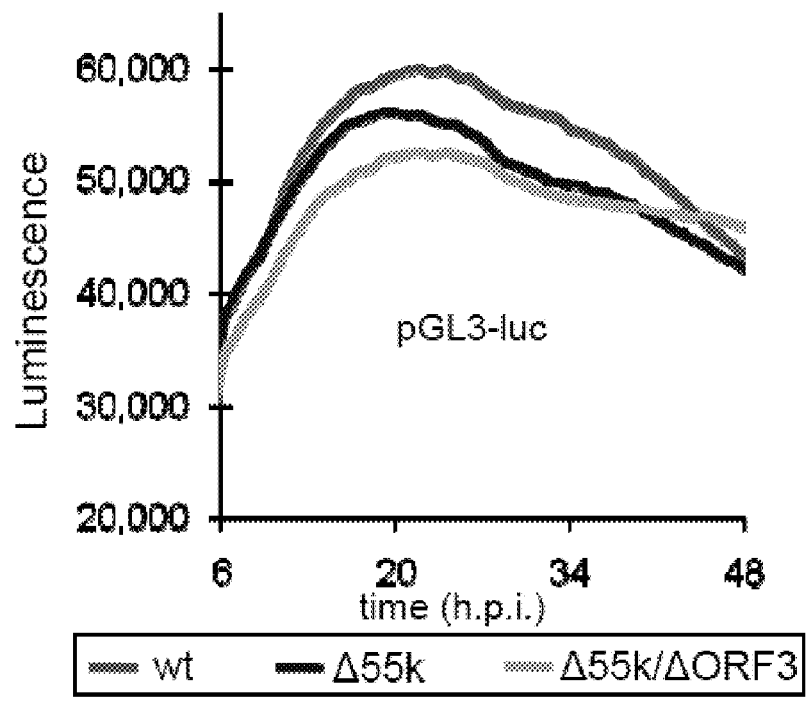

FIGS. 4A-4E. E4-ORF3 induces novel SUV39H1 and SUV39H2 H3K9me3 heterochromatin formation, and specifically prevents p53 binding and access to DNA target sites in endogenous promoters. FIG. 4A. U2OS cells were transfected (in triplicate) with either a p53-luciferase reporter (p53-luc), a p53-luciferase reporter in which the p53 binding sites are mutated (p53-mutant) or control pGL3-luciferase (pGL3-luc) plasmids (FIG. 16). Transfected cells were infected with either wt, Δ55k or Δ55k/ΔORF3 viruses and D-Luciferin added at 4 h.p.i. Luminescence readings were taken every hour for 48 hours. The average luminescence across triplicates is plotted against time (h.p.i.). FIGS. 4B and 4C. U2OS cells were infected with mock, Δ55k or Δ55k/ΔORF3 viruses. RNA, protein lysates, and chromatin were harvested at 36 h.p.i. Doxorubicin treatment for 12 hours was used as a positive control for p53 activation. b. p21 and MDM2 mRNA levels were determined by Real-Time PCR, and are graphed as fold change with respect to (wrt) mock infection (upper panel); vertical bars represent the standard deviation. Protein lysates were normalized and analyzed for p53 expression; actin was analyzed as a loading control (lower panel). FIG. 4C. Using p53 monoclonal antibodies, p53 chromatin immunoprecipitations (ChIPs) were performed. A matched IgG isotype was used as a control for specificity. ChIP samples were analyzed by semi-quantitative PCR for p53 DNA target sequences in the p21 (the 5' p53 binding site is at -2.4 kb and the 3' site is at -1.3 kb) and MDM2 promoters. The -5 kb region of the p21 promoter does not contain p53 binding sequences and was used as a negative control. The input DNA is shown on the left. FIG. 4D. U2OS cells were infected with mock, Δ55k or Δ55k/ΔORF3 viruses and fixed at 36 h.p.i. p53 (green) and histone H3 trimethyl at lysine 9 (H3K9me3, red) were detected by immunofluorescence and DNA counterstained with Hoechst (white). FIG. 4E. U2OS cells were infected with Δ55k virus and fixed at 36 h.p.i. The H3K9 methyltransferases SUV39H1, SUV39H2, SETDB1 and G9a were detected by immunofluorescence (green) together with H3K9me3 (red). DNA was counterstained with Hoechst (white).

Figure 5A:
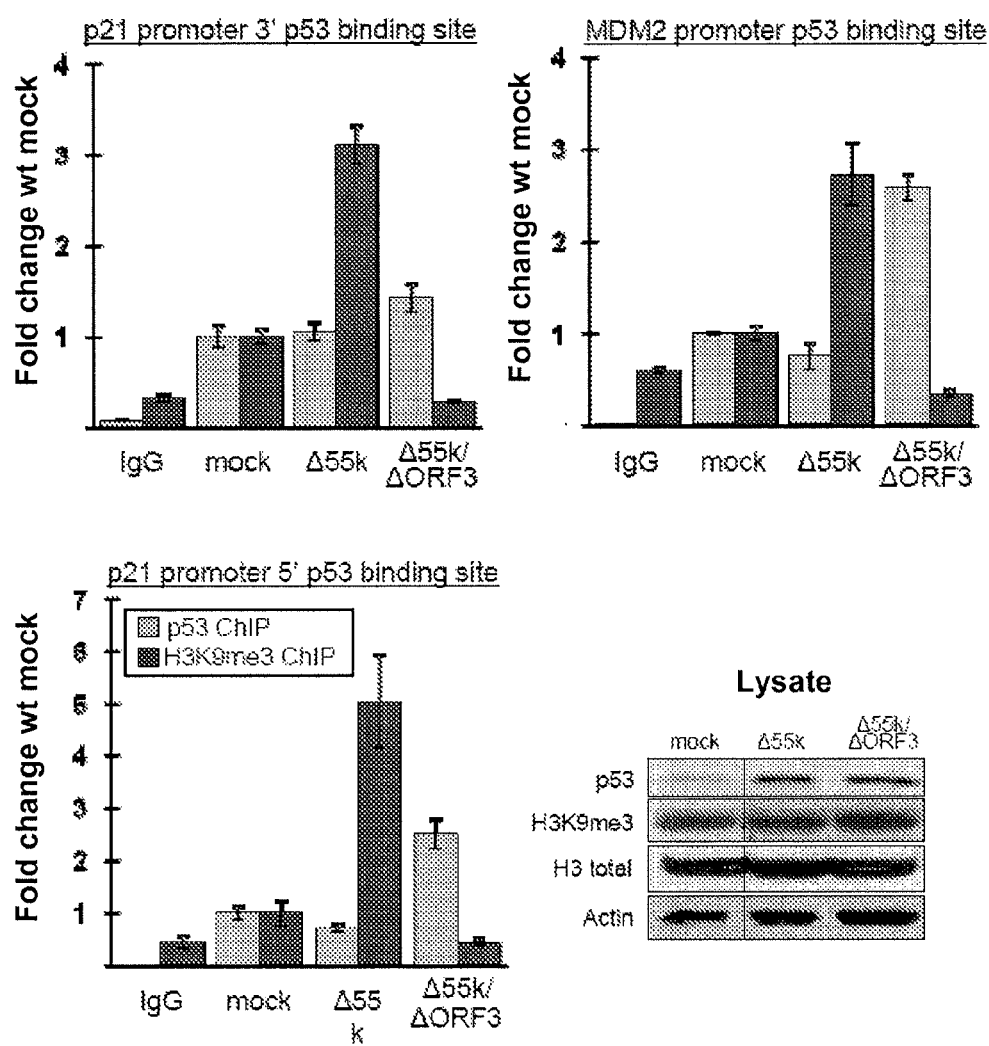
Figure 5B:
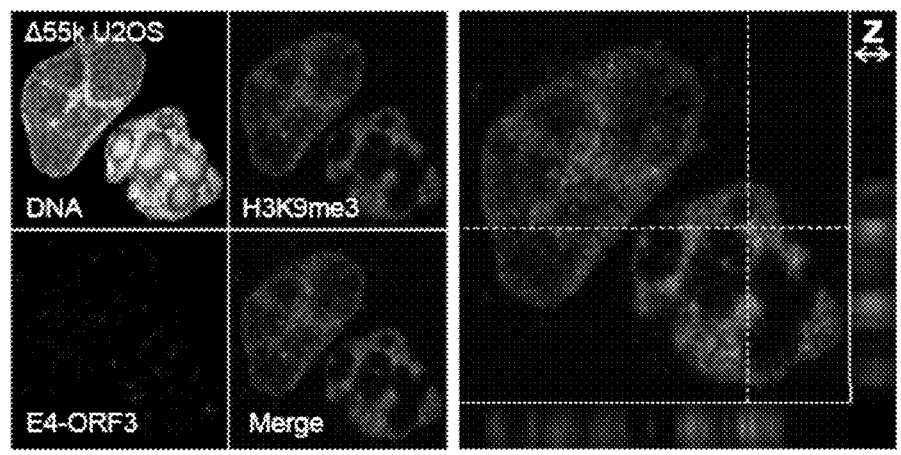
Figure 5C:
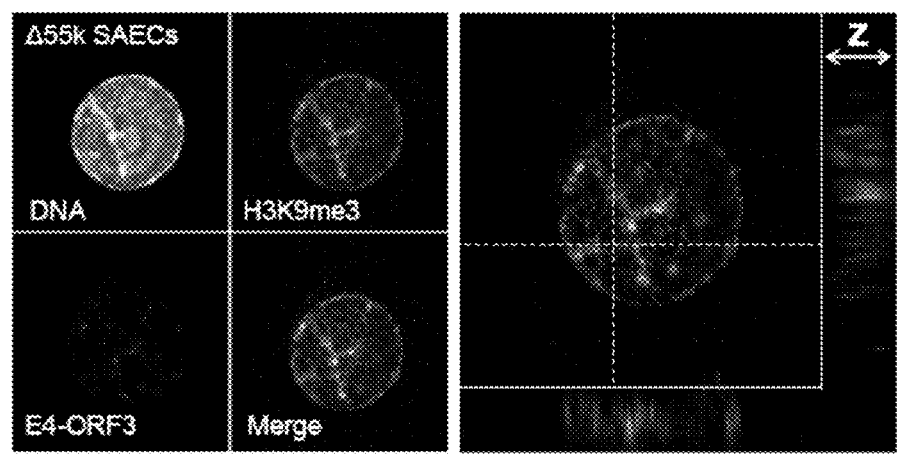
Figure 5D:

FIGS. 5A-5D. E4-ORF3 forms a nuclear scaffold that directly specifies heterochromatin assembly and induces de novo H3K9 trimethyl at p53 target promoters, preventing p53 DNA binding. FIG. 5A. U2OS cells were infected with mock, Δ55k or Δ55k/ΔORF3 viruses. Protein lysates and chromatin were harvested at 36 h.p.i. Protein lysates were normalized and analyzed for the levels of p53, actin, histone H3 (H3) and histone H3 trimethyl at lysine 9 (H3K9me3). Antibodies to H3K9me3 and p53 were used to perform chromatin immunoprecipitations. Mouse and rabbit IgGs were used as controls for specificity. ChIP samples were analyzed by Real-Time Quantitative PCR and normalized relative to input DNA. p53 and H3K9me3 binding to p53 target sequences in the p21 and MDM2 promoters are plotted as fold change with respect to (wrt) mock. IgG controls are plotted as a measure of background and control for the enrichment of target DNA sequences in p53 and H3K9me3 ChIPs. FIGS. 5B and 5C. Confocal images are shown of U2OS and small airway epithelial cells (SAECs) infected with Δ55k virus and fixed at 36 h.p.i. The left panel shows a single confocal section of cells counterstained with H3K9me3 (green), E4-ORF3 (red) and Hoechst (DNA in white). The central slice of a z-stack is illustrated on the right panel with the horizontal and vertical lines representing orthogonal cuts taken throughout the stack which are then subsequently shown as flat projections at the bottom and right-hand side of the images. FIG. 5D. A high resolution and magnification (Zoom factor=3, Pixel size=40 nm) of a single confocal slice of 0.3 µm through the nucleus of Δ55k infected SAECs cells at 36 h.p.i. (immunofluorescence of H3K9me3 in green and E4-ORF3 in red). The merged panel shows a zoom-in on the E4-ORF3 nuclear mesh and associated heterochromatin domains (inset).

Figure 6A:
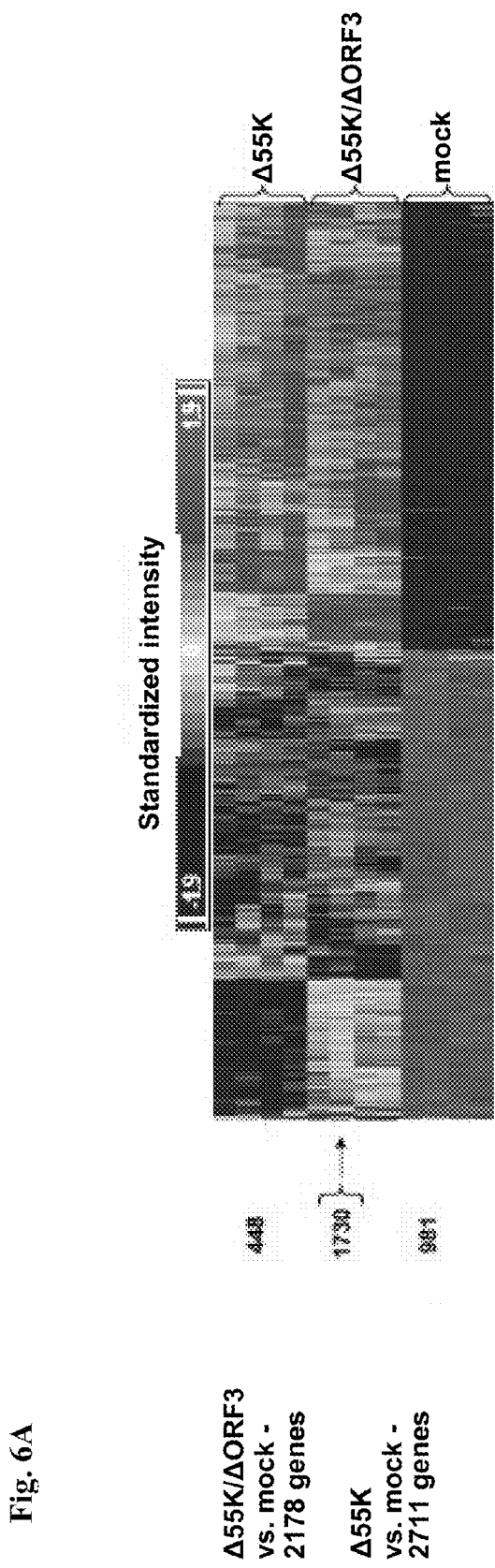
Figure 6B:
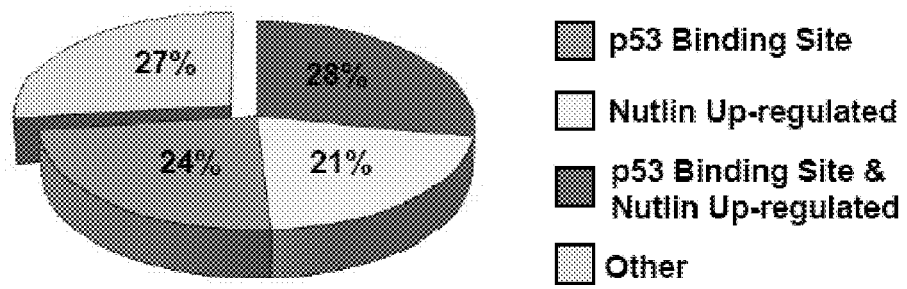
Figure 6C:
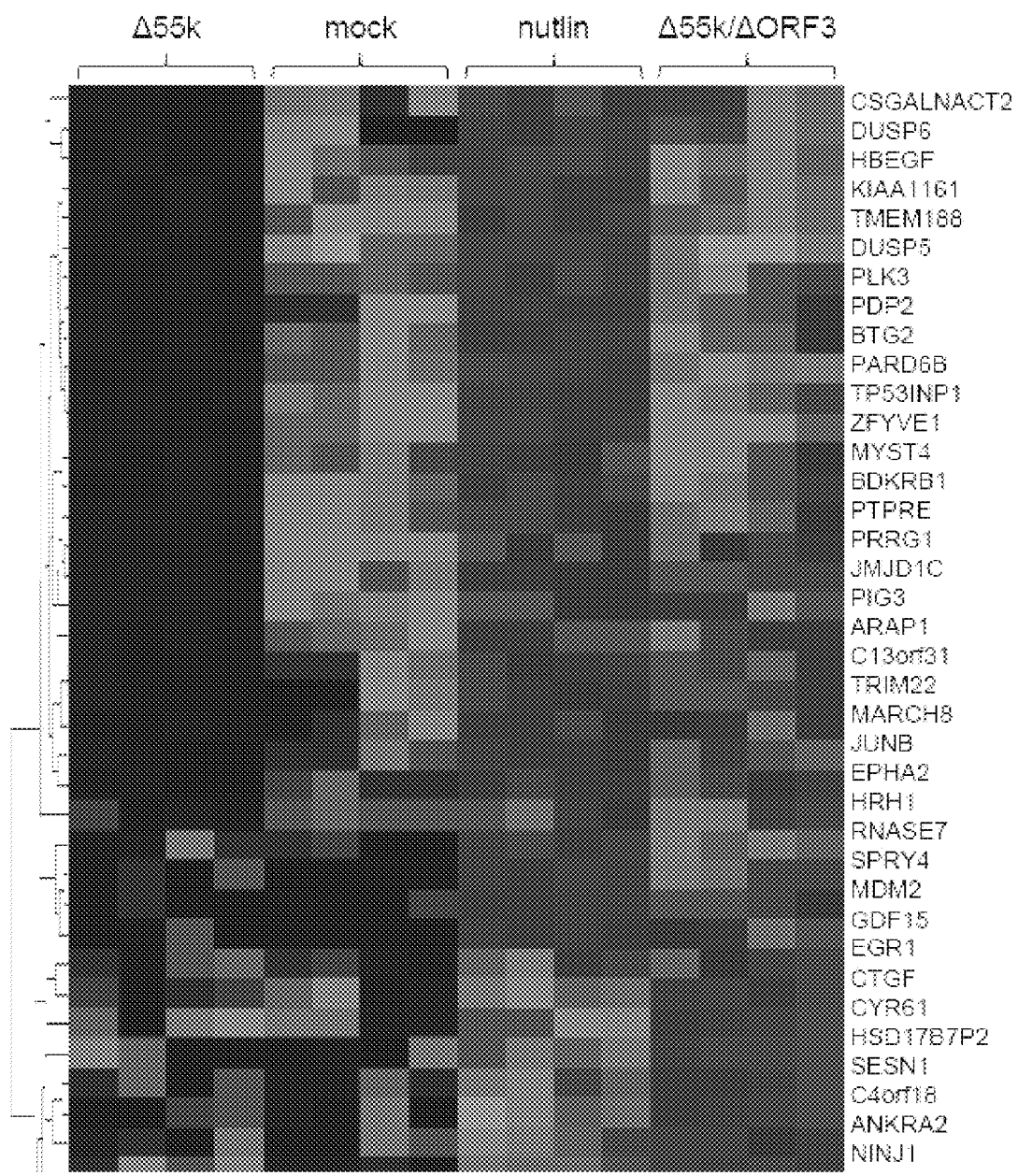
Figure 6D:
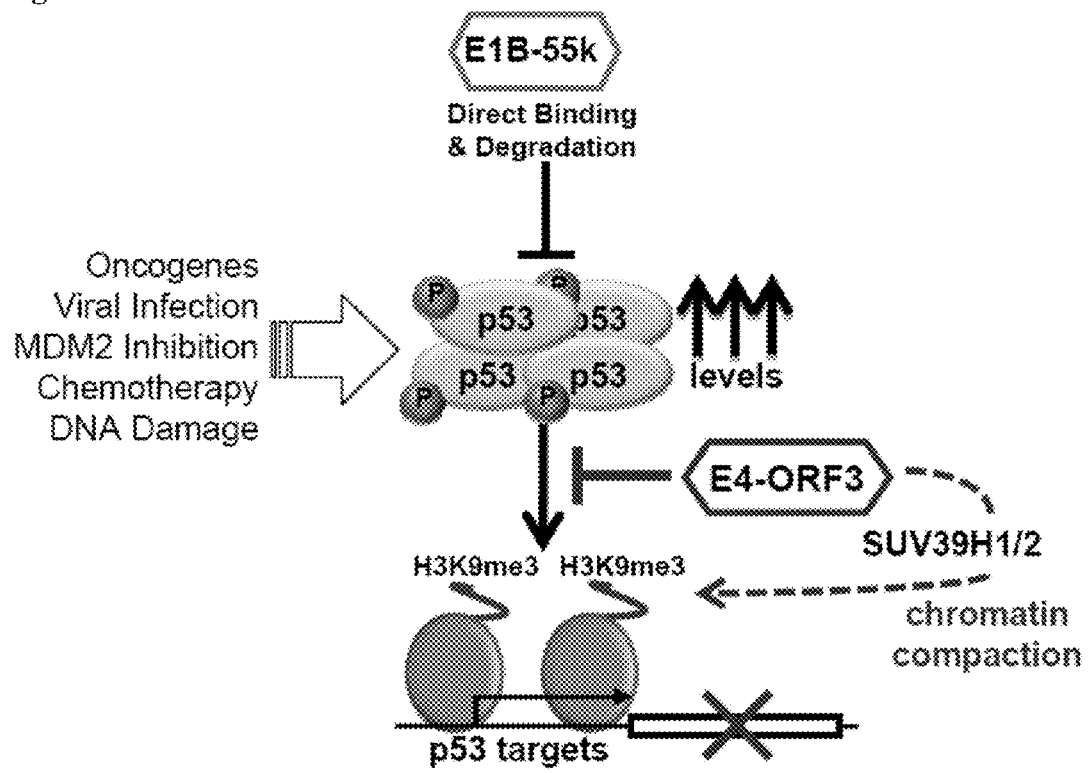

FIGS. 6A-6D. E4-ORF3 selectively silences p53 targets in the backdrop of the global transcriptional changes that drive oncogenic cellular and viral replication. FIG. 6A. Affymetrix expression arrays were used to analyze global gene expression changes in SAECs infected with either mock, Δ55k, or Δ55k/ΔORF3 viruses at 36 h.p.i. Expression analysis was also performed on nutlin treated SAECs as a positive control for p53 activation. Two independent experiments were performed with individual replicates for each condition. A Venn diagram showing the overlap (1730 genes) between the significant differentially expressed genes (log fold change (FC) of >2 or <−2 with a false discovery rate (FDR) of 0.05) in Δ55k/ΔORF3 versus mock infected SAECs (2711 genes) and Δ55k versus mock infected SAECs (2178 genes). A heat map with standardized intensity values for each of the 1730 overlapping genes in mock, Δ55k and Δ55k/ΔORF3 infected SAECs is shown on the right. FIG. 6B. There are 265 significant transcripts that are differentially upregulated (log FC>2 and FDR of 0.05) in Δ55k/ΔORF3 versus Δ55k infected SAECs. Of these 265 differentially upregulated genes, 72 genes have predicted p53 transcription factor binding sites (TFBS) in their promoters, 55 genes are upregulated by a log FC>1.5 in response to nutlin but do not have predicted p53 TFBS; and 62 genes have both a predicted p53 TFBS and are upregulated in response to nutlin. There are 76 other significant upregulated genes (gray) that do not fall into any of these aforementioned categories. FIG. 6C. Unsupervised hierarchical clustering of 46 of the top differentially upregulated transcripts in both Δ55k/ΔORF3 infection and nutlin treatment. FIG. 6D. The induction of p53 levels and phosphorylation in response to oncogenic and genotoxic stress is thought to determine p53 transcriptional activation. E1B-55k binds and degrades p53, which was thought to be critical for p53 inactivation in adenovirus replication. However, here we reveal that there is an additional adenoviral protein, E4-ORF3, which inactivates p53 via a novel and dominant epigenetic mechanism, irrespective of p53 stabilization and phosphorylation. E4-ORF3 forms a novel nuclear scaffold that directs SUV39H1/2 H3K9me3 repressive heterochromatin assembly at p53 target promoters. With access denied p53 is powerless to prevent viral replication.

Figure 7A:
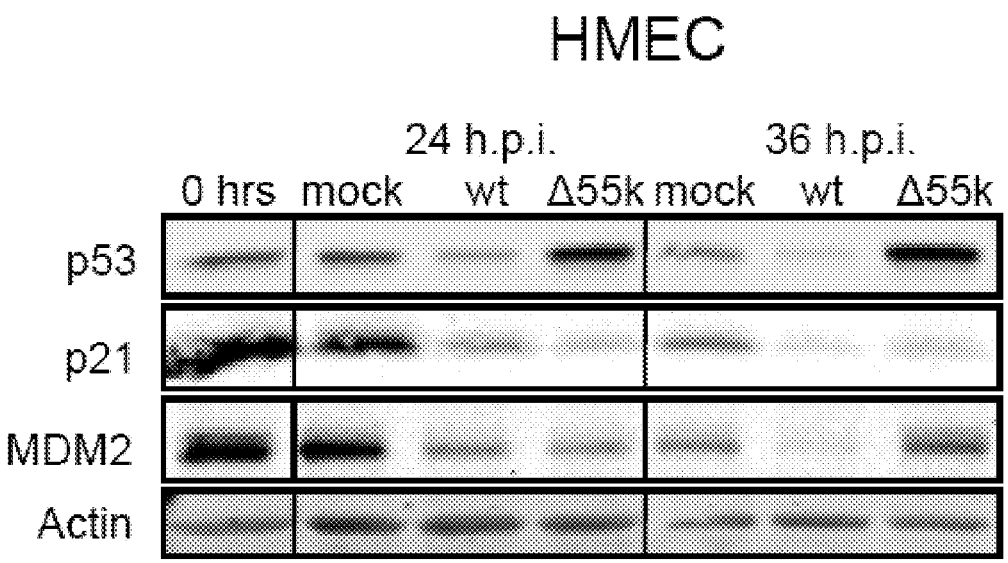
Figure 7B:
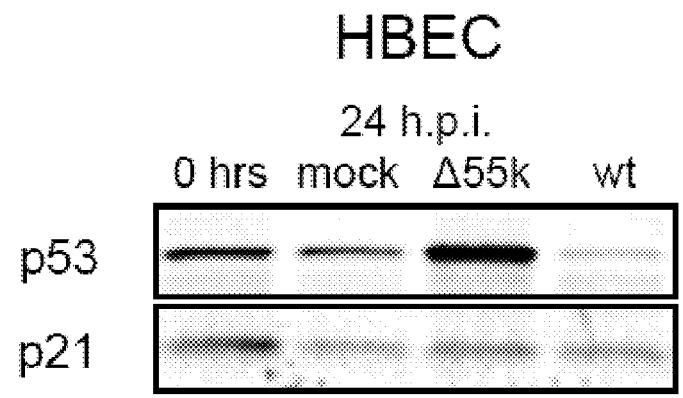

FIGS. 7A-7B. p53 is induced but not activated by the loss of p53 degradation in ΔE1B-55k infected human primary mammary epithelial cells or bronchial epithelial cells. FIG. 7A: Primary human mammary epithelial cells (HMEC) were infected with either mock, wild-type (wt), or ΔE1B-55k (Δ55k) viruses and harvested at 24 and 36 hours post infection (h.p.i.). Protein lysates were analyzed by Western blotting for the expression of p53, p21 and MDM2. Actin was analyzed as a loading control. FIG. 7B: Primary human bronchial epithelial cells (HBEC) were infected with mock, wt or Δ55k viruses, and harvested at 24 h.p.i. Protein lysates were analyzed by Western blotting for the expression of p53 and p21.

Figure 8:
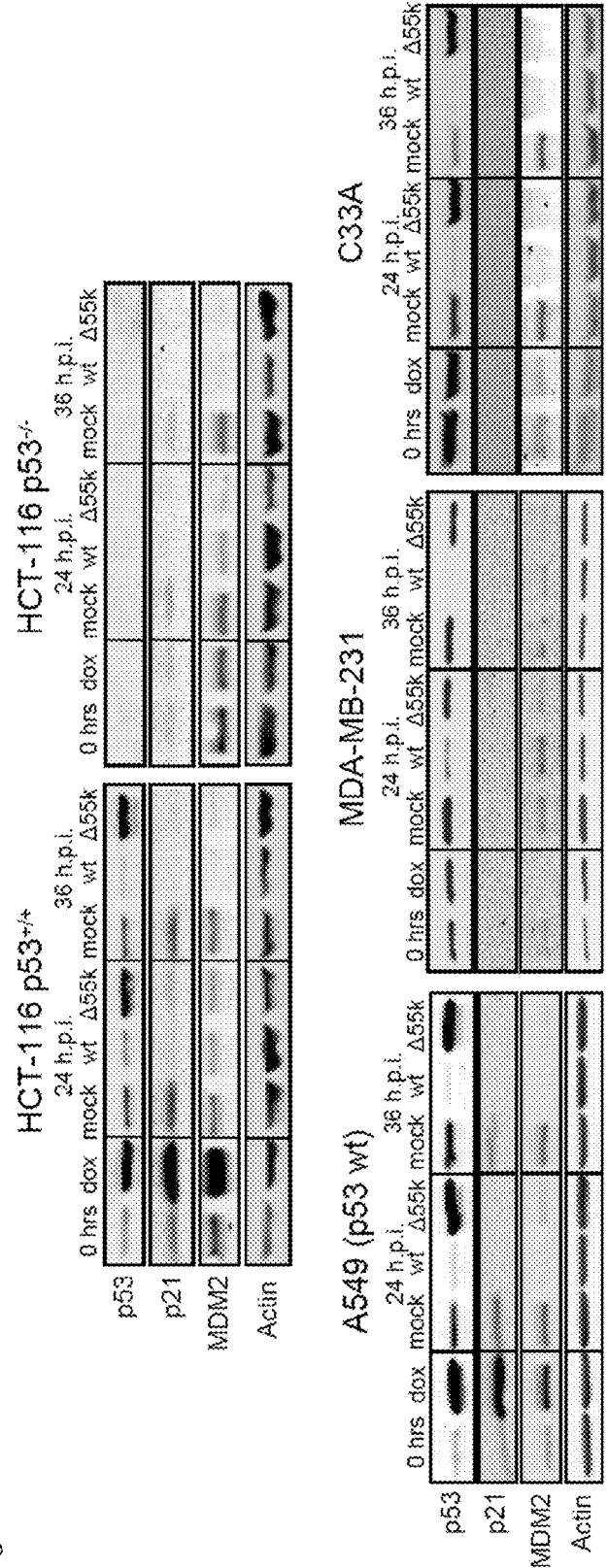

FIG. 8. The loss of E1B-55k induces p53 levels but not transcriptional targets in infected tumor cells. p53 wild-type (HCT-116 p53$^{+/+}$, A549) and p53 mutant tumor cell-lines (HCT-116 p53$^{-/-}$, MDA-MB-231 and C33A) were infected with either mock, wt or Δ55k viruses. Doxorubicin (dox) treatment was used as a positive control for p53 activation. Protein lysates were harvested at 24 and 36 h.p.i. and analyzed for the expression of p53, p21 and MDM2. Actin expression was analyzed as a loading control.

Figure 9:
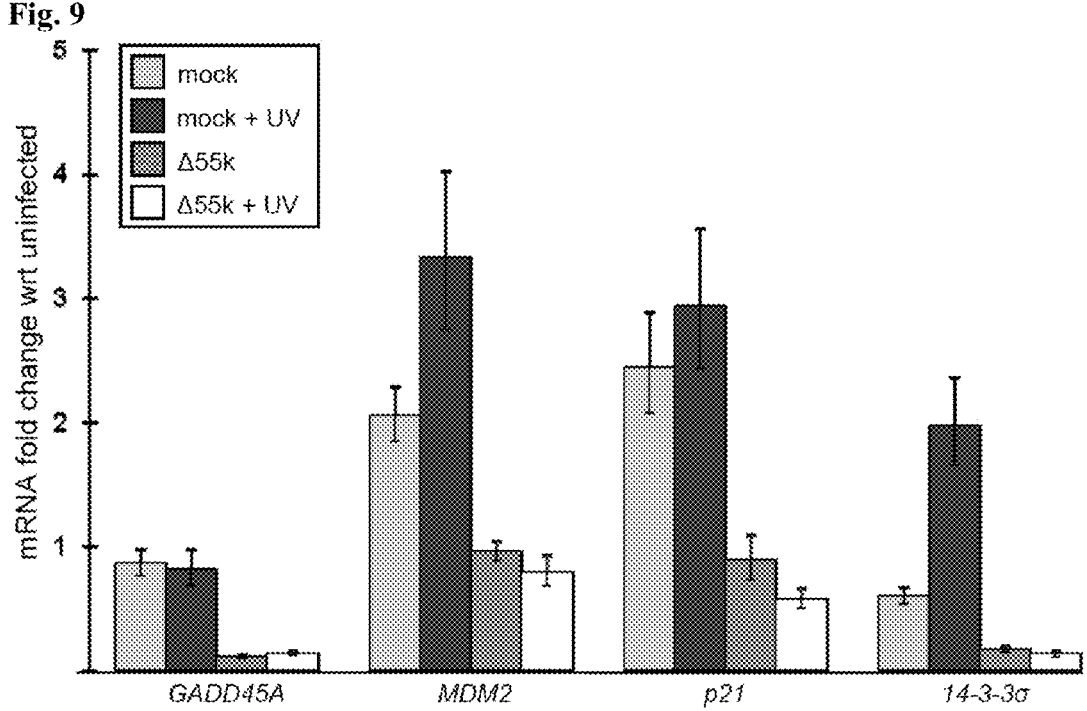

FIG. 9. UV irradiation fails to activate p53 transcriptional targets in ΔE1B-55k infected cells. Small airway epithelial cells were infected with either mock or Δ55k viruses and left untreated or irradiated with UV (13 J) at 24 h.p.i. Total RNA was isolated at 32 h.p.i. Real-Time PCR was used to quantify the mRNA level of p53 transcriptional targets, GADD45A, MDM2, p21 and 14-3-3σ. The fold change of mRNA levels with respect to (wt) uninfected cells is plotted; vertical bars represent the standard deviation across triplicates.

FIG. 10. Adenoviral genome map of early viral genes, together with their known cellular targets and functions.

Figure 11:
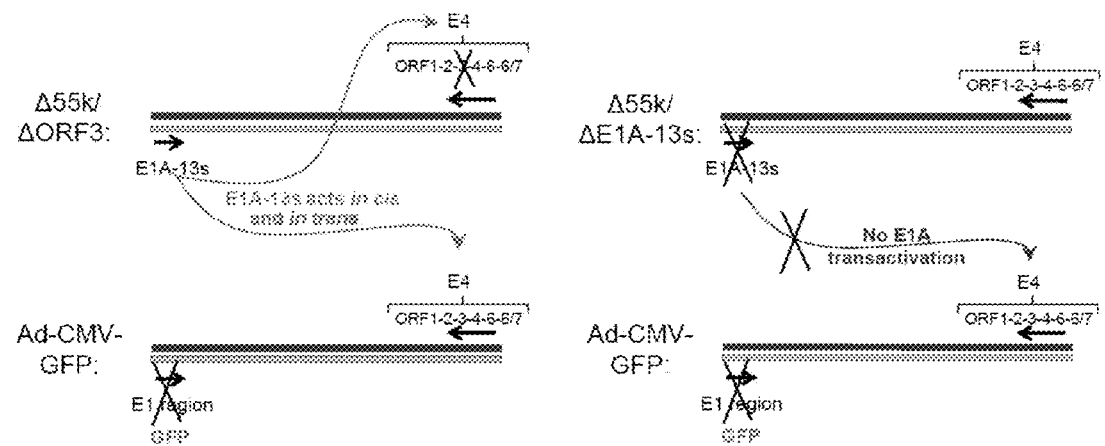

FIG. 11. E4-ORF3 expression in Ad-GFP is activated in trans by E1A-13s in Δ55k/ΔORF3 infection but not Δ55k/Δ13s infection (schematic to explain viral genome interactions and complementation experiment in FIG. 3B). Ad-GFP is a replication incompetent virus in which the CMV promoter drives the expression of GFP in the place of a deleted E1 region (Ad-CMV from Invitrogen). The Ad-CMV genome backbone includes the E4 transcriptional unit. The E4 genes (as well as other viral ORFs) are normally not expressed in Ad-CMV infection since they require E1A-13s for their transcriptional activation. However, when Ad-GFP is co-infected with Δ55k/ΔORF3 (as in FIG. 3b), the expression of E1A-13s in Δ55k/ΔORF3 infection can partially activate the transcription of Ad-GFP E4 genes in trans, including E4-ORF3 (left panel). In contrast, co-infection of Ad-GFP with Δ55k/Δ13s does not result in the activation of E4-ORF3 expression in either virus (right panel).

Figure 12:
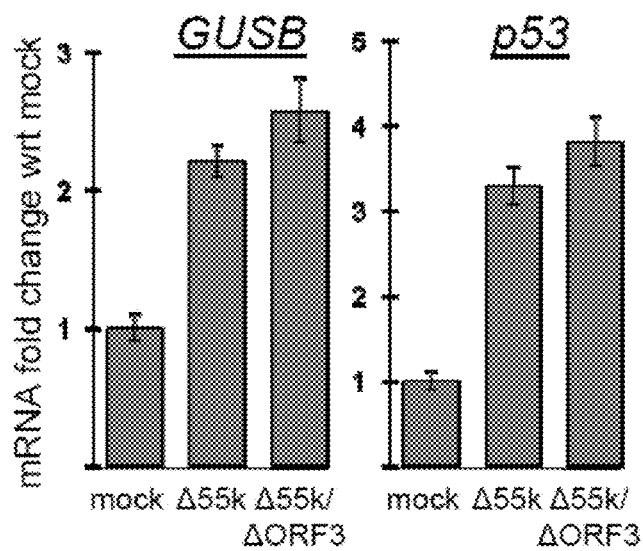

FIG. 12. The mRNA levels of non-p53 transcriptional target genes are similar in ΔE1B-55K infected cells, irrespective of E4-ORF3 expression. SAECs were infected with mock, Δ55k or Δ55k/ΔORF3 viruses. RNA was harvested at 36 h.p.i. Real-Time PCR was used to quantify the mRNA levels of the housekeeping gene, GUSB, and p53, which are induced by viral infection. mRNA levels are graphed as fold change with respect to (wrt) mock infected; vertical bars represent the standard deviation across triplicates.

Figure 13:
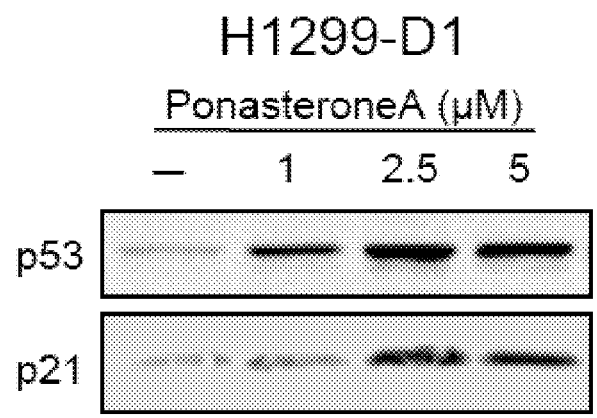

FIG. 13. H1299 (p53 null) stable cell-line (H1299-D1) with a ponasterone inducible p53 cDNA. H1299-D1 cells are a H1299 (p53 null) stable cell-line in which p53 cDNA expression is under the control of a ponasterone inducible promoter. Ponasterone A was added at 0, 1, 2.5 and 5 µM. Protein lysates were harvested after 16 hours and the expression of p53 and p21 analyzed by Western blotting.

Figure 14:
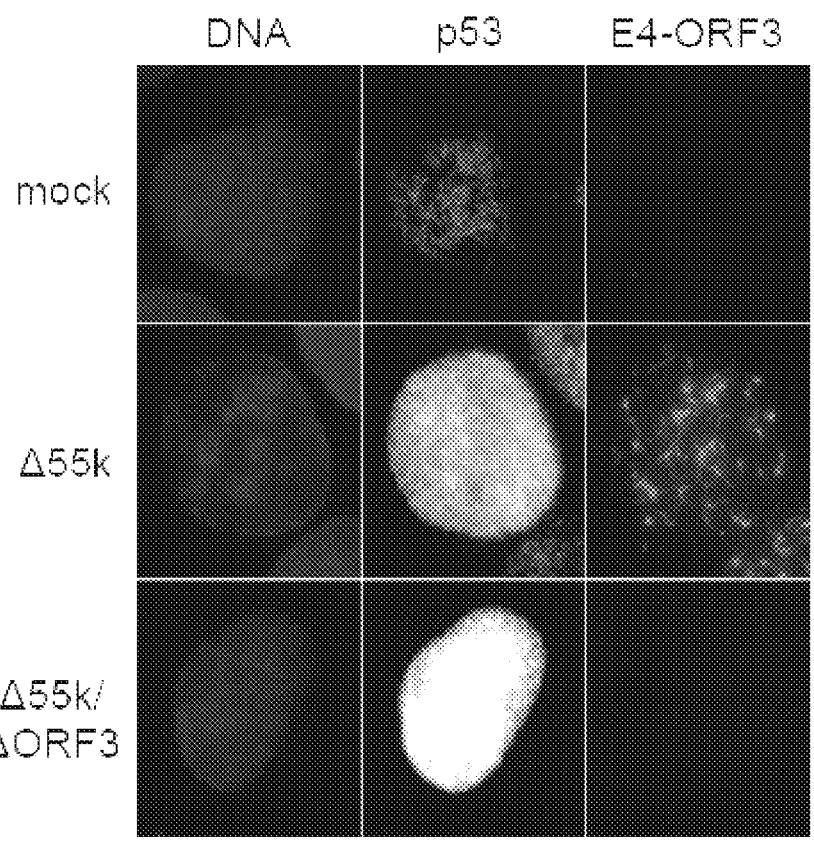

FIG. 14. E4-ORF3 does not co-localize with p53. U2OS cells were infected with mock, Δ55k or Δ55k/ΔORF3 virus and fixed at 28 h.p.i. p53 and E4-ORF3 were detected by immunofluorescence and DNA counterstained with Hoechst.

Figure 15:
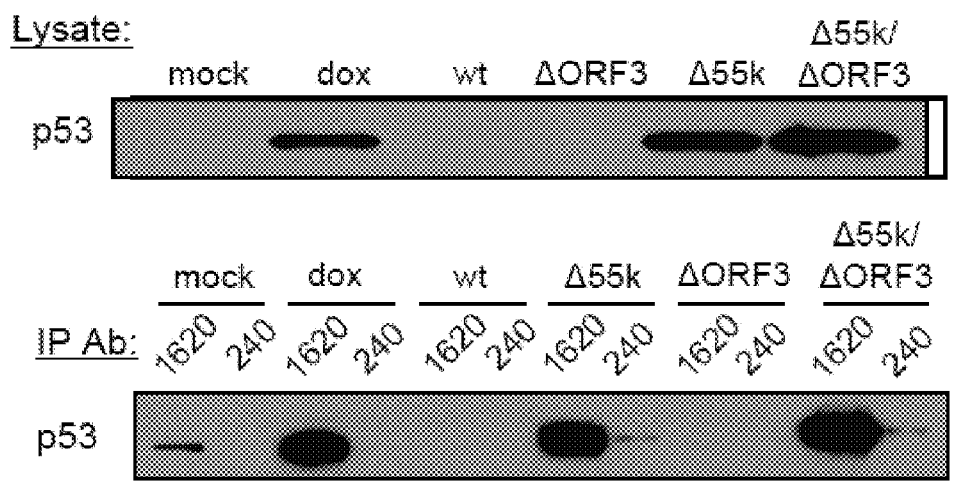

FIG. 15. p53 has a wild-type and active DNA binding domain protein conformation in the presence of E4-ORF3. SAECs were infected with mock, wt, ΔORF3, Δ55k or Δ55k/ΔORF3 viruses. Doxorubicin (dox) treatment was used as a positive control for p53 activation. p53 was immunoprecipitated from lysates with the p53 conformation specific antibodies PAb 1620 and PAb 240. Lysates and immunoprecipitates were Western blotted for p53.

FIG. 16. In contrast to p53-luc (FIG. 4a), a control pGL3-luciferase reporter plasmid is activated to similar levels in wild-type, Δ55k and Δ55k/ΔORF3 infection. U2OS cells were transfected (in triplicate) with either a p53-luciferase reporter (p53-luc), a p53-luciferase reporter in which the p53 binding sites are mutated (p53-mutant) or control pGL3-luciferase (pGL3-luc) plasmids. Transfected cells were infected with either wt, Δ55k or Δ55k/ΔORF3 viruses and D-Luciferin added at 4 hours post infection. Luminescence readings were taken every hour for 48 hours. The average luminescence across triplicates is plotted against time in hours post infection (h.p.i.). The luminescence readings for the control pGL3-luciferase transfections are shown above (p53-luc data is in FIG. 4a for the same experiment).

Figure 17:
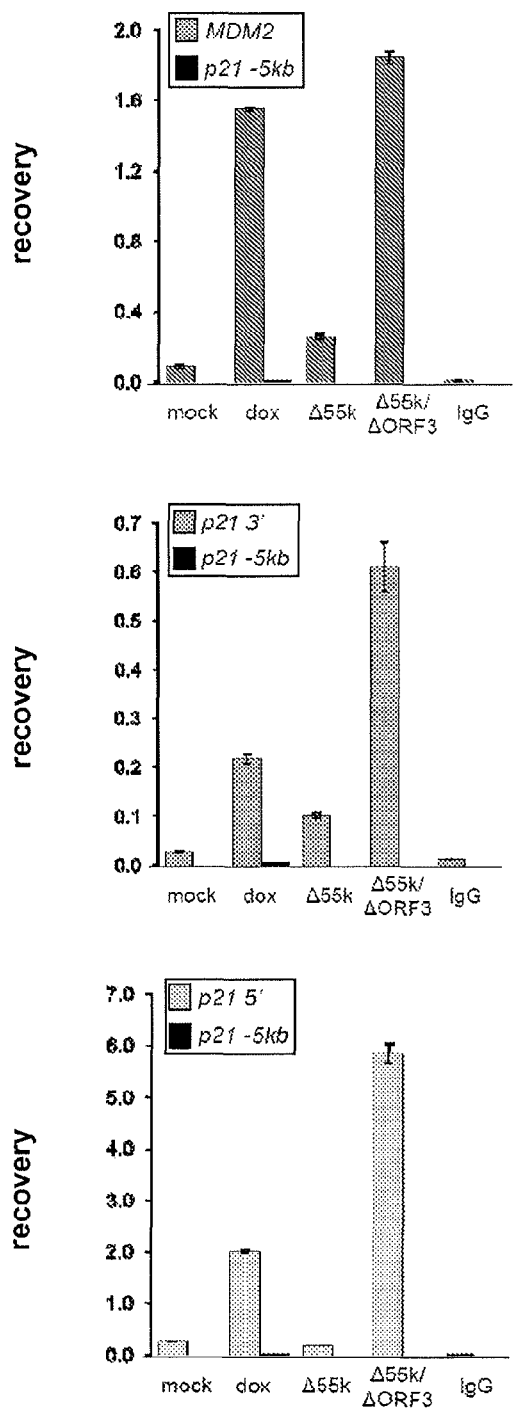

FIG. 17. E4-ORF3 prevents p53 binding to target promoters in cellular chromatin. Using p53 monoclonal antibodies, p53 chromatin immunoprecipitations (ChIP) were performed at 36 h.p.i. in U2OS cells infected with mock, Δ55k or Δ55k/ΔORF3 viruses. Doxorubicin was used as positive control. A matched IgG isotype was used as a control for specificity. ChIP samples were analyzed by Real-Time Quantitative PCR for p21 (5' and 3' p53 binding sites) and MDM2 promoter sequences and normalized relative to input DNA. The % recovery for p53 and IgGChIPs are plotted on the y-axis. The recovery in IgG controls is a measure of background. The −5 kb region of the p21 promoter does not contain p53 binding sequences and was used as a negative control.

Figure 18:
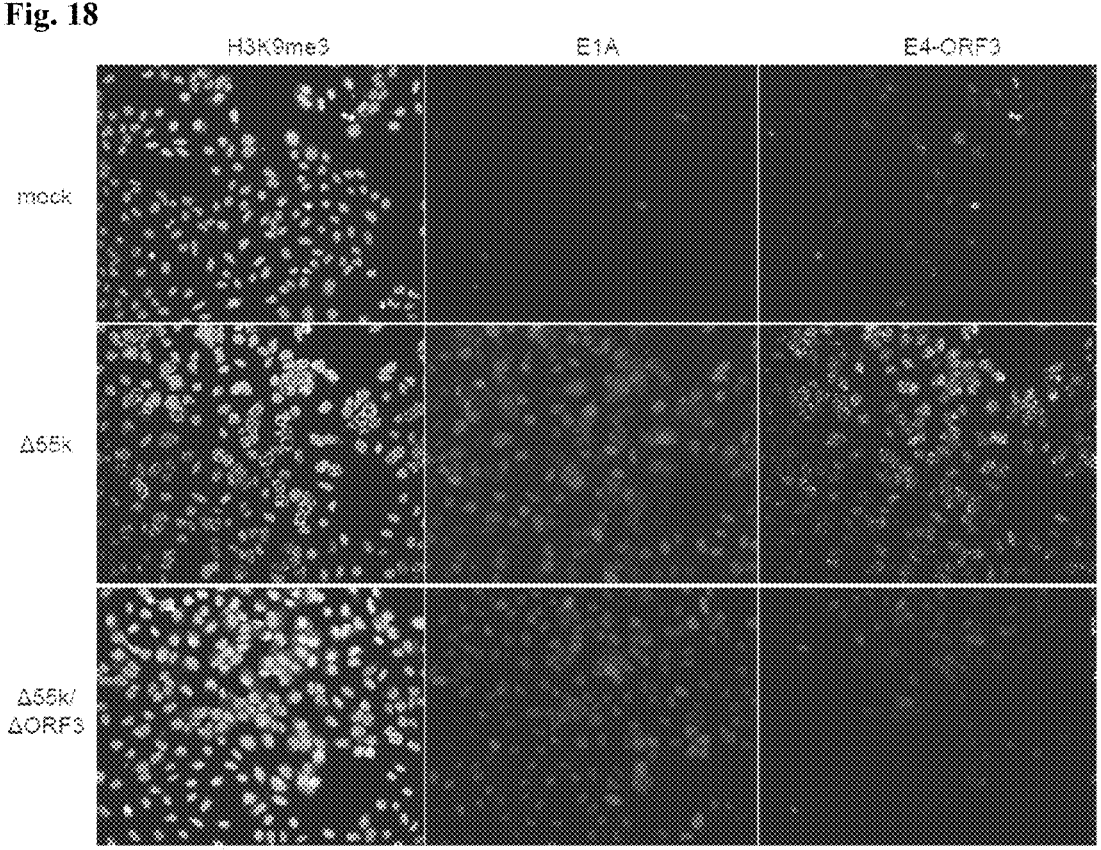

FIG. 18. H3K9me3 heterochromatin domains are induced at the periphery of the nucleus in Δ55k infection but not Δ55k/ΔORF3. (Control for infection in FIG. 4D) U2OS cells were infected with either mock, Δ55k or Δ55k/ΔORF3 viruses and fixed at 36 hours post infection. H3K9 trimethyl (H3K9me3), E1A (adenoviral early protein expressed in both Δ55k and Δ55k/ΔORF3 infection) and E4-ORF3 (white) were detected by immunofluorescence. DNA was counterstained with Hoechst. Images were acquired with a Zeiss Axioplan 2 microscope.

Figure 19A:
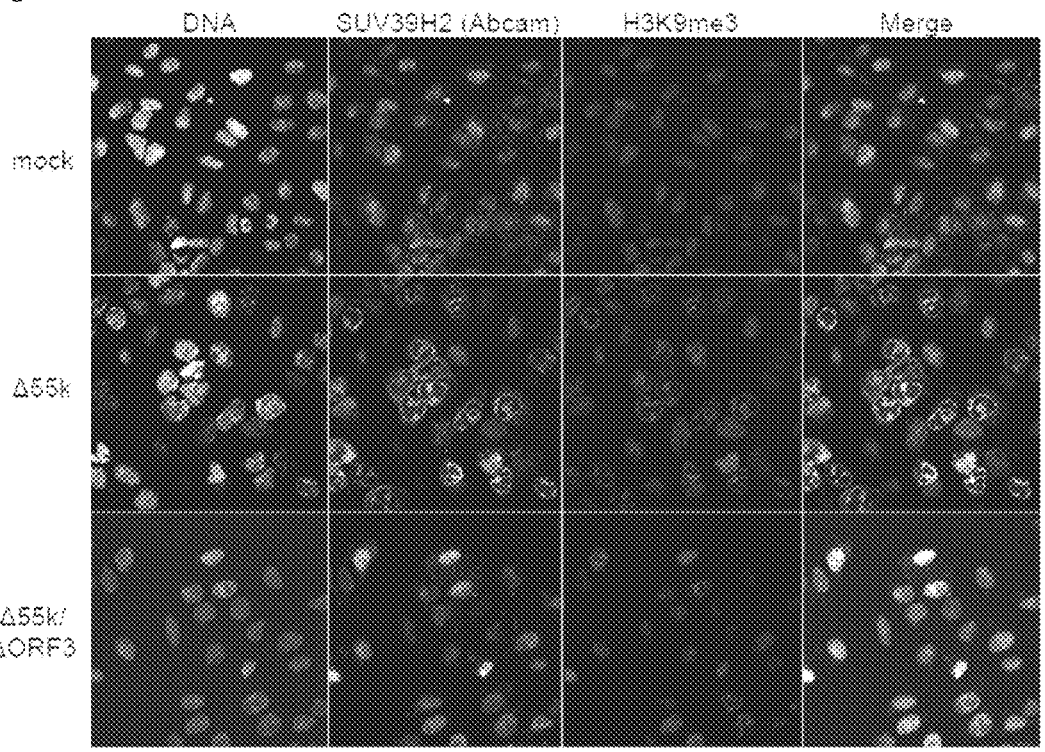
Figure 19B:
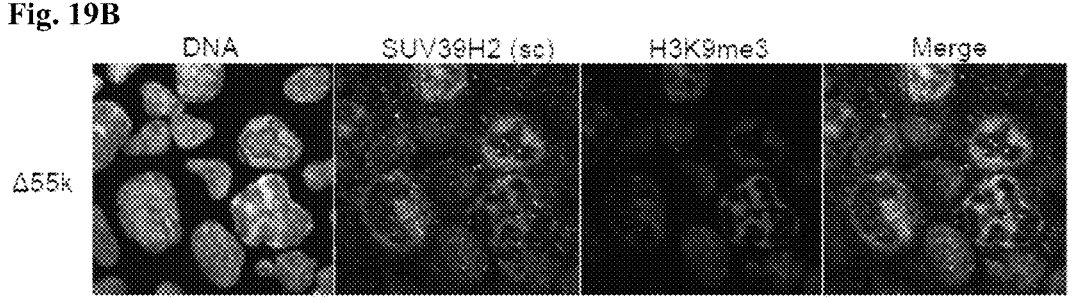
Figure 19C:
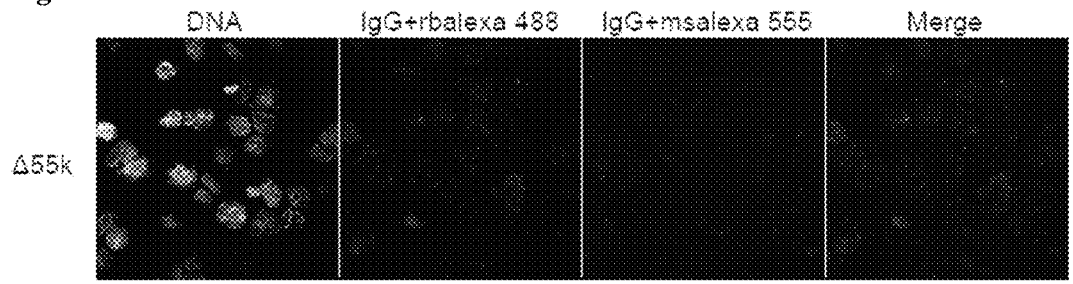

FIGS. 19A-19C. The methyltransferase SUV39H2 specifically co-localizes with dense cellular DNA and H3K9 trimethyl in Δ55k infected cells. (Control for FIG. 4E) U2OS cells were infected with either mock, Δ55k or Δ55k/ΔORF3 viruses and fixed at 36 h.p.i. FIG. 19A. Immunofluorescence was performed with antibodies raised against SUV39H2 (Abcam) and H3K9 trimethyl (H3K9me3). DNA was stained with Hoechst (white). FIG. 19B. Immunofluorescence with a second independent antibody raised against SUV39H2 (sc, Santa Cruz Biotechnology) and co-stained with H3K9me3 to confirm SUV39H2 re-localization. FIG. 19C. IgG isotype and secondary antibody controls for SUV39H2 and H3K9me3 immunofluorescence. Images were acquired with a Leica confocal SP2 microscope.

Figure 20A:
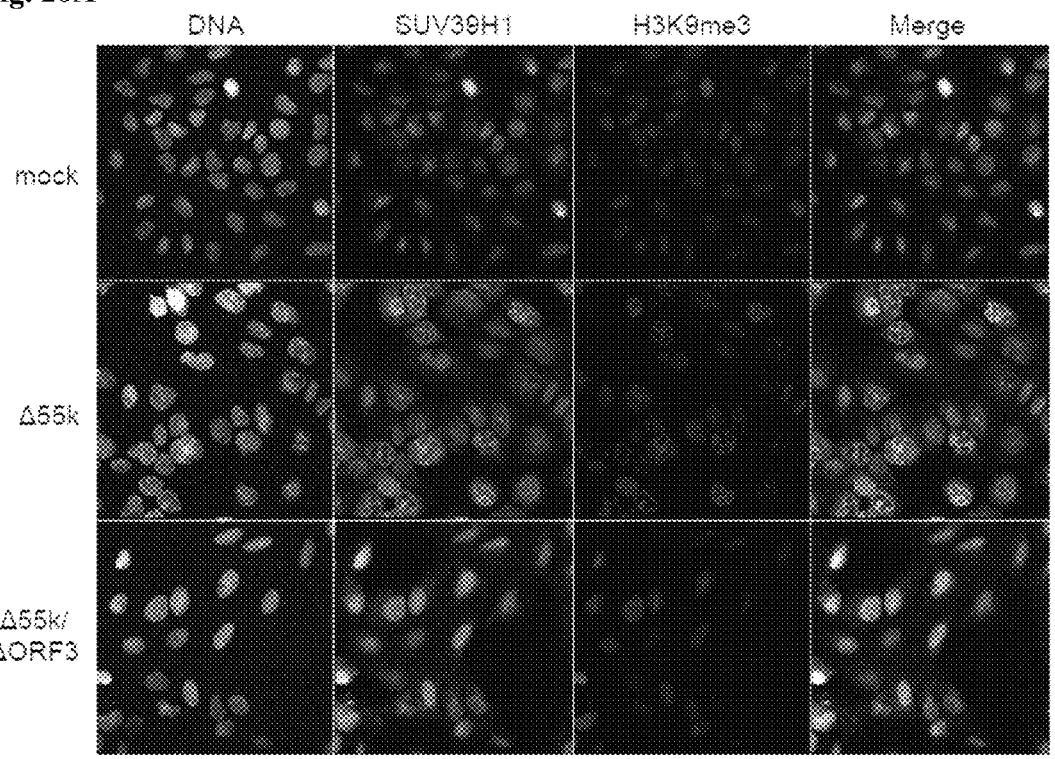
Figure 20B:
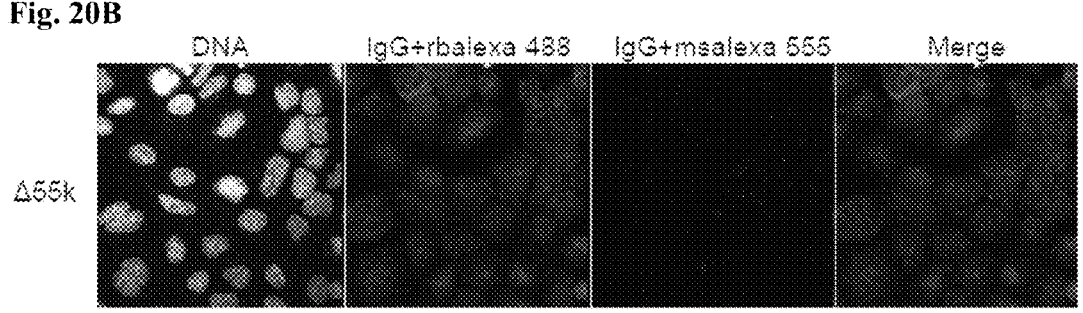
Figure 20C:
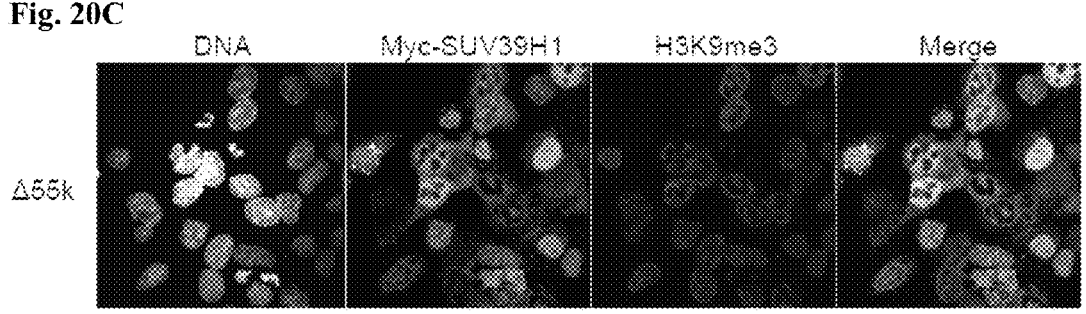

FIGS. 20A-20C. The methyltransferase SUV39H1 specifically co-localizes with dense cellular DNA and H3K9 trimethyl in Δ55k infected cells. (Control for FIG. 4E) U2OS cells were infected with either mock, Δ55k or Δ55k/ΔORF3 viruses and fixed at 36 h.p.i. FIG. 20A. Immunofluorescence was performed with antibodies raised against SUV39H1 and H3K9 trimethyl (H3K9me3). DNA was stained with Hoechst (white). FIG. 20B. IgG isotype and secondary antibody controls. FIG. 20C. To confirm the results with the endogenous SUV39H1 antibody, U2OS cells were transfected with a myc-tagged SUV39H1 expression construct, infected with Δ55k virus and fixed at 36 h.p.i. Myc-tagged SUV39H1 and H3K9me3 were detected by immunofluorescence, DNA was counterstained with Hoechst (white). Images were acquired with a Leica confocal SP2 microscope.

Figure 21:
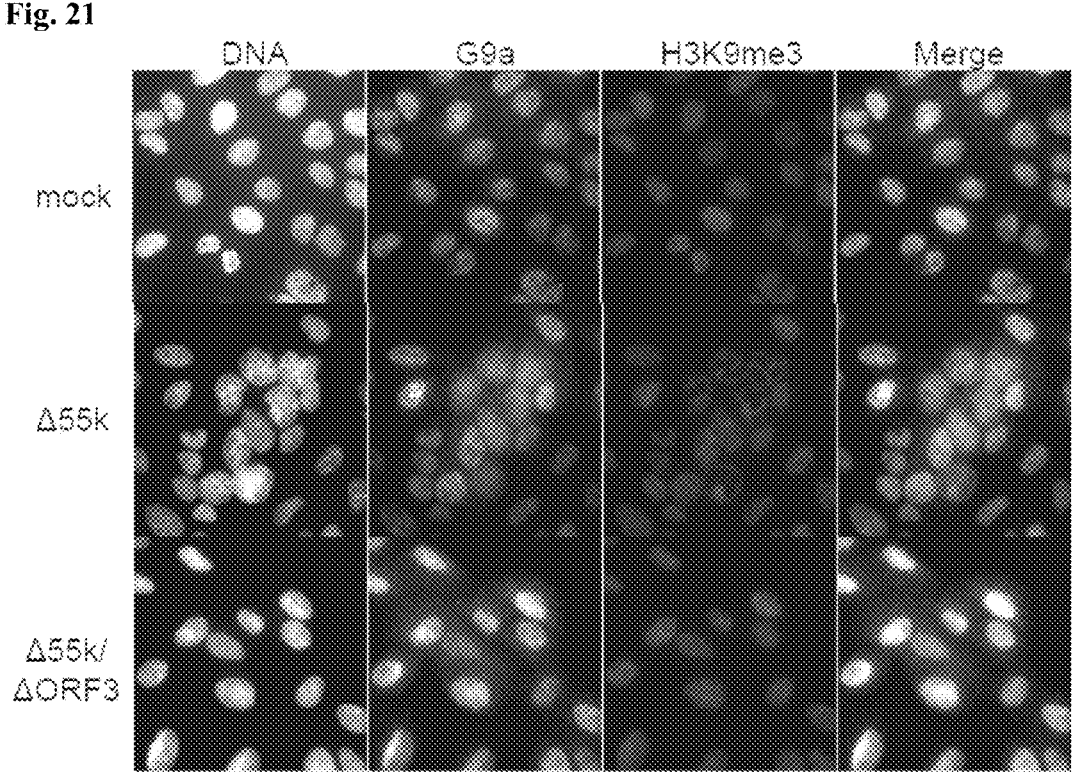

FIG. 21. The methyltransferase G9a does not co-localize with dense cellular DNA or H3K9 trimethyl in Δ55k infected cells. (Control for FIG. 4E) U2OS cells were infected with either mock, Δ55k or Δ55k/ΔORF3 viruses and fixed at 36 h.p.i. Immunofluorescence was performed with antibodies raised against G9a and H3K9 trimethyl (H3K9me3). DNA was counterstained with Hoechst (white). Images were acquired with an Axioplan microscope.

Figure 22:
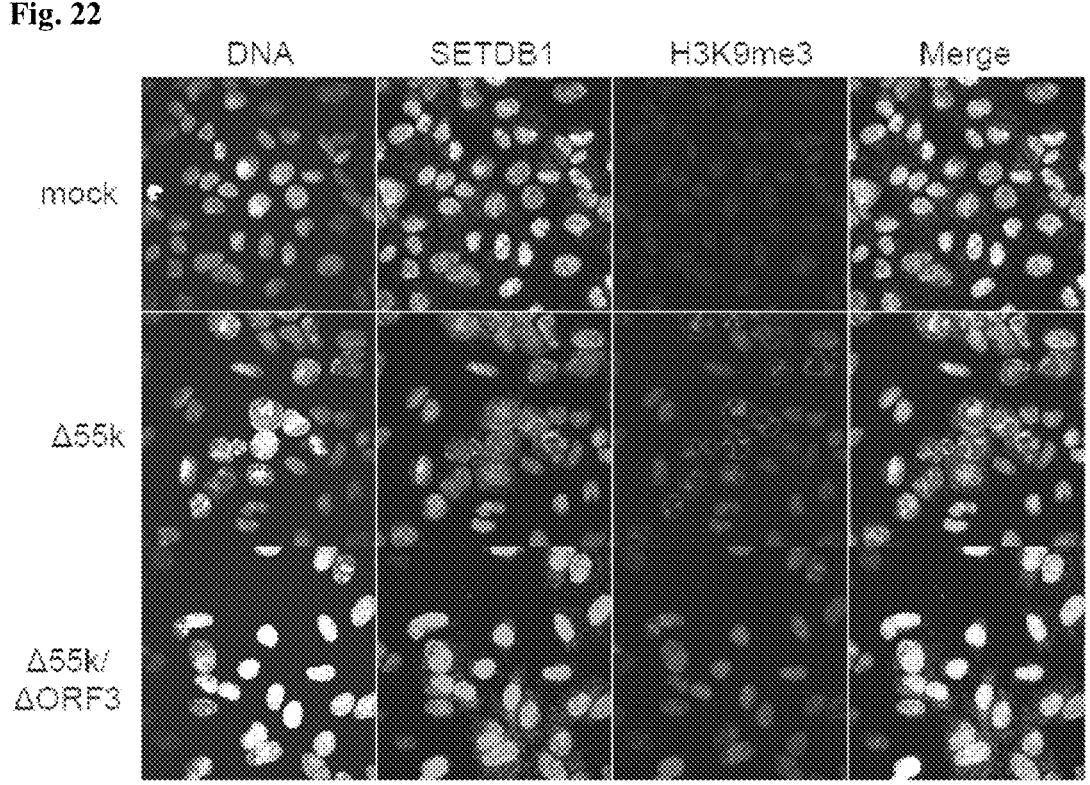

FIG. 22. The methyltransferase SETDB1 does not co-localize with dense cellular DNA or H3K9 trimethyl in Δ55k infected cells. (Control for FIG. 4E) U2OS cells were infected with either mock, Δ55k or Δ55k/ΔORF3 viruses and fixed at 36 h.p.i. Immunofluorescence was performed with antibodies raised against SETDB1 and H3K9 trimethyl (H3K9me3). DNA was stained with Hoechst (white). Images were acquired with a Nikon A1 confocal microscope.

Figure 23A:
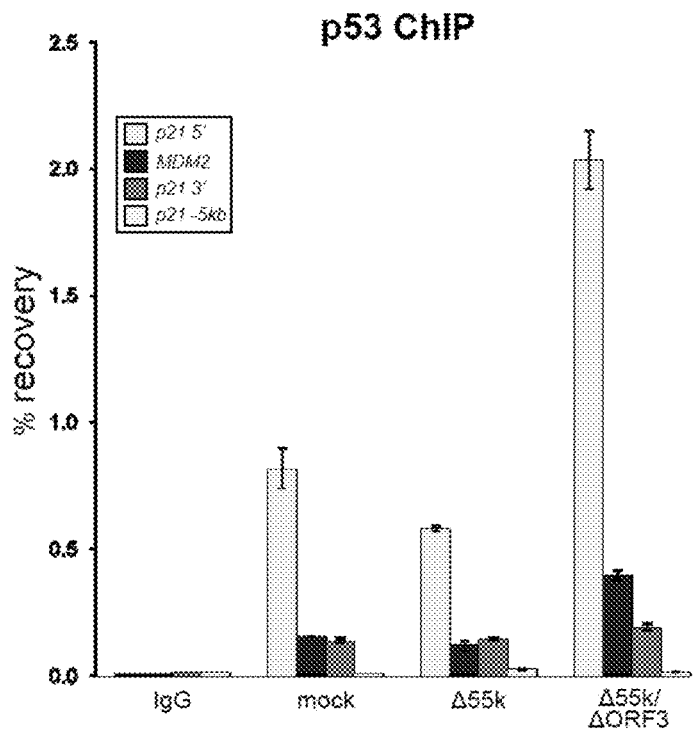
Figure 23B:
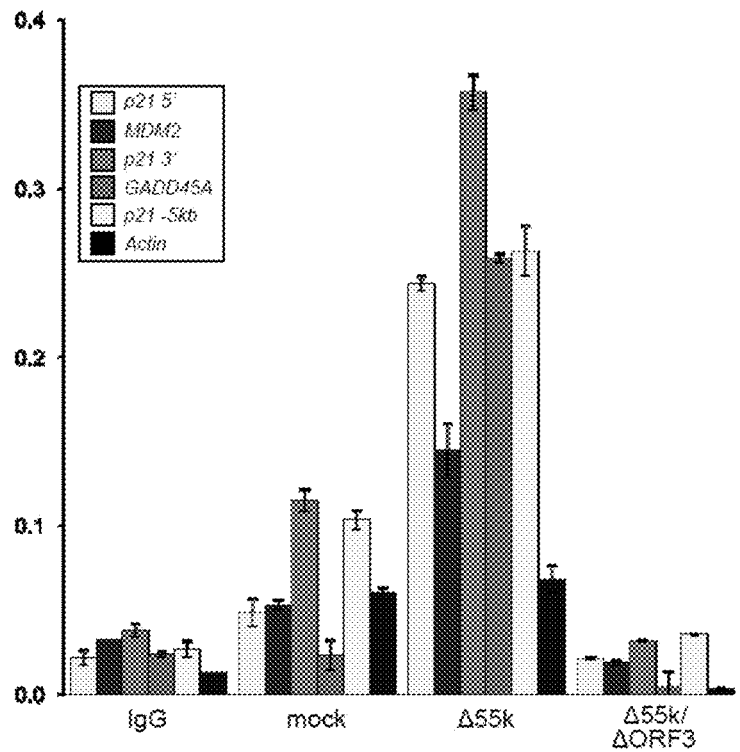

FIG. 23A-23B. E4-ORF3 induces H3K9 trimethyl at p53 target promoters, preventing p53 DNA binding (results in FIG. 5A plotted as % recovery). U2OS cells infected with mock, Δ55k or Δ55k/ΔORF3 viruses and harvested at 36 h.p.i. Using p53 (FIG. 23A) or H3K9 trimethyl (H3K9me3) (FIG. 23B) antibodies, chromatin immunoprecipitations (ChIPs) were performed. A non-immune rabbit IgG was used as a negative control. Real-Time Quantitative PCR was performed for p21 (5' and 3' p53 binding sites), MDM2, GADD45A and Actin promoter sequences. All results have been normalized relative to input DNA. The −5 kb region of the p21 promoter is a negative control for p53 binding.

Figure 24:
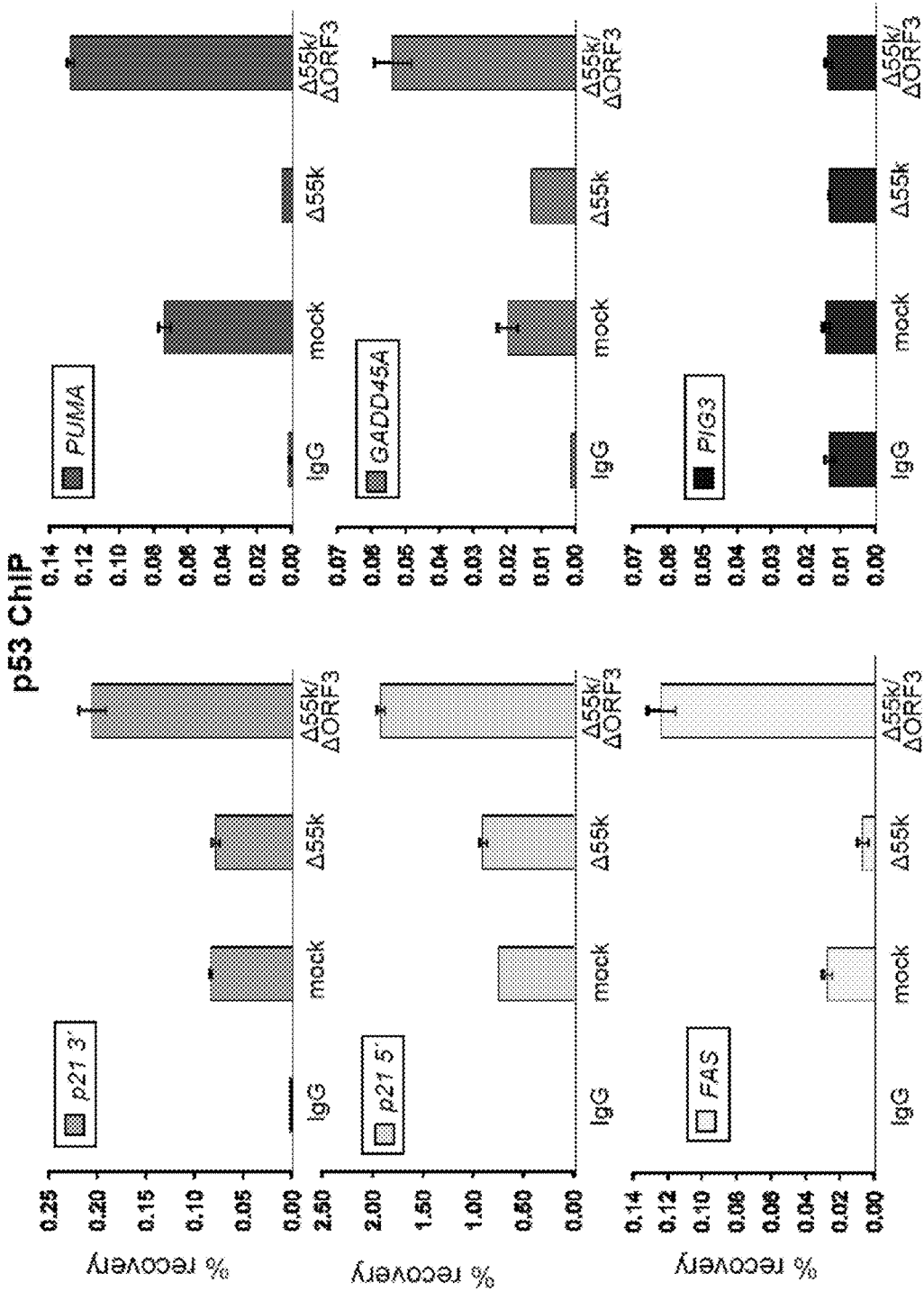

FIG. 24. E4-ORF3 inactivates p53 by preventing p53 DNA binding to the promoters of multiple p53 target promoters. U2OS cells infected with mock, Δ55k or Δ55k/ΔORF3 viruses were harvested at 36 h.p.i. To extend the panel of p53 target promoters in FIG. 5A, p53 chromatin immunoprecipitation (ChIP) was performed using a p53 antibody or a non-immune mouse IgG control. ChIP samples were analyzed by Real-Time Quantitative PCR. Analysis of p21 5' and 3' p53 binding sites confirm ChIP results as in FIG. 23, and in addition, FAS, PUMA, GADD45A, and PIG3 promoters were analyzed with results normalized relative to input DNA. The % recovery for the p53 ChIP is plotted on the y-axis. The recovery in the IgG controls is a measure of background.

Figure 25:
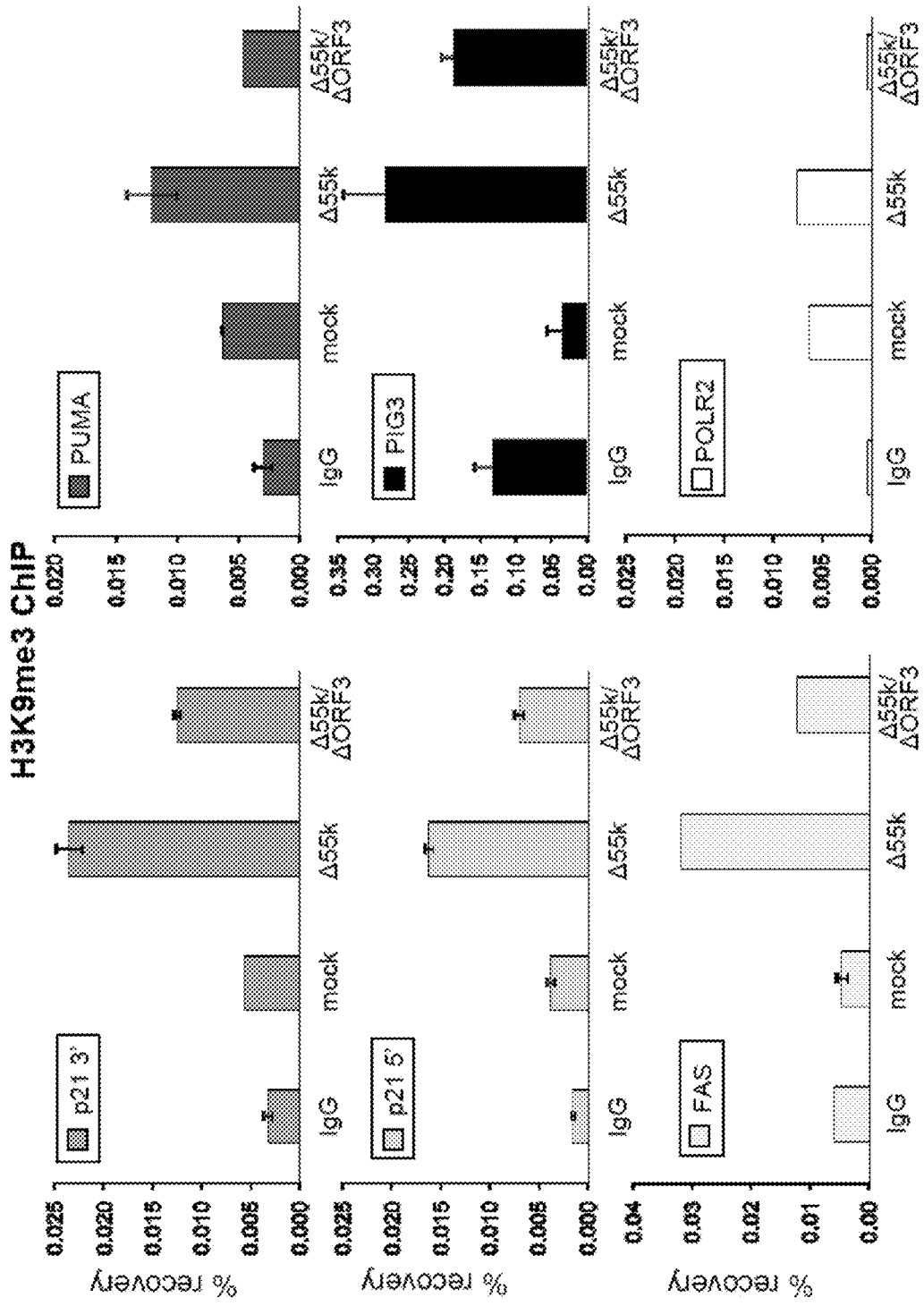

FIG. 25. E4-ORF3 induces H3K9 trimethyl at p53 target promoters in Δ55k infection. U2OS cells infected with mock, Δ55k or Δ55k/ΔORF3 viruses were harvested at 36 h.p.i. To extend the panel of p53 target promoters and control of FIG. 5A, H3K9me3 chromatin immunoprecipitation (ChIP) was performed using an H3K9 trimethyl (H3K9me3) antibody or a non-immune mouse IgG control. ChIP samples were analyzed by Real-Time Quantitative PCR. Analysis of p21 5' and 3' p53 binding sites confirms ChIP results in FIG. 23. In addition, p53 targets FAS, PUMA, and PIG3 promoters were analyzed. POLR2, a non-p53 target, was used as a negative control. Results were normalized relative to input DNA. The % recovery for the H3K9me3 ChIP is plotted on the y-axis.

Figure 26:
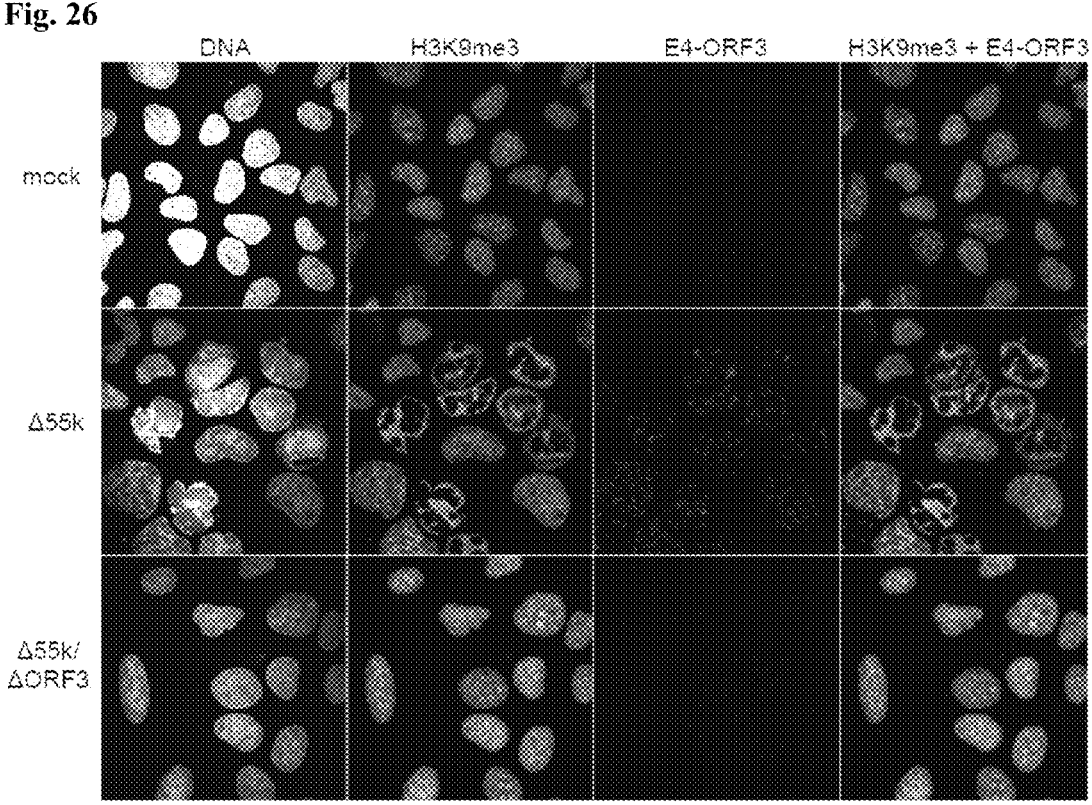

FIG. 26. E4-ORF3 is directly associated with H3K9 trimethyl heterochromatin formation in the nuclei of U2OS. (Control for FIG. 5B) U2OS cells were infected with either mock, Δ55k or Δ55k/ΔORF3 viruses and fixed at 36 h.p.i. Immunofluorescence was performed with antibodies raised against E4-ORF3 and H3K9 trimethyl (H3K9me3). DNA is stained with Hoechst (white). Images acquired with a Nikon A1 confocal microscope.

Figure 27:
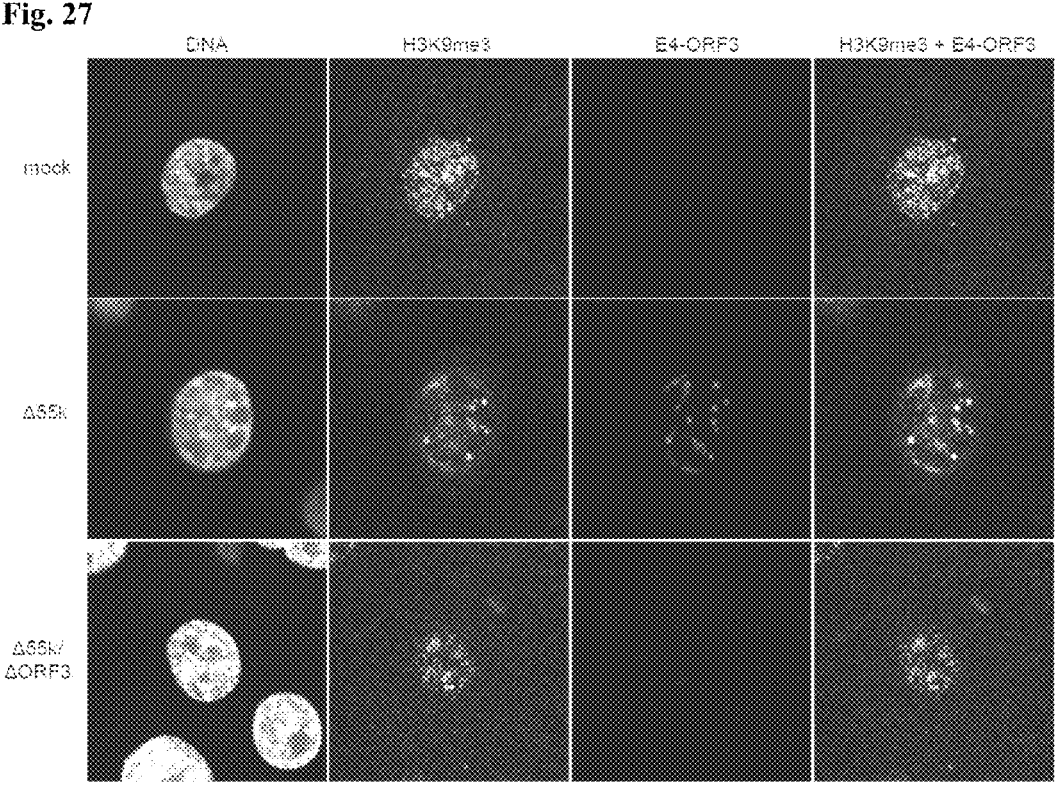

FIG. 27. E4-ORF3 is directly associated with H3K9 trimethyl heterochromatin formation in the nuclei of SAECs. (Control for high resolution images acquired for FIG. 5C) Small airway epithelial cells (SAECs) were infected with either mock, Δ55k or Δ55k/ΔORF3 viruses and fixed at 36 h.p.i. Immunofluorescence was performed with antibodies raised against E4-ORF3 and H3K9 trimethyl (H3K9me3). DNA is stained with Hoechst (white). Images acquired with a Leica confocal SP2 microscope.

FIG. 28. Lysates from two independent experiments in SAECs from which RNA was harvested to perform whole genome expression analysis. Two independent experiments (I and II) with different batches of cells were performed as indicated. Small airway epithelial cells were infected with either mock, wild-type (wt), ΔE1B-55k (Δ55k) or ΔE1B-55k/ΔE4-ORF3 (Δ55k/ΔORF3) viruses and harvested at 36 hours post infection for lysates. Nutlin treatment for 12 hours was used as a positive control for p53 activation. RNA was harvested and purified for mock, Δ55k, Δ55k/ΔORF3 and nutlin samples (in duplicate for each experiment), then labeled and hybridized with Affymetrix exon arrays to perform genome-wide expression analyses.

Figure 29:
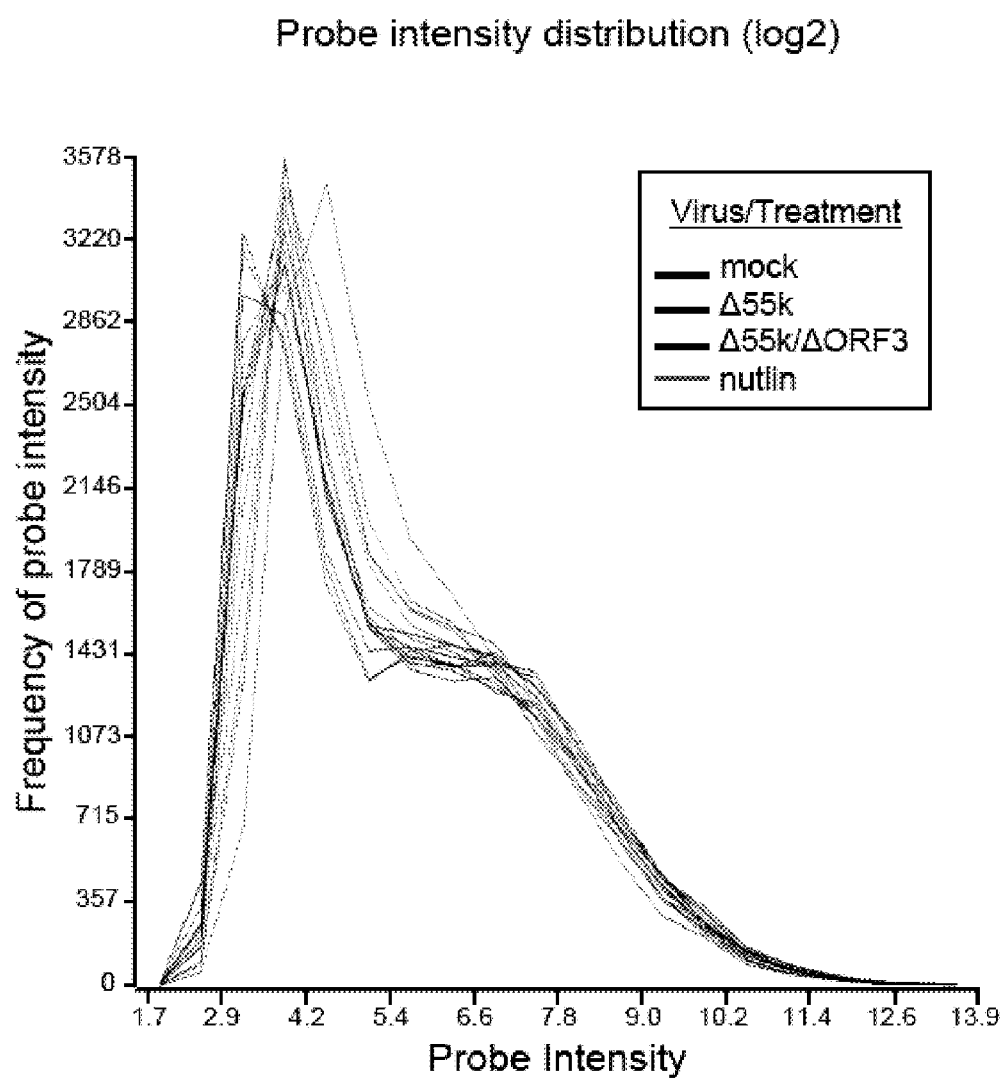

FIG. 29. Probe intensity distributions of Affymetrix arrays. Probe intensity distributions of Affymetrix exon array chips hybridized with mock, ΔE1B-55k (Δ55k), ΔE1B-55k/ΔE4-ORF3 (Δ55k/ΔORF3) and nutlin treated SAEC samples (4 independent replicates for each condition).

Figure 30:
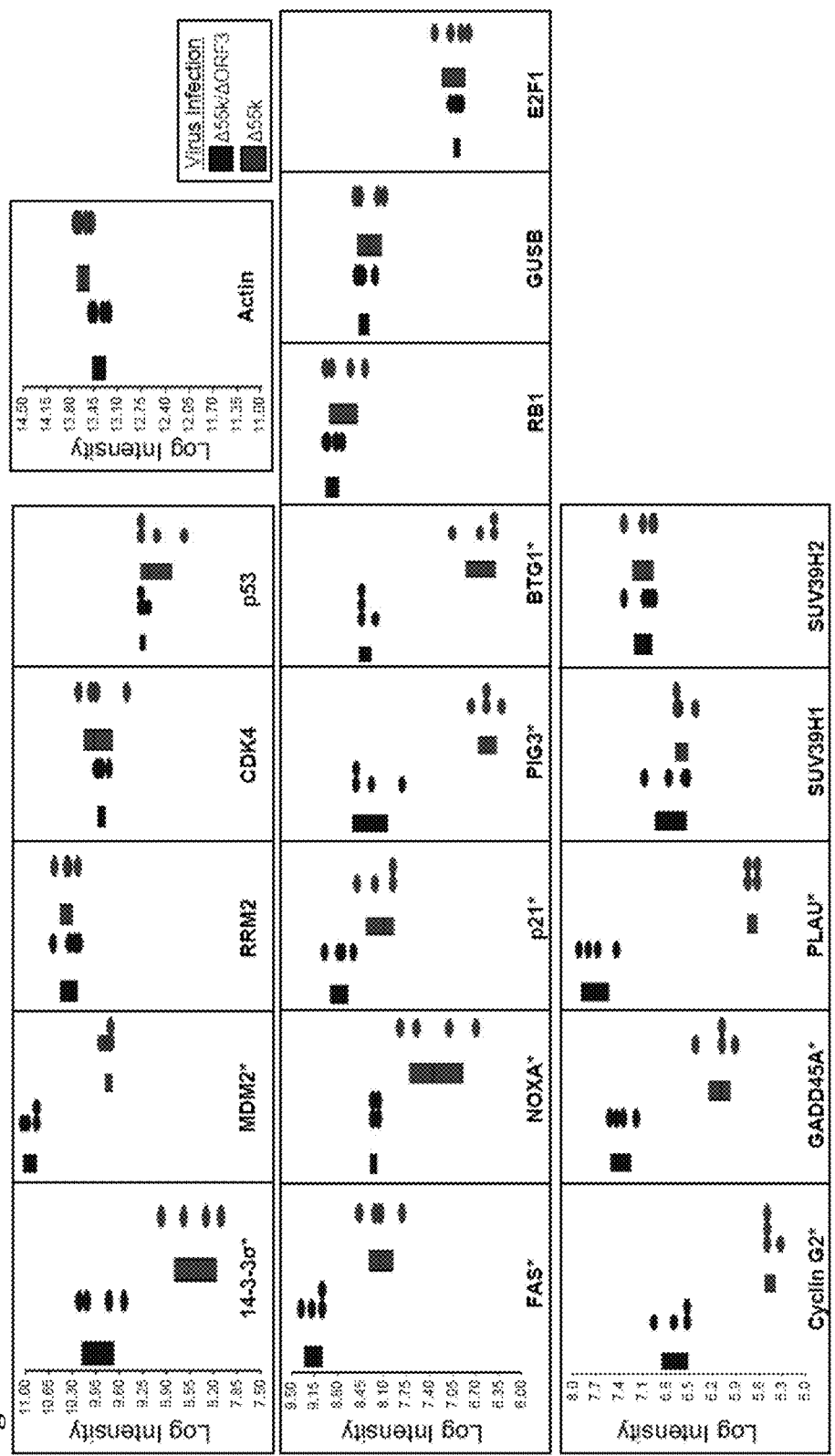

FIG. 30. Box and whiskers plots of individual gene intensity (expression) values for Δ55k and Δ55k/ΔORF3 Affymetrix array samples. The log intensity values of individual gene transcripts for Δ55k and Δ55k/ΔORF3 are plotted on the y-axis. Each dot represents an independent replicate. p53 transcriptional targets are indicated by an asterisk.

Figure 31:
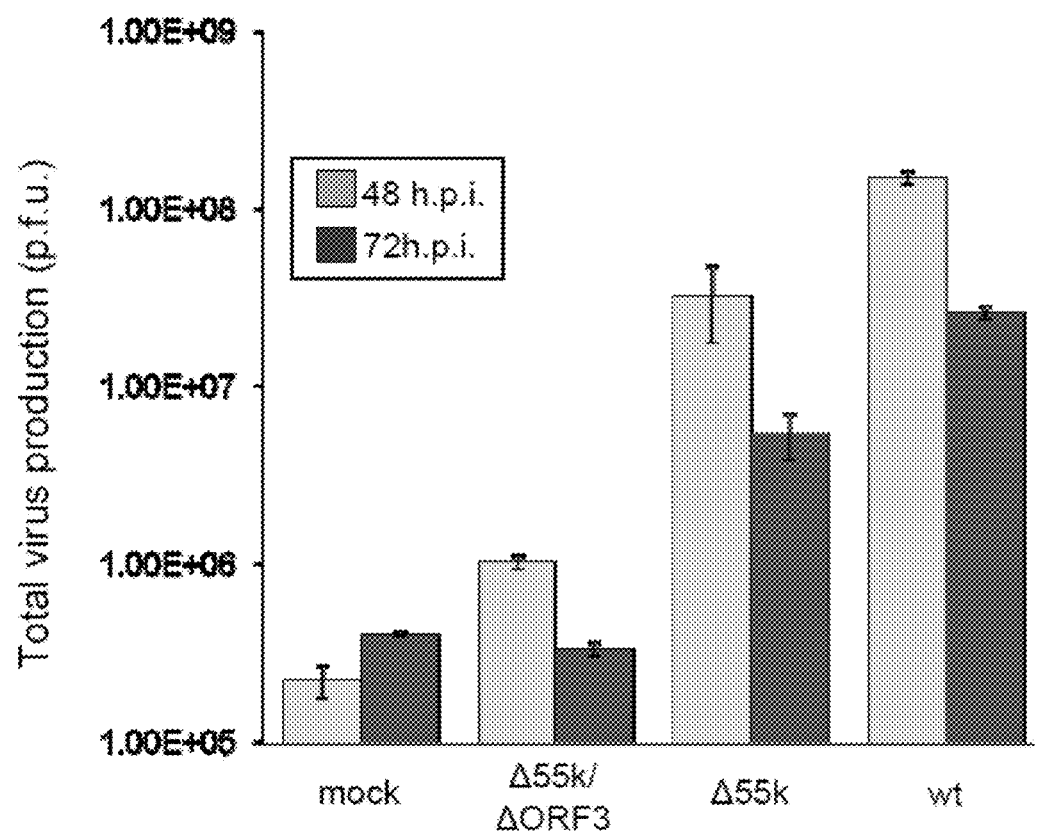

FIG. 31. ΔE1B-55k/ΔE4-ORF3 viral replication is inhibited relative to ΔE1B-55k in primary SAECs. SAECs were infected with either mock, ΔE1B-55k/ΔE4-ORF3 (Δ55k/ΔORF3), ΔE1B-55k (Δ55k), or wt viruses at a multiplicity of infection of 10 and harvested at 48 and 72 hours post infection (h.p.i.). Total virus production in plaque forming units (p.f.u.) was determined by performing viral replication assays in 293/E4 cells, as described in the methods; vertical bars represent the standard deviation across triplicates.

FIGS. 32A-32D. E4-ORF3 higher-order oligomerization is critical for its functions in inactivating p53, MRN and facilitating viral replication. (FIGS. 32A and 32D) Primary SAECs were infected with either mock, wild type Ad5 (WT), ΔE4-ORF3, ΔE1B-55K ΔE1B-55K/ΔE4-ORF3 or ΔE1B-55K/E4-ORF3 N82A adenoviruses. Protein lysates were harvested at 36 h.p.i., normalized, and immunoblotted for p53, MDM2 and p21. β-actin was analyzed as a loading control. (FIG. 32B) SAECs were infected with the indicated viruses, fixed at 36 h.p.i. and immunostained for E4-ORF3, NBS1 and DNA. (FIG. 32C) As per (FIG. 32B) except E2A viral replication domains were immunostained. (FIG. 32D) As per (FIG. 32A) except lysates were immunoblotted for Ad5 capsid proteins.

DETAILED DESCRIPTION OF THE INVENTION

Definitions

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

The terms "Ad5" and "Adenoviral genome" as used herein refer to the nucleic sequence as set forth in SEQ ID NO:3.

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., *J. Biol. Chem.* 273(52):35095-35101 (1998).

Construction of suitable vectors containing the desired therapeutic gene coding and control sequences may employ standard ligation and restriction techniques, which are well understood in the art (see Maniatis et al., in Molecular Cloning: A Laboratory Manual, Cold Spring Harbor Laboratory, New York (1982)). Isolated plasmids, DNA sequences, or synthesized oligonucleotides may be cleaved, tailored, and re-ligated in the form desired.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information, as known in the art. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

The term "recombinant" when used with reference, e.g., to a cell, virus, nucleic acid, protein, or vector, indicates that the cell, virus, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al., John Wiley & Sons.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

As used herein, the term "cancer" refers to all types of cancer, neoplasm, or malignant tumors found in mammals, including leukemia, carcinomas and sarcomas. Exemplary cancers include cancer of the brain, breast, cervix, colon, head & neck, liver, kidney, lung, non-small cell lung, melanoma, mesothelioma, ovary, sarcoma, stomach, uterus and Medulloblastoma. Additional examples include, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas, and prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). The $P_{388}$ leukemia model is widely accepted as being predictive of in vivo anti-leukemic activity. It is believed that a compound that tests positive in the $P_{388}$ assay will generally exhibit some level of anti-leukemic activity in vivo regardless of the type of leukemia being treated. Accordingly, the present invention includes a method of treating leukemia, and, preferably, a method of treating acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, and undifferentiated cell leukemia.

The term "sarcoma" generally refers to a tumor which is made up of a substance like the embryonic connective tissue and is generally composed of closely packed cells embedded in a fibrillar or homogeneous substance. Sarcomas which can be treated with a combination of antineoplastic thiol-binding mitochondrial oxidant and an anticancer agent include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with a combination of antineoplastic thiol-binding mitochondrial oxidant and an anticancer agent include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Exemplary carcinomas which can be treated with a combination of antineoplastic thiol-binding mitochondrial oxidant and an anticancer agent include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

By "therapeutically effective dose or amount" herein is meant a dose that produces effects for which it is administered. The exact dose and formulation will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); *Remington: The Science and Practice of Pharmacy*, 20th Edition, Gennaro, Editor (2003), and Pickar, *Dosage Calculations* (1999)).

The term "pharmaceutically acceptable salts" or "pharmaceutically acceptable carrier" is meant to include salts of the active compounds which are prepared with relatively non-toxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

I. Modified Adenoviruses

In one aspect, a modified adenovirus is provided. The modified adenovirus may be a p53 replication impaired adenovirus. The p53 replication impaired adenovirus is replication impaired when present within a p53 expressing cell and is not replication impaired when present within a p53 impaired cell. The term "replication impaired," as used herein, means that viral replication is attenuated when present in a p53 expressing cell compared to viral replication in p53 impaired cells. A p53 expressing cell is a cell that expresses normal levels of p53 having normal activity.

The modified adenovirus may also be a p53 replication impaired adenovirus and/or E4-ORF3 impaired. In some embodiments, the modified adenovirus is p53 replication impaired and E4-ORF3 impaired. The modified adenovirus may be an isolated adenovirus. The term "modified adenovirus," refers to an adenovirus having a gene sequence that is not found in nature (e.g. non-wild-type adenovirus). In some embodiments, the modified adenovirus is a recombinant adenovirus.

The term "p53 replication impaired," as used herein, means that, upon infection of a cell, adenovirus replication is partially or fully attenuated in the presence of normal levels of functional cellular p53. For example, if the infected cell is p53 impaired (i.e. the infected cell does not express normal levels of fully functional p53), replication of the p53 replication impaired adenovirus will proceed normally. Conversely, if a cell expresses normal levels of functional p53 (e.g. p53 with normal activity, also referred to herein as a "p53 expressing cell"), replication of the p53 replication impaired adenovirus is attenuated or prevented. A cell may be p53 impaired by failing to express normal levels of p53 (e.g. a mutation to the regulatory (e.g. promoter) region of the p53 gene) or expressing mutated p53 having below normal p53 activity. Normal levels of p53 and normal p53 activity levels are found in healthy, non-diseased cells of the same type. Thus, in some embodiments, the p53 impaired cell includes a mutated p53 gene. In some related embodiments, the p53 impaired cell includes a genome wherein the p53 gene is wholly or partially deleted. The p53 impaired cell may be a cancer (e.g. neoplastic) cell.

The term "E4-ORF3 impaired," as used herein, means the adenovirus is not capable of producing normal levels and/or fully functional E4-ORF3 gene product. For example, a virus may be E4-ORF3 impaired by failing to express normal levels of E4-ORF3 gene product as set forth in SEQ ID NO:1 (e.g. a mutation to the regulatory (e.g. promoter) region of the E4-ORF3 gene) or expressing a mutated E4-ORF3 gene product having below normal E4-ORF3 gene product activity. Thus, in some embodiments, the E4-ORF3 impaired adenovirus includes a mutated E4-ORF3 gene. In some related embodiments, the E4-ORF3 impaired adenovirus includes a genome wherein the E4-ORF3 gene is wholly or partially deleted. Without further limitation, an example for an impaired E4ORF3 protein is a E4ORF3 protein wherein amino acid residue 82 of as set forth in SEQ ID NO:1 is mutated (FIG. 32).

In some embodiments, the adenovirus is also E1B-55k impaired. The term "E1B-55k impaired," as used herein, means the adenovirus is not capable of producing normal levels and/or fully functional E1B-55k gene product as set forth in SEQ ID NO:2. For example, a virus may be E1B-55k impaired by failing to express normal levels of E1B-55k gene product (e.g. a mutation to the regulatory (e.g. promoter) region of the E4-ORF3 gene) or expressing a mutated E1B-55k gene product having below normal E4-ORF3 gene product activity. Normal levels and activities of E1B-55k gene product and E4-ORF3 gene product are levels and activities produced by wild type adenoviruses of the same type (e.g. a non-mutated adenovirus). Thus, in some embodiments, the E1B-55k impaired adenovirus includes a mutated E1B-55k gene. In some related embodiments, the E1B-55k impaired adenovirus includes a genome wherein the E1B-55k gene is wholly or partially deleted.

Various assays for determining levels and activities of protein (such as p53, E1B-55k gene product, E4-ORF3 gene product) are available, such as amplification/expression methods, immunohistochemistry methods, FISH and shed antigen assays, southern blotting, or PCR techniques. Moreover, the protein expression or amplification may be evaluated using an in vivo diagnostic assays, e.g. by administering a molecule (such as an antibody) which binds the protein to be detected and is tagged with a detectable label (e.g. a radioactive isotope) and externally scanning the patient for localization of the label. Thus, methods of measuring levels of protein levels in cells are generally known in the art and may be used to assess protein levels and/or activities in connection with the methods and compositions provided herein as applicable.

In another aspect, a cell is provided wherein the cell has been infected with the modified adenovirus described above. In some embodiments, the cell has been transformed by the modified adenovirus described above. In certain embodiments, the cell has been genetically altered as a result of the uptake, incorporation and expression of the genetic material of the modified adenovirus described above.

In some embodiments, the cell is a mammalian cell, such as a human cell. In some embodiments, the adenovirus is a mammalian adenovirus such as a human adenovirus. In some embodiments, the cell is a amphibian cell (e.g. a frog cell) or a reptilian cell (e.g. a snake cell).

Without being bound by any particular mechanistic theory, it is believed that the viral E1B-55k and E4-ORF3 gene products reduce cellular p53-mediated effects, including cellular apoptosis in response to viral infections. Thus, viral E1B-55k and E4-ORF3 gene products may act to reduce the levels of p53 in a cell, the activity of p53 in a cell, or the levels of activity of proteins that participate in a p53 mediated event (e.g. protein gene products of MDM2, FAS, PIG3, TP53INP1, BTG2, LRDD/PIDD, HRH1, RNASE7, and JMJD1C). Thus, in some embodiments, the modified adenoviruses provided herein are not capable of efficiently replicating in cells having normal p53 activity but are capable of replicating in cells having diminished p53 activity (e.g. cancer cells).

Also provided herein are nucleic acids encoding the modified adenoviruses described above. In some embodiments, one nucleic acid is provided encoding the modified adenovirus (e.g. a plasmid). In other embodiments, a plurality of nucleic acids are provided encoding the modified adenovirus (e.g. a plurality of plasmids).

II. Methods of Treating Cancer

In another aspect, a method of treating cancer is provided. The method includes administering an effective amount (e.g. a therapeutically effective dose or amount) of a modified adenovirus (as described above) or one or more nucleic acids encoding the modified adenovirus to a subject in need thereof.

In some embodiment, the cancer is a p53 related cancer. A "p53 related cancer," as described herein, is a cancer caused by a p53 impaired cancer cells. Thus, in some embodiments, the cancer to be treated herein may be one characterized by reduced expression or activity of p53 (e.g. p53 protein expressed at below normal or low levels) or by expression of p53 having low (or no) activity or lower than normal activity. Methods of determining whether a cancer is a p53 impaired cancer cells are known in the art and are generally applicable for us in conjunction with the methods and compositions provided herein.

In some embodiment, the cancer is lung cancer, skin cancer, or breast cancer. In some embodiments, the cancer to be treated is pre-malignant breast cancer.

III. Methods of Administration and Formulation

The modified viruses (or one or more nucleic acids encoding the modified adenovirus) are administered to a human patient in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, intratumoral or inhalation routes. The administration may be local or systemic.

The compositions for administration will commonly comprise an agent as described herein (e.g. a modified adenovirus or one or more nucleic acids encoding the modified adenovirus) dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs.

Thus, a typical pharmaceutical composition for intravenous administration will vary according to the agent. Actual methods for preparing parenterally administrable compositions will be known or apparent to those skilled in the art and are described in more detail in such publications as Remington's Pharmaceutical Science, 15th ed., Mack Publishing Company, Easton, Pa. (1980).

The pharmaceutical compositions can be administered in a variety of unit dosage forms depending upon the method of administration. For example, unit dosage forms suitable for oral administration include, but are not limited to, powder, tablets, pills, capsules and lozenges.

Pharmaceutical formulations, particularly, of the modified viruses can be prepared by mixing the modified adenovirus (or one or more nucleic acids encoding the modified adenovirus) having the desired degree of purity with optional pharmaceutically acceptable carriers, excipients or stabilizers. Such formulations can be lyophilized formulations or aqueous solutions. Acceptable carriers, excipients, or stabilizers are nontoxic to recipients at the dosages and concentrations used. Acceptable carriers, excipients or stabilizers can be acetate, phosphate, citrate, and other organic acids; antioxidants (e.g., ascorbic acid) preservatives low molecular weight polypeptides; proteins, such as serum albumin or gelatin, or hydrophilic polymers such as polyvinylpyllolidone; and amino acids, monosaccharides, disaccharides, and other carbohydrates including glucose, mannose, or dextrins; chelating agents; and ionic and non-ionic surfactants (e.g., polysorbate); salt-forming counter-ions such as sodium; metal complexes (e.g. Zn-protein complexes); and/or non-ionic surfactants. The modified adenovirus (or one or more nucleic acids encoding the modified adenovirus) can be formulated at any appropriate concentration of infectious units.

The formulation may also provide additional active compounds, including, chemotherapeutic agents, cytotoxic agents, cytokines, growth inhibitory agent, and anti-hormonal agent.

The compositions can be administered for therapeutic or prophylactic treatments. In therapeutic applications, compositions are administered to a patient suffering from a disease (e.g., cancer) in a "therapeutically effective dose." Amounts effective for this use will depend upon the severity of the disease and the general state of the patient's health. Single or multiple administrations of the compositions may be administered depending on the dosage and frequency as required and tolerated by the patient. A "patient" or "subject" for the purposes of the present invention includes both humans and other animals, particularly mammals. Thus the methods are applicable to both human therapy and veterinary applications. In the preferred embodiment the patient is a mammal, preferably a primate, and in the most preferred embodiment the patient is human. Other known cancer therapies can be used in combination with the methods of the invention. For example, the compositions for use according to the invention may also be used to target or sensitize a cell to other cancer therapeutic agents such as 5FU, vinblastine, actinomycin D, cisplatin, methotrexate, and the like.

In other embodiments, the methods of the invention are combined with other cancer therapies, radiation therapy, hormone therapy, or chemotherapy.

The combined administrations contemplates coadministration, using separate formulations or a single pharmaceutical formulation, and consecutive administration in either order, wherein preferably there is a time period while both (or all) active agents simultaneously exert their biological activities.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The modified adenovirus (or one or more nucleic acids encoding the modified adenovirus), alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically intratumorally, or intrathecally. Parenteral administration, intratumoral administration, and intravenous administration are the preferred methods of administration. The formulations of compounds can be presented in unit-dose or multi-dose sealed containers, such as ampules and vials.

Injection solutions and suspensions can be prepared from sterile powders, granules, and tablets of the kind previously described. Cells transduced or infected by adenovirus or transfected with nucleic acids for ex vivo therapy can also be administered intravenously or parenterally as described above.

The pharmaceutical preparation is preferably in unit dosage form. In such form the preparation is subdivided into unit doses containing appropriate quantities of the active component.

Preferred pharmaceutical preparations deliver one or more active modified adenovirus (or one or more nucleic acids encoding the modified adenovirus), optionally in combination with one or more chemotherapeutic agents or immunotherapeutic agents, in a sustained release formulation. Typically, the modified adenovirus (or one or more nucleic acids encoding the modified adenovirus) is administered therapeutically as a sensitizing agent that increases the susceptibility of tumor cells to other cytotoxic cancer therapies, including chemotherapy, radiation therapy, immunotherapy and hormonal therapy.

In therapeutic use for the treatment of cancer, the modified adenovirus (or one or more nucleic acids encoding the modified adenovirus) utilized in the pharmaceutical method of the invention are administered at the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound being employed. For example, dosages can be empirically determined considering the type and stage of cancer diagnosed in a particular patient. The dose administered to a patient, in the context of the present invention should be sufficient to affect a beneficial therapeutic response in the patient over time. The size of the dose also will be determined by the existence, nature, and extent of any adverse side-effects that accompany the administration of a particular vector, or transduced cell type in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

The pharmaceutical preparations for use according to the invention are typically delivered to a mammal, including humans and non-human mammals. Non-human mammals treated using the present methods include domesticated animals (i.e., canine, feline, murine, rodentia, and lagomorpha) and agricultural animals (bovine, equine, ovine, porcine).

IV. EXAMPLES

The following examples are offered to illustrate, but not limit the claimed invention.

There is a desperate need to identify new classes of drugs and therapeutic modalities that conclusively ablate cancer cells but leave normal cells unharmed. Engineering viruses that home in on tumor cell receptors and that replicate selectively within the tumor mass (oncolytic viruses) have enormous potential as lytic cancer therapies. The development of 'oncolytic viruses' can be achieved by exploiting the profound functional overlap between cancer mutations and adenoviral proteins. In clinical trials, the first prototypes of these agents have demonstrated promising efficacy. Without wishing to be bound by any theory, it is believed that the clinical experience and new insights into the molecular mechanisms that drive tumor and viral replication can now be used to develop novel viruses with potent and improved therapeutic properties. Unfortunately, previous methodologies to engineer such viruses fall short of this goal. Accordingly, there are provided herein enabling technologies directed to the rapid generation and targeting of therapeutic viruses. Provided herein is a novel, genetically encoded, inducible chemical adapter system that targets infection to multiple cellular receptors. Oncolytic viral therapy has the potential to destroy a tumor mass of unlimited size, but only if the virus crosses the vasculature and infection spreads from one cancer cell to another. Thus, the reliance of previous adenoviral vectors on a single cellular receptor for their uptake limits their therapeutic potential. Altering the chemistry and binding of viral capsids so that infection can be specifically targeted to any cell type is a major breakthrough. This is achieved by using a known property of the cancer drug rapamycin to dimerize heterologous proteins with FKBP and FRB domains (e.g., viruses that express a Fiber-FRB capsid protein fusion together with re-targeting ligands fused to-FKBP). These viruses infect cells via multiple re-targeting ligands upon rapamycin treatment, which is a rational and powerful combination of chemical and viral weapons directed to novel cancer therapy. Moreover, these technologies enable multi-protein complexes and entire pathways to be assembled, delivered and co-expressed in any cell type via adenoviral infection. These technologies allow 'next generation' oncolytc viruses to be developed that specifically kill p53 mutant tumors and pre-malignant breast cancer cells, and which have the potential to save the lives of many cancer patients.

A. Silencing p53 Activity at Cellular Chromatin p53 was first discovered as the cellular target of the DNA virus protein, SV40 Large T antigen. However, despite almost 30 years of p53 research, the critical factors that determine p53 activated transcription are still not fully understood. p53 is expressed constitutively in normal cells where its activity is thought to be limited by highly regulated p53 protein degradation. p53 activated transcription is triggered in response to oncogenes and DNA damage signals, both of which stabilize p53. This has led to the general belief that the induction of p53 levels and phosphorylation is synonymous with p53 transcriptional activity at target promoters in cellular chromatin. As such, the induction of p53 levels is used as a read-out for p53 activation and is the rationale for several cancer therapies, including irradiation and genotoxic drugs, MDM2 antagonists, such as nutlin, and the E1B-55k deleted oncolytic adenoviral therapy, ONYX-015.

Figure 1A:
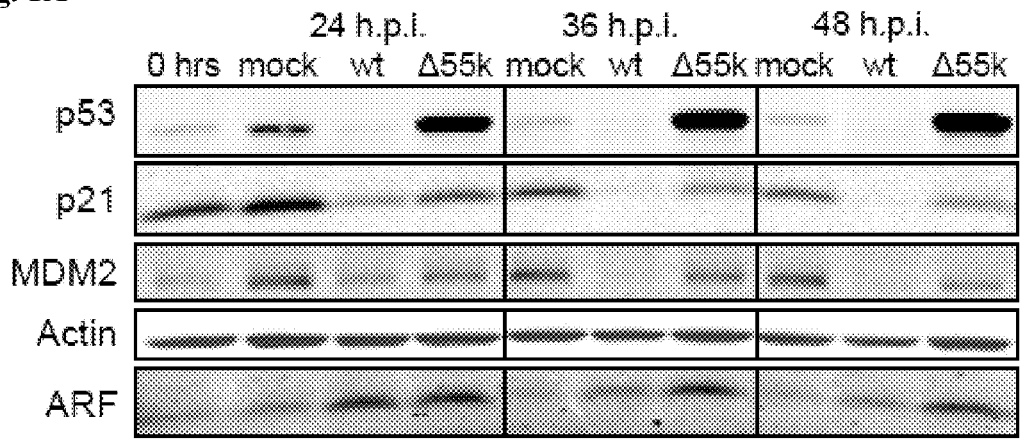
Figure 1B:
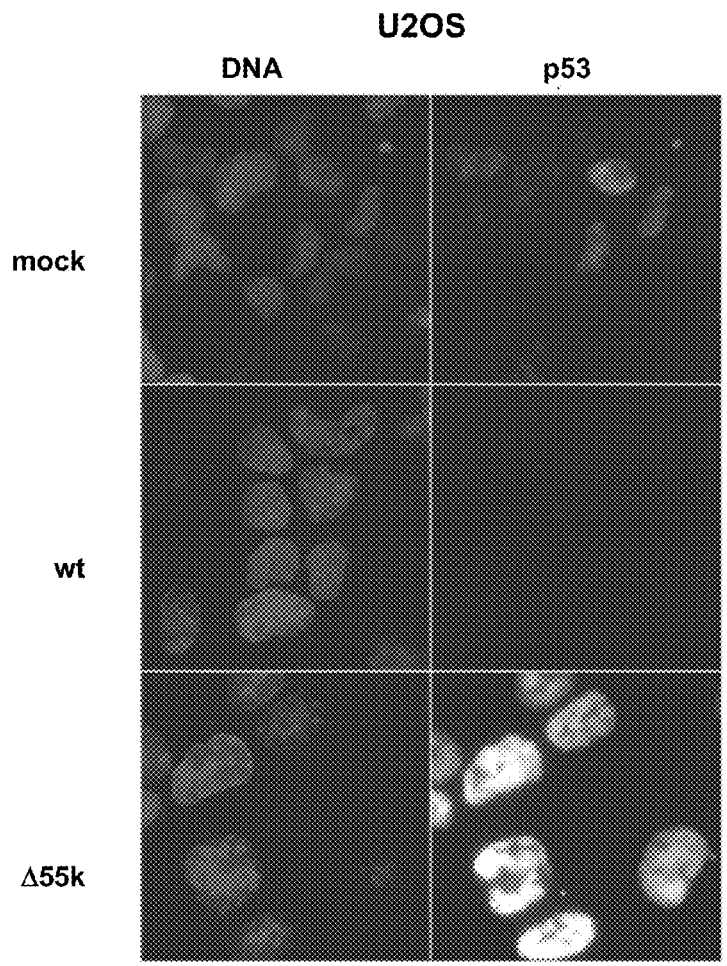

Adenovirus E1B-55k binds to the p53 transactivation domain and targets p53 for degradation in adenovirus infected cells. E1B-55k is sufficient to inhibit p53 in cellular transformation assays and is thought to be critical for p53 inactivation in adenovirus replication. A ΔE1B-55k mutant virus, dl1520/ONYX-015, induces high p53 levels in infected cells. On this basis, ONYX-015 was tested in patients as a p53 tumor selective viral cancer therapy and is now approved in several countries (now known as Oncorine). However, the loss of E1B-55k functions in viral RNA export, rather than p53 inactivation, is the major determinant of ΔE1B-55k tumor selectivity. Contrary to expectations, we found that although p53 accumulates to high levels in ΔE1B-55k infected primary small airway epithelial cells (SAECs), a physiological target cell population for adenovirus infection, p53 transcriptional targets such as p21, MDM2, Cyclin G, 14-3-3 σ, PERP, PIG3, and GADD45 are not induced (FIG. 1a). The failure to activate p53 transcriptional targets is not a tissue specific effect of p53 regulation, p53 is also stabilized in ΔE1B-55k infected primary mammary epithelial cells and bronchial epithelial cells but fails to induce p21 (Supp. FIG. 1). Similar conclusions are reached in ΔE1B-55k U2OS tumor cells, where p53 is induced to high levels in the nucleus (FIG. 1b), but fails to trigger the expression of downstream transcriptional targets, such as p21 and MDM2, in contrast to doxorubicin treatment (FIG. 1c and Supp. FIG. 2). These data demonstrate that the loss of p53 degradation results in high p53 levels in adenovirus infected cells, but despite this, the induction of p53 transcriptional targets are suppressed to a similar extent as that in cell-lines with p53 tumor mutations (C33A, MDA-MB-231 and HCT-116 p53−/−, Supp. FIG. 2). This reveals a fundamental gap in our understanding of not only adenovirus biology but also p53 activation.

Cellular and viral oncogenes, such as Ras and Adenovirus E1A, activate p53 by triggering the expression of ARF. ARF inhibits MDM2, resulting in the induction of p53 levels and activation of p53 transcriptional targets. ARF is lost in 58% of human cancers, predominantly those that retain wild-type p53, which had previously been invoked as the critical factor that prevents p53 activation in ΔE1B-55k infected tumor cells. Using a U2OS stable cell-line (p53 wild-type, ARF negative) in which ARF is regulated by IPTG, we show that ARF expression stabilizes p53 and activates p21 transcription in mock infected cells. Nevertheless, despite the induction of ARF and basal p53 activity, p21 levels are still repressed to similar levels in both wild-type and Δ55k infected cells (FIG. 1d). Furthermore, in ΔE1B-55k infected primary SAECs, endogenous ARF expression also fails to activate p53 transcriptional targets (FIG. 1a). Thus, p53 is inactivated, irrespective of E1B-55k and ARF expression in adenovirus infected cells.

DNA damage signals also play a critical role in activating p53, triggering p53 phosphorylation and protein stabilization. We reasoned that the induction of p53 levels alone may not be sufficient to activate p53 in ΔE1B-55k infected cells, and that DNA damage signals are also required. In clinical trials, the ΔE1B-55k mutant virus, ONYX-015, was used in combination with genotoxic chemotherapies, such as 5-fluorouracil (5-FU). Therefore, we tested whether DNA damage signals are necessary to activate p53 targets in ΔE1B-55k infected cells. We show that treatment with 5-FU fails to activate p53 in ΔE1B-55k infected U2OS cells (FIG. 2a). Given that the DNA damage checkpoint is disrupted by mutations in many tumor cells, we also analyzed primary cells, and demonstrate that p53 transcriptional targets are dominantly suppressed in ΔE1B-55k infected SAECs and cannot be activated by γ irradiation (FIG. 2b), UV irradiation (Supp. FIG. 3) or doxorubicin (FIG. 2d).

The activation of p53 in response to DNA damage is mediated via kinases, such as ATM, ATR, DNA-PKcs, CHK1 and CHK2, which phosphorylate p53 at key residues. For example, phosphorylation of p53 at serine 15 and 20 displaces MDM2, preventing p53 degradation, while phosphorylation at other sites potentiates p53 DNA binding at target promoters. Therefore, a possible explanation for the failure of DNA damage to activate high p53 levels in ΔE1B-55k infected cells is that p53 phosphorylation is being inhibited in viral infection. However, even without the introduction of exogenous genotoxic stress, p53 is already highly phosphorylated in ΔE1B-55k infected primary cells at multiple sites targeted by DNA damage activated kinases (FIG. 2c). Thus, in the absence of E1B-55k, oncogene and DNA damage signals trigger both the stabilization and phosphorylation of p53, but despite this, p53 is biologically inert and fails to activate the transcription of downstream effectors.

We next examined if in the absence of E1B-55k, MDM2 binds and inactivates p53 in adenovirus infected cells. Nutlin is a small molecule antagonist of MDM2 that inhibits MDM2-p53 binding and the induction of p53 degradation. In contrast to mock infected cells, the inhibition of MDM2-p53 binding by nutlin fails to stabilize p53 further or induce p21 levels in ΔE1B-55k infected SAECs (FIG. 2d). These results are consistent with the similar failure of ARF overexpression to activate p53 in ΔE1B-55k infected U2OS cells (FIG. 1d).

Taken together, our data demonstrate that the transcriptional activation of p53 target promoters is being repressed in adenovirus infected cells irrespective of p53 induction. The histone deacetylase (HDAC) inhibitor, trichostatin A (TSA), is a general transcriptional activator that induces the expression of p21 (as well as multiple other cellular genes). In mock infected primary cells, TSA induces p21 expression independently of p53 stabilization or phosphorylation (FIG. 2d). In contrast, in ΔE1B-55k infected cells, TSA fails to induce the transcription of p21. We conclude that p53 transcriptional targets are dominantly suppressed in adenovirus infected cells, irrespective of E1B-55k, and cannot be activated in response to radiation, genotoxic drugs, ARF, MDM2 antagonists or HDAC inhibitors. Defining this mechanism is important for understanding not only p53 activation but also how it could be manipulated for cancer therapy.

Our data strongly suggest that there is a previously undiscovered adenoviral protein that inactivates p53 independent of E1B-55k and p53 degradation. To test this, we used a genetic approach, and screened for p53 activation in primary cells infected with adenoviruses that have compound mutations in E1B-55k and other early viral genes (Supp. FIG. 4). We discovered that in addition to deleting E1B-55k, the loss of either the 13s splice form of E1A (E1A-13s) or E4-ORF3 is required to activate p53 in adenovirus infected cells (FIG. 3a). Our finding that, in addition to E1B-55k, adenovirus encodes two viral proteins that inactivate p53 is surprising, especially since E1A is a potent oncogene that triggers p53 activation in cellular transformation studies. In adenovirus infection, the alternative 13s splice form of E1A is required for the transactivation of other early viral genes, including E4-ORF3 (FIG. 3a). Therefore, we hypothesized that E1A-13s inactivates p53 by inducing the expression of E4-ORF3 in viral infection. Consistent with this hypothesis, we show that in contrast to Ad-GFP, the ectopic expression of E4-ORF3 is sufficient to rescue p53 inactivation in both $\Delta$E1B-55k/$\Delta$E4-ORF3 and $\Delta$E1B-55k/$\Delta$E1A-13s infected cells (FIG. 3b). The slight reduction of p21 by Ad-GFP in $\Delta$E1B-55k/$\Delta$E4-ORF3 co-infected cells is due to the partial activation of E4-ORF3 (in trans) by E1A-13s, which does not occur in $\Delta$E1B-55k/$\Delta$E1A-13s co-infection (Supp. FIG. 5). Hence, the induction of E4-ORF3 expression by E1A-13s inactivates p53 in adenovirus infected cells via a novel E1B-55k independent mechanism.

The proposed p53 tumor selectivity of the $\Delta$E1B-55k oncolytic adenovirus therapy, ONYX-015 (Oncorine), is based on E1B-55k being the critical and sole mechanism whereby p53 is inactivated in adenovirus infected cells. Although there may be some basal p53 activity in $\Delta$E1B-55k infected cells compared to wild-type virus, here we show that the additional deletion of E4-ORF3 is necessary for the induction of p53 levels to activate the transcription of downstream targets, over the time-course of viral infection in primary cells (FIG. 3c). The induction of p53 levels is required to activate p53 transcriptional targets, and does not occur in $\Delta$E4-ORF3 infection where p53 is targeted for degradation by E1B-55k. Furthermore, we show that E4-ORF3 prevents the activation of multiple p53 transcriptional targets, including cell cycle arrest, DNA repair and apoptosis genes (FIG. 3d). Relative to mock infection, E4-ORF3 represses the transcription of some p53 targets, such as p21, and prevents the induction of others, such as PUMA and MDM2. In contrast to p53 transcriptional targets, the transcriptional induction of p53 mRNA levels and steady-state mRNA levels of the housekeeping gene, GUSB, are not affected by E4-ORF3 (Supp. FIG. 6). Using a p53-null stable cell-line (H1299-D1) with a ponasterone inducible p53 (FIG. 3e and Supp. FIG. 7), we show that the induction of p21 and MDM2 in $\Delta$E1B-55k/$\Delta$E4-ORF3 infected cells is p53-dependent and not the result of global transcriptional activation in the absence of E4-ORF3. Since H1299-D1 cells express a p53 cDNA, these experiments also demonstrate that E4-ORF3 does not inactivate p53 by inducing alternative p53 splice forms. We conclude that E4-ORF3 has a critical and novel role in inactivating p53 that functions independently of E1B-55k and p53 degradation.

DNA tumor virus proteins, such as E1B-55k, SV40 LT and HPV E6 generally inactivate p53 via high affinity protein-protein interactions. However, contrary to this established paradigm, E4-ORF3 does not co-localize with p53 (Supp. FIG. 8). Furthermore, in contrast to E1B-55k, E4-ORF3 does not co-immunoprecipitate with p53 in lysates from either virally infected cells or cells transfected with epitope tagged constructs. This suggests that E4-ORF3 inactivates p53 via a non-canonical mechanism.

The induction of p53 levels and phosphorylation normally drives p53 tetramerization and conformational changes that facilitate sequence-specific DNA binding at the promoters of regulated genes where it recruits transcription co-factors to activate their expression. An active versus inactive p53 DNA binding domain (DBD) can be distinguished by immunoprecipitation with monoclonal antibody PAb 1620 versus PAb 240, respectively. In both $\Delta$E1B-55k and $\Delta$E1B-55k/$\Delta$E4-ORF3 infected cells, p53 is immunoprecipitated selectively by PAb 1620 (Supp. FIG. 9), demonstrating that p53 has an active DNA binding domain protein conformation that should be capable of binding to DNA target sites in cellular promoters. To functionally determine if E4-ORF3 prevents p53 DNA binding, we transfected U2OS cells with p53 luciferase reporter plasmids (p53-luc), where p53 binding to consensus DNA sequences activates luciferase transcription. These experiments were performed by measuring luciferase activity in real-time over a 48 hour time-course of viral infection. A control pGL3-luciferase reporter (non-p53 target promoter) is activated to similar levels in all viral infections (Supp. FIG. 10). In wild-type virus infected cells, p53 activated transcription of luciferase is inhibited after 24 hours (FIG. 4a), which is expected due to p53 degradation (FIG. 1c). In contrast, p53-luciferase is activated in both $\Delta$E1B-55k and $\Delta$E1B-55k/$\Delta$E4-ORF3 infection (FIG. 4a). The induction of luciferase activity requires p53 DNA binding, since a promoter with a mutated p53 response element abolishes luciferase activity. These experiments demonstrate that E4-ORF3 does not compete with p53 for binding to consensus DNA target sequences or prevent p53 transcriptional activation of promoters in ectopic reporter plasmids.

The ability of E4-ORF3 to prevent p53 activated transcription of endogenous targets but not ectopic luciferase reporter plasmids in the same cells is difficult to reconcile (FIG. 4b). Plasmid DNA is not subject to the same architectural and packing constraints as DNA in cellular chromatin. Therefore, we performed p53 chromatin immunoprecipitations (ChIPs) to determine if E4-ORF3 specifically prevents p53 DNA binding in the context of cellular chromatin. p53 DNA binding to target sites in the p21 (5' and 3' site) and MDM2 promoters is induced upon doxorubicin treatment and $\Delta$E1B-55k/$\Delta$E4-ORF3 infection, where it activates the transcription of p21 and MDM2 RNAs (FIG. 4b-c). In contrast, although p53 is induced to similar levels in $\Delta$E1B-55k infected cells, we show that E4-ORF3 prevents p53 DNA binding to target sites in the p21 and MDM2 promoters (FIG. 4b-c and Supp. FIG. 11). Consequently, the induction of p53 fails to trigger the transcription of downstream effectors in $\Delta$E1B-55k infected cells. Thus, E4-ORF3 inactivates p53 by preventing p53 binding to DNA target sites specifically in the context of cellular chromatin.

We reasoned that p53 DNA binding depends not only on the protein conformation of p53 but also on the accessibility of target promoters in the cellular genome. Developmentally regulated genes are epigenetically silenced in embryogenesis by their compaction into heterochromatin, thereby preventing access for transcription factor binding in somatic cells. Heterochromatin is specified by the loss of histone acetylation and induction of repressive histone methylation marks. We hypothesized that E4-ORF3 could inactivate p53 by inducing heterochromatin at endogenous target promoters, preventing access to p53. Consistent with this, the histone deacetylase inhibitor, TSA, fails to induce p21 in $\Delta$E1B-55k infected primary cells (FIG. 2d). From this we infer that E4-ORF3 inactivates p53-regulated promoters via a mechanism that is dominant to the inhibition of histone deacetylation, such as histone methylation. In cancer, the aberrant epigenetic silencing of tumor suppressor genes, such as p161NK4a, is initiated by the methylation of histone H3 at lysine 9 (H3K9). The induction of H3K9 trimethylation (H3K9me3) by SUV39H1 and SUV39H2 (which share 59% amino acid identity and have redundant functions) also plays a critical role in inducing the compaction and transcriptionally repressive characteristics of DNA in pericentromeric heterochromatin. p53 localization is indistinguishable in ΔE1B-55k versus ΔE1B-55k/ΔE4-ORF3 infected cells (FIG. 4d). However, in ΔE1B-55k infected cells, where p53 is inactive, dense regions of H3K9me3 repressive heterochromatin are induced at the periphery of the nucleus (FIG. 4d and Supp. FIG. 12). Of the four known methyltransferases that catalyze H3K9 trimethylation, we show that SUV39H1 and SUV39H2 31, but not SETDB1 32 or G9a, are specifically associated with the formation of de novo H3K9me3 heterochromatin domains in ΔE1B-55k infected nuclei (FIG. 4e). The formation of SUV39H1/2 associated H3K9me3 heterochromatin domains requires E4-ORF3 and does not occur in either mock or ΔE1B-55k/ΔE4-ORF3 infected cells (Supp. FIG. 13-16).

These data demonstrate that E4-ORF3 induces novel SUV39H1 and SUV39H2 H3K9me3 heterochromatin formation, which could deny p53 access to endogenous target promoters. To test this directly, we performed p53 and H3K9me3 ChIPs. The induction of repressive heterochromatin by E4-ORF3 is not associated with a global upregulation of either total histone H3 or H3K9me3, which are at similar levels in mock, ΔE1B-55k and ΔE1B-55k/ΔE4-ORF3 lysates (FIG. 5a). In ΔE1B-55k/ΔE4-ORF3 infected cells, we show that p53 binding is induced at p21 and MDM2 promoter sites (consistent with FIG. 4c) while H3K9me3 is at IgG levels (FIG. 5a and Supp. FIG. 17). In contrast, in ΔE1B-55k infected cells, H3K9me3 is induced at the p21 and MDM2 promoters and p53 binding is prevented. At the p21 promoter, H3K9me3 is also induced at the −5 kb region and is not restricted to just the p53 binding sites (Supp. FIG. 17). Thus, in cells expressing E4-ORF3, there is an inverse correlation between p53 and H3K9me3 at p53 regulated promoters. The same conclusions were reached for additional p53 targets repressed in ΔE1B-55k infected cells, including GADD45A, FAS, PUMA and PIG3 (Supp. FIG. 17-19). In contrast, H3K9me3 at non-p53 regulated promoters, such as Actin and POLR2, is not induced in ΔE1B-55k infected cells compared to mock (Supp. FIGS. 17 and 19). Basal H3K9me3 is decreased at these promoters in ΔE1B-55k/ΔE4-ORF3 infected cells, suggesting that E4-ORF3 may also restrain global demethylase activity in viral infection. We conclude that E4-ORF3 inactivates p53 by inducing de novo H3K9me3 heterochromatin silencing at p53 target promoters, and with access denied, p53 is powerless to activate the transcription of downstream effectors.

The induction of heterochromatin formation in mammalian cells and cancer is still relatively poorly understood. Thus, a major question is how is E4-ORF3 directly involved in inducing repressive H3K9me3 heterochromatin at p53 target promoters? E4-ORF3 does not co-localize with p53 and forms a distinctive web-like structure in the nucleus (Supp. FIG. 8). We show that E4-ORF3 demarcates the formation of de novo H3K9me3 heterochromatin domains in both ΔE1B-55k infected tumor and primary cells. Orthogonal slices through the nucleus reveal that E4-ORF3 is, for the most part, adjacent to H3K9me3, suggesting it acts as a novel platform that catalyses heterochromatin formation through transient or long-range interactions (FIG. 5b-c, and Supp. FIG. 20-21). Using high resolution confocal microscopy, we show that E4-ORF3 forms a continuous scaffold that organizes and specifies de novo heterochromatin assembly as it weaves through the nucleus (FIG. 5d). These data demonstrate a direct role for E4-ORF3 in orchestrating H3K9me3 heterochromatin silencing at p53 target promoters. Furthermore, they reveal an extraordinary nuclear scaffold that either builds on existing architectural features that organize cellular DNA or is a novel viral construction that targets heterochromatin assembly at p53 target promoters.

These data beg the question as to the specificity of E4-ORF3 silencing for p53 targets as well as the global consequences of such a machination on cellular transcription. Therefore, to determine the specificity and global physiological consequences of E4-ORF3 on cellular transcription, we performed genome-wide expression analyses on primary human quiescent SAECs (Supp. FIGS. 22 and 23). These studies demonstrate that E4-ORF3 is an exclusive player in the global transcriptional changes induced upon viral infection in quiescent SAECs. There are 1730 overlapping genes that are up or downregulated by a log fold change greater than two in Δ55k and Δ55k/ΔORF3 versus mock infected SAECs, which are similarly regulated and reflect a common transcriptional program (FIG. 6a). We show that these global changes in gene expression are associated with the cell cycle and E2F activation, which is expected due to the inactivation of the RB family of tumor suppressor proteins by E1A. These data are also consistent with E1A induced enrichment of an active histone mark, Histone H3 lysine 18 acetyl (H3K18ac), via p300 and PCAF at the promoters of genes involved in cell growth, division and DNA synthesis. Thus, E4-ORF3 induced heterochromatin silencing, as well as the scaffold it forms throughout the nucleus, does not affect the global activation of cellular transcripts induced by viral infection.

To define the genes specifically targeted by E4-ORF3, we compared ΔE1B-55k/ΔE4-ORF3 versus ΔE1B-55k infected cells. E4-ORF3 prevents the transcriptional activation of 265 genes by a log fold change of two or more in ΔE1B-55k infected cells. To estimate how many of these are likely to be regulated by p53, we used two criteria: the presence of consensus p53 DNA binding sites in their promoters and whether the same genes are also upregulated in cells treated with the MDM2 antagonist, nutlin (FIG. 6b). We show that 71% of the 265 differentially upregulated genes are induced in response to nutlin and/or have predicted p53 binding sites. A heat map of top transcripts upregulated in response to ΔE1B-55k/ΔE4-ORF3 and nutlin includes well known p53 targets (MDM2, FAS, PIG3, TP53INP1, BTG2, LRDD/PIDD) that are associated with growth inhibition and apoptosis as well as novel targets (HRH1, RNASE7, JMJD1C) (FIG. 6c and Supp. FIG. 24). There are 76 upregulated genes that do not have either predicted p53 binding sites or are upregulated in response to nutlin. A pathway analysis of E4-ORF3 regulated transcripts indicates that in addition to the p53 pathway, there is a significant overrepresentation of genes associated with immune modulation as well as tissue/vascular remodeling. These data suggest that E4-ORF3 may target p53 promoters as part of a general anti-viral transcriptional silencing program, which is consistent with the highly defective replication of ΔE1B-55k/ΔE4-ORF3 (Supp. FIG. 25).

The conclusions of our study challenge the general assumption that p53 induction and phosphorylation is tantamount to p53 activity, which is the premise for several p53-targeted cancer therapies. Our data reveal a novel and dominant mechanism of p53 inactivation that acts via the targeted epigenetic silencing of p53 target promoters in somatic human cells. We identify a viral protein, E4-ORF3, which forms a novel scaffold that weaves through the nucleus and directs SUV39H1/2 H3K9me3 heterochromatin assembly at p53 target promoters to silence p53 activated transcription in response to genotoxic and oncogenic stress (FIG. 6d). Remarkably, this suppressive nuclear web selectively ensnares p53 and anti-viral genes and operates in the backdrop of global transcriptional changes that drive pathological cellular and viral replication.

Figure 32A:
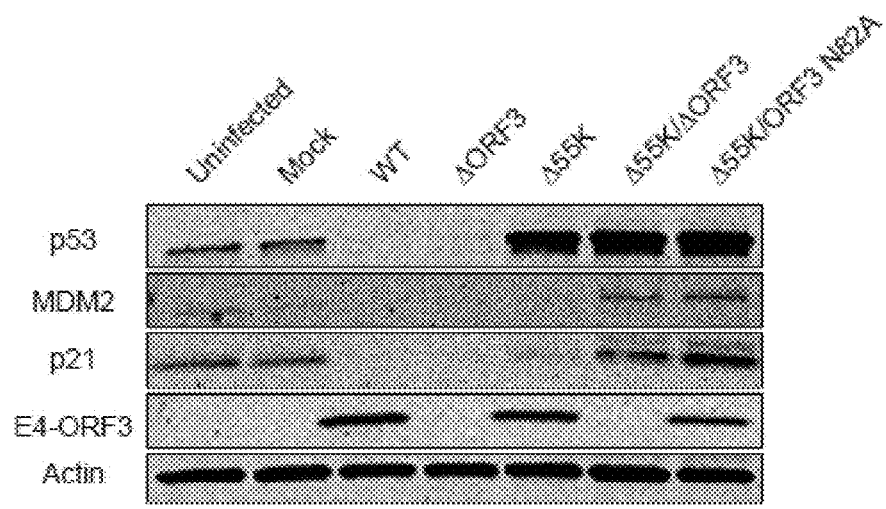
Figure 32B:
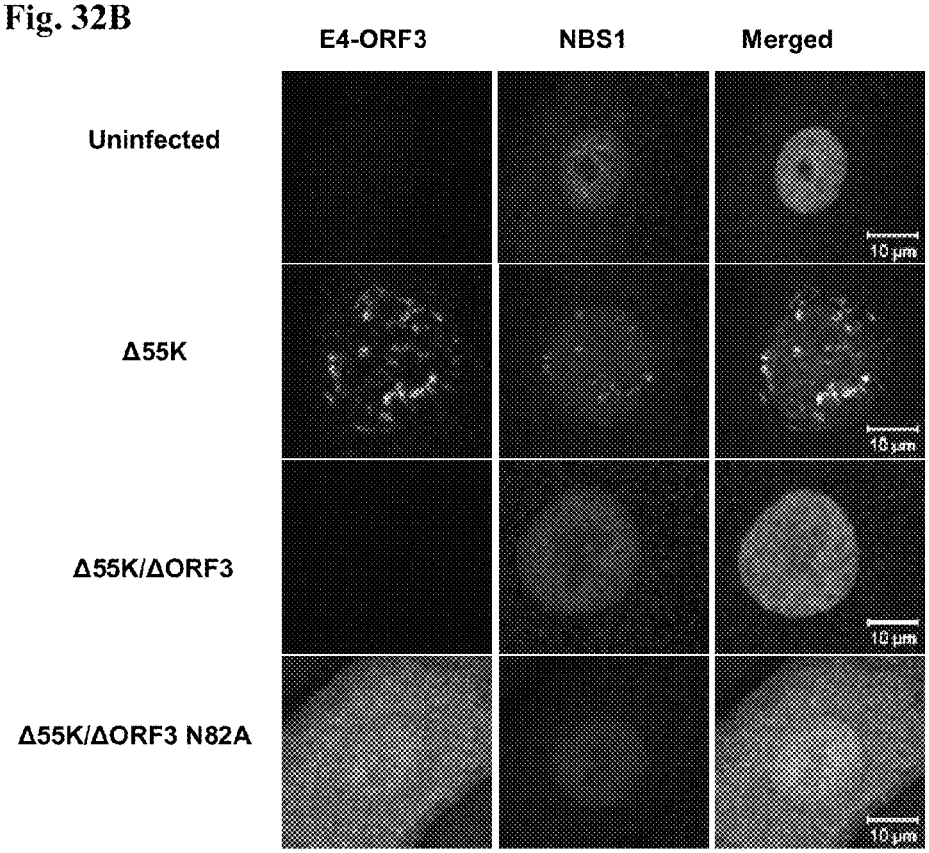
Figure 32C:
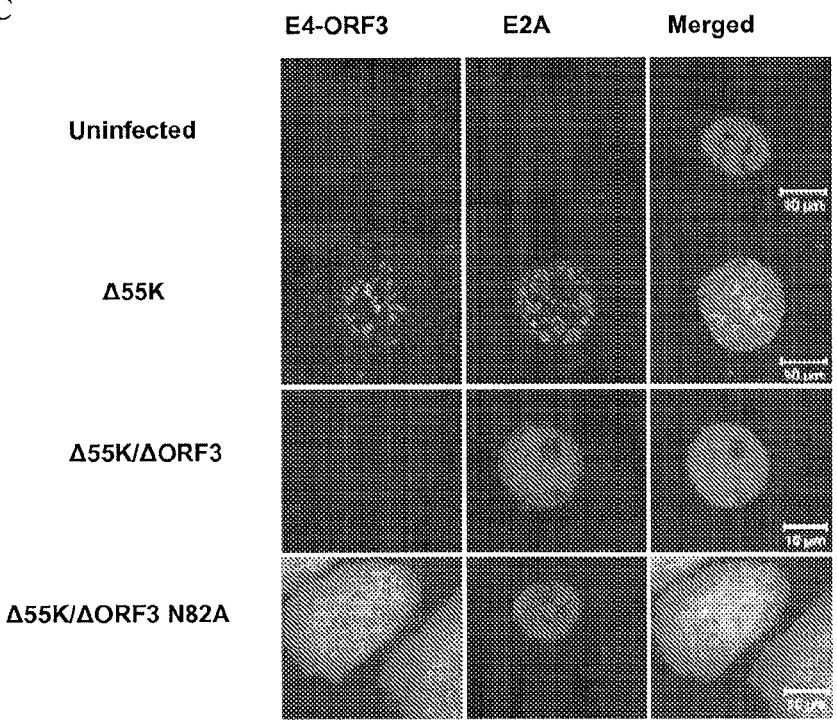
Figure 32D:
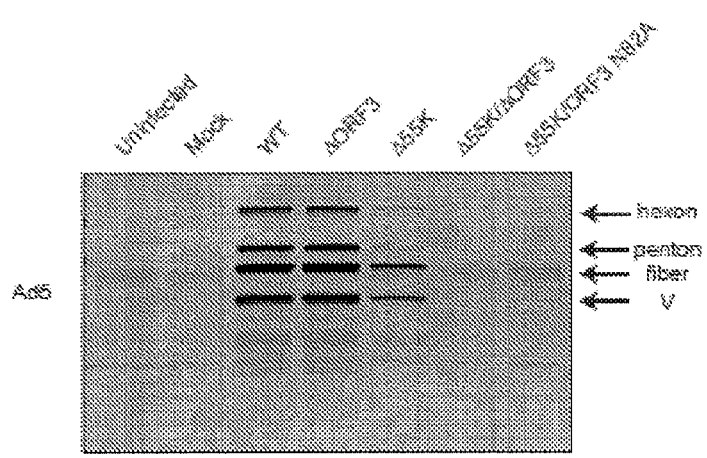

Adenoviral E1B-55K targets p53 for proteosomal degradation. However, E4-ORF3 inactivates p53 independently of E1B-55K by silencing p53 target promoters. Thus, the deletion of both E1B-55K and E4-ORF3 are necessary to activate p53 in adenovirus infected cells. Applicant's structural and oligomerization studies have revealed that an E4-ORF3 N82A mutant protein is functionally folded but adopts a closed configuration that prevents higher order oligomerization. Therefore, to determine if E4-ORF3 higher order assembly is necessary for p53 inactivation novel adenoviruses were engineered that are null for E1B-55K and express E4-ORF3 N82A instead of wild type E4-ORF3. E4-ORF3 prevents p53 activated transcription of p21 and MDM2 in ΔE1B-55K infected cells, (FIG. 32A). In contrast, in ΔE1B-55K/E4-ORF3 N82A infected cells, E4-ORF3 is unable to undergo higher order oligomerization and inactivate p53 (FIG. 32A). Similar conclusions were reached for different classes of p53 targets. Thus, E4-ORF3 N82A behaves as a complete null. Applicants conclude that the higher order oligomerization of E4-ORF3 is critical for inactivating p53 mediated gene expression.

There is a profound functional overlap between adenovirus early proteins and tumor mutations, which has led to the identification of many of the key growth regulatory mechanisms, including E2F and the p300/CBP histone acetyltransferase. Thus, a major question is if E4-ORF3 reflects or exhorts an existing mechanism and nuclear structure that also censors p53 transcriptional activity in normal cells or tumorigenesis. Strikingly, all of the known cellular targets of E4-ORF3, PML 39, the MRE11/RAD50/NBS1 (MRN) DNA damage/repair complex and Tif1α are also subverted by tumor mutations. It is intriguing to speculate that E4-ORF3 physically integrates the inhibitory effects of several cancer pathway mutations, both known and perhaps yet to be discovered, which together have emergent functions in silencing p53 activity. Similar to the discovery of p53 with a viral protein, E4-ORF3 provides a powerful dynamic probe with which to define critical cellular factors that induce de novo and targeted epigenetic silencing of p53 target promoters in somatic human cells. This has important implications for understanding how high p53 levels might also be inactivated in cancer cells as well as the mechanisms that induce the aberrant epigenetic silencing of tumor suppressor gene loci in tumorigenesis. Finally, our identification of E4-ORF3 changes the fundamental definition of how p53 is inactivated in adenovirus infected cells, which is a critical mechanistic insight that could now enable the rational development of true p53 tumor selective adenoviral therapies.

What is claimed is:

1. A method of treating a cancer with reduced expression or activity of p53, comprising administering an effective amount of a recombinant adenovirus that is E1B-55k impaired and E4-ORF3 impaired to a subject in need thereof, wherein the recombinant adenovirus is not replication impaired in a p53 impaired cell.

2. The method of claim 1, wherein the cancer is lung cancer, skin cancer or breast cancer.

3. The method of claim 1, wherein the cancer to be treated is pre-malignant breast cancer.

4. The method of claim 1, wherein the recombinant adenovirus expresses a mutated E4-ORF3 product.

5. The method of claim 1, wherein the recombinant adenovirus comprises an E4-ORF3 gene that is wholly or partially deleted.

6. The method of claim 1, wherein the recombinant adenovirus expresses a mutated E1B-55k gene product.

7. The method of claim 1, wherein the recombinant adenovirus comprises an E1B-55k gene that is wholly or partially deleted.

8. The method of claim 1, wherein the recombinant adenovirus comprises an E4-ORF3 gene that is wholly or partially deleted and an E1B-55k gene that is wholly or partially deleted.

9. The method of claim 1, wherein the recombinant adenovirus comprises a mutated E4-ORF3 gene and an E1B-55k gene that is wholly or partially deleted.

* * * * *